(12) United States Patent
Christensen, IV et al.

(10) Patent No.: US 7,709,497 B2
(45) Date of Patent: May 4, 2010

(54) PYRAZOLO[3,4-B]PYRIDINE COMPOUND, AND ITS USE AS A PDE4 INHIBITOR

(75) Inventors: Siegfried Benjamin Christensen, IV, Collegeville, PA (US); Caroline Mary Cook, Stevenage (GB); Christopher David Edlin, Stevenage (GB); Martin Redpath Johnson, Stevenage (GB); Paul Spencer Jones, Stevenage (GB); Mika Kristian Lindvall, Emeryville, CA (US); Amyn Pyarali Sayani, Mississauga (CA); Naimisha Trivedi, Stevenage (GB); Lionel Trottet, Les Ulis (FR)

(73) Assignee: Glaxo Group Limited, Greenford, Middlesex (GB)

( * ) Notice: Subject to any disclaimer, the term of this patent is extended or adjusted under 35 U.S.C. 154(b) by 112 days.

(21) Appl. No.: 10/598,838

(22) PCT Filed: Mar. 15, 2005

(86) PCT No.: PCT/EP2005/003038

§ 371 (c)(1),
(2), (4) Date: Jul. 11, 2007

(87) PCT Pub. No.: WO2005/090352

PCT Pub. Date: Sep. 29, 2005

(65) Prior Publication Data

US 2007/0280971 A1    Dec. 6, 2007

(30) Foreign Application Priority Data

Mar. 16, 2004    (GB)    .................................. 0405893.9
Mar. 14, 2005    (GB)    .................................. 0505214.7

(51) Int. Cl.
  *A61K 31/44*    (2006.01)
  *A01N 43/42*    (2006.01)
  *C07D 471/02*   (2006.01)
  *C07D 491/02*   (2006.01)
  *C07D 498/02*   (2006.01)

(52) U.S. Cl. ...................................... 514/303; 546/120

(58) Field of Classification Search .................. 546/120; 514/303

See application file for complete search history.

(56) References Cited

U.S. PATENT DOCUMENTS

| | | |
|---|---|---|
| 3,755,340 A | 8/1973 | Hoehn et al. |
| 3,833,594 A | 9/1974 | Hoehn et al. |
| 3,833,598 A | 9/1974 | Denzel et al. |
| 3,840,546 A | 10/1974 | Hoehn et al. |
| 3,856,799 A | 12/1974 | Hoehn et al. |
| 3,925,388 A | 12/1975 | Hoehn et al. |
| 3,966,746 A | 6/1976 | Hoehn et al. |
| 3,979,399 A | 9/1976 | Hoehn et al. |
| 4,115,394 A | 9/1978 | Hoehn et al. |
| 5,593,997 A | 1/1997 | Dow et al. |
| 2005/0043319 A1 | 2/2005 | Schweighoffer et al. |
| 2006/0089375 A1 | 4/2006 | Allen et al. |
| 2006/0252790 A1 | 11/2006 | Allen et al. |
| 2007/0111995 A1* | 5/2007 | Allen ....................... 514/227.8 |
| 2008/0275078 A1* | 11/2008 | Cook et al. .................. 514/303 |

FOREIGN PATENT DOCUMENTS

| | | |
|---|---|---|
| CA | 1003419 | 1/1977 |
| CH | 553 799 | 9/1974 |
| EP | 0 076 035 | 4/1983 |
| EP | 0 180 318 | 5/1986 |
| GB | 141 7489 | 12/1973 |
| GB | 151 1006 | 4/1975 |
| JP | 2002-020386 | 1/2002 |
| WO | WO-00/15222 | 3/2000 |
| WO | WO-01/23389 A2 | 4/2001 |
| WO | WO-01/44244 A1 | 6/2001 |
| WO | WO-02/060900 | 8/2002 |
| WO | WO-02/081463 | 10/2002 |
| WO | WO-02/098878 | 12/2002 |
| WO | WO-03/016563 | 2/2003 |
| WO | WO 2004/024728 A | 3/2004 |
| WO | WO-2004/024728 A2 | 3/2004 |
| WO | WO 2004/056823 A | 7/2004 |
| WO | WO-2004/056823 A1 | 7/2004 |
| WO | WO-2005/058892 | 6/2005 |

(Continued)

OTHER PUBLICATIONS

DeKorte et al., American journal of health-system pharmacy : AJHP : official journal of the American Society of Health-System Pharmacists, (Oct. 1, 2003) vol. 60, No. 19, pp. 1949-1959; quiz 1960-1. Ref: 89 Journal code: 9503023. ISSN: 1079-2082.*

(Continued)

*Primary Examiner*—D. Margaret Seaman
*Assistant Examiner*—Niloofar Rahmani
(74) *Attorney, Agent, or Firm*—James M. Kanagy; Edward R. Gimmi; Charles M. Kinzig

(57) ABSTRACT

The invention provides 4-{[1-(aminocarbonyl)-4-piperidinyl]amino}-N-[(3,4-dimethylphenyl)methyl]-1-ethyl-1H-pyrazolo[3,4-b]pyridine-5-carboxamide, which is the compound of formula (I):

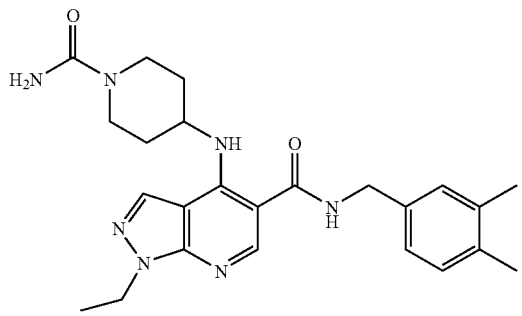

(I)

or a salt thereof.

13 Claims, No Drawings

FOREIGN PATENT DOCUMENTS

| WO | WO-2005/090348 | 9/2005 |
|---|---|---|
| WO | WO-2005/090353 | 9/2005 |
| WO | WO-2005/090354 | 9/2005 |

OTHER PUBLICATIONS

U.S. Appl. No. 10/598,973, filed Mar. 2005, Cook, et al.

U.S. Appl. No. 10/598,838, filed Mar. 2005, Christensen, IV.

Bare T.M. et al.; Synthesis and structure-activity relationships of a series of anxioselective pyrazolopyridine ester and amide anxiolytic agents; Journal of Medicinal Chemistry; 1989; 32; pp. 2561-2573.

Beer B., et al., "Enhancement of 3H-diazepam binding by SQ 65,396: a novel anti-anxiety agent"; Pharmacology Biochemistry & Behaviour; 1978; 9; pp. 849-851.

Bondavalli F. et al; Synthesis, molecular modelling studies, and pharmacological activity of selective A1 receptor antagonists; Journal of Medicinal Chemistry; 2002; 45(22); pp. 4875-4887.

Chakravorti; Synthesis of Some Isoguinolylpyrazolo[3,4-b]pyridine Derivates as Possible Antifilarial Agents; Indian J. Chem.; Feb. 1978; Vol. 16B, pp. 161-163.

Chasin M., et al.; "1-Ethyl-4-(isopropylidenehydrazino)-1H-pyrazolo-(3,4-b)-pyridine-5-carboxylic acid, ethyl ester, hydrochloride (SQ 20009)—a potent new inhibitor of cyclic 3',5'-nucleotide phosphodiesterases"; Biochemical Pharmacology; 1972; 21; pp. 2443-2450.

Chemical Abstracts Registry—CAS registry No. 502143-17-1 which has the laboratory code NSC 235755, Apr. 8, 2003.

Daly J. W. et al.; 1-methyl-4-substituted-1H-pyrazolo [3, 4-b] pyridine-5-carboxylic acid derivatives: effect of structural alterations on activity at A1 and A2 adenosine receptors; Medicinal Chemistry Research; 1994; 4(5); pp. 293-306; Birkhaeuser; Boston US.

Davis A., et al.,; "Strategic approaches to drug design. II. Modelling studies on phosphodiesterase substrates and inhibitors"; Journal of Computer-Aided Molecular Design; 1987; 1; pp. 97-119.

De Mello, A. Echevarria, et al.; Antileishmnial Pyrazolopyridine Derivatives: Synthesis and Structure-Activity Relationship Analysis; Journal of Medicinal Chemistry; 2004; 47(22); pp. 5427-5432.

Denzel TH.; (translation of title: New Synthesis of 1-Unsubstituted 1H-Pyrazolo [3.4-b] Pyridine-5-Carboxylic Acid Esters); Archiv der Pharmazie; 1974; 307(3); pp. 177-186.

Giembycz M.A.; Phosphodiesterase 4 Inhibitors and the Treatment of Asthma: Where Are We Now and Where Do We Go from Here?; Drugs; 2000; 59(2); pp. 193-212.

Glass II, W. F., et al.; "Inhibition of human lung cyclic GMP and cyclic AMP phosphodiesterases by certain nucleosides, nucleotides, and pharmacological phosphodiesterase inhibitors"; Biochemical Pharmacology; 1979; 28; pp. 1107-1112.

Hoehn H. et al.; 1H-pyrazolo[3,4-b]pyridines; Journal of Heterocyclic Chemistry; 1972; 9(2); pp. 235-253.

Hohn H et al: Potential Antidiabetic Agents. Pyrazolo63,4-b!pyridinesW Journal of Medicinal Chemistry, American Chemical Society. Washington, US, vol. 16, No. 12, 1973, pp. 1340-1346, XP002097814 ISSN: 0022-2623 p. 1343; compound 37.

Horowitz Z. P., et al.; "Cyclic AMP and anxiety"; Psychosomatics; 1972; vol. XIII, No. 2; pp. 85-92.

Kripalani K. J. et al.; "Biotransformation in the monkey of cartazolate (SQ 65,396), a substituted pyrazolopyridine having anxiolytic activity"; Xenobiotica; 1981; 11(7); pp. 481-488.

Ochiai H. et al.; Discovery of new orally active phosphodiesterase (PDE4) inhibitors; Chem. Pharm. Bull.; 2004 (stated to have been published online Jun. 15, 2004); 52(9); pp. 1098-1104.

Ochiai H. et al.; Bioorg. Med. Chem. Web Release; 2003.

Ochiai H. et al.; New orally active PDE4 inhibitors with therapeutic potential; Bioorg. Med. Chem.; 2004 (stated to have been available online Jun. 20, 2004); 12(15); pp. 4089-4100.

Ochiai H. et al.; New orally active PDE4 inhibitors with therapeutic potential; Bioorg. Med. Chem. Lett.; Jan. 5, 2004 issue (available as "articles in press" version on or before Dec. 4, 2003, possibly Oct. 2003, via internet); 14(1); pp. 29-32.

Patel J.B. and Malick J.B.; Pharmacological properties of tracazolate: a new non-benzodiazepine anxiolytic agent; Eur. J. Pharmacol.; 1982; 78; pp. 323-333.

Patel J.B., et al.; "Pharmacology of pyrazolopyridines"; Pharmacology Biochemistry & Behaviour; 1985; vol. 23; pp. 675-680.

Polson J. B., et al.; "Analysis of the relationship between pharmacological inhibition of cyclic nucleotide phosphodiesterase and relaxation of canine tracheal smooth muscle"; Biochemical Pharmacology; 1979; 28; pp. 1391-1395.

RBI 1998, Catalogue No. T-112, Tracazolate; 1998; p. 340.

Sabitha, et al.; A Facile Route to Pyrazolo[3,4-b]Pyridines and [1]Benzopyrano[4',3'- e]Pyrazolo[3,4-b]Pyridines; Indian Institute of Chemical Technology; 1999; 29(4),655-665; Synthetic Communications; India.

Schenone S. et al.; Synthesis and biological data of 4-amino-1-(2-chloro-2-phenylethyl)-1H-pyrazolo[3,4-b]pyridine-5-carboxylic acid ethyl esters, a new series of A1-adenosine receptor (A1AR) ligands; Bioorg. Med. Chem. Lett.; 2001; 11; pp. 2529-2531.

Shi D., et al.; Pyrazolopyridines: effect of structural alterations on activity at adenosine- and GABA-A receptors; Drug Development Research; 1997; 42; pp. 41-56.

Weinryb I., et al.; "Studies in vitro and in vivo with SQ-20,009: an inhibitor of cyclic nucleoside phosphodiesterase with central nervous system activity"; Excerpta Med. Int. Congr. Ser.; 1975; 359; pp. 857-865.

Yu G., Mason H.J., et al.; Substituted pyrazolopyridines as potent and selective PDE5 inhibitors: potential agents for treatment of erectile disfunction; Journal of Medicinal Chemistry; 2001; 44; pp. 1025-1027.

Horn H et al: Potential Antidiabetic Agents. Pyrazolo63,4-b!pyridinesW Journal of Medicinal Chemistry, American Chemical Society. Washington, US, vol. 16, No. 12, 1973, pp. 1340-1346, XP002097814 ISSN: 0022-2623 p. 1343; compound 37.

Patent Abstracts of Japan vol . 2002, No. 5, May 3, 2002 -& JP 2002 020386 A (On0 Pharmaceut Co Ltd) , Jan. 23, 2002 cited in the application abstract.

* cited by examiner

PYRAZOLO[3,4-B]PYRIDINE COMPOUND, AND ITS USE AS A PDE4 INHIBITOR

This application claims the benefits of International Application No. PCT/EP2005/003038, filed 15-Mar.-2005, which claims the priority of GB0405893.9.

The present invention relates to a pyrazolo[3,4-b]pyridine compound or a salt thereof, processes for its preparation, intermediates usable in these processes, and to pharmaceutical compositions containing the compound or salt. The invention also relates to the use of the pyrazolo[3,4-b]pyridine compound or salt thereof in therapy, for example as an inhibitor of phosphodiesterase type IV (PDE4) and/or for the treatment and/or prophylaxis of inflammatory and/or allergic diseases such as chronic obstructive pulmonary disease (COPD), asthma, rheumatoid arthritis, allergic rhinitis, psoriasis or atopic dermatitis. The invention relates in particular to the external topical use, e.g. skin-topical use, of the compound or salt in the treatment and/or prophylaxis of atopic dermatitis in a mammal such as a human.

BACKGROUND TO THE INVENTION

U.S. Pat. Nos. 3,979,399, 3,840,546, and 3,966,746 (E.R. Squibb & Sons) disclose 4-amino derivatives of pyrazolo[3,4-b]pyridine-5-carboxamides wherein the 4-amino group $NR_3R_4$ can be an acyclic amino group wherein $R_3$ and $R_4$ may each be hydrogen, lower alkyl (e.g. butyl), phenyl, etc.; $NR_3R_4$ can alternatively be a 3-6-membered heterocyclic group such as pyrrolidino, piperidino and piperazino. The compounds are disclosed as central nervous system depressants useful as ataractic, analgesic and hypotensive agents.

U.S. Pat. Nos. 3,925,388, 3,856,799, 3,833,594 and 3,755,340 (E.R. Squibb & Sons) disclose 4-amino derivatives of pyrazolo[3,4-b]pyridine-5-carboxylic acids and esters. The 4-amino group $NR_3R_4$ can be an acyclic amino group wherein $R_3$ and $R_4$ may each be hydrogen, lower alkyl (e.g. butyl), phenyl, etc.; $NR_3R_4$ can alternatively be a 5-6-membered heterocyclic group in which an additional nitrogen is present such as pyrrolidino, piperidino, pyrazolyl, pyrimidinyl, pyridazinyl or piperazinyl. The compounds are mentioned as being central nervous system depressants useful as ataractic agents or tranquilisers, as having antiinflammatory and analgesic properties. The compounds are mentioned as increasing the intracellular concentration of adenosine-3',5'-cyclic monophosphate and for alleviating the symptoms of asthma.

H. Hoehn et al., *J. Heterocycl. Chem.*, 1972, 9(2), 235-253 discloses a series of 1H-pyrazolo[3,4-b]pyridine-5-carboxylic acid derivatives with 4-hydroxy, 4-chloro, 4-alkoxy, 4-hydrazino, and 4-amino substituents. Ethyl 4-(n-butylamino)-1-ethyl-1H-pyrazolo[3,4-b]-pyridine-5-carboxylate is disclosed therein; this compound is cartazolate.

The compound tracazolate, ethyl 4-(n-butylamino)-1-ethyl-6-methyl-1H-pyrazolo[3,4-b]-pyridine-5-carboxylate, is known as an anxiolytic agent (e.g. see J. B. Patel et al., *Eur. J. Pharmacol.*, 1982, 78, 323). Other 1-substituted 4-($NH_2$ or NH-alkyl)-1H-pyrazolo[3,4-b]-pyridine-5-carboxylic acid esters and amides are disclosed as potential anxiolytic agents in T. M. Bare et al., *J. Med. Chem.*, 1989, 32, 2561-2573.

CA 1003419, CH 553 799 and T. Denzel, *Archiv der Pharmazie*, 1974, 307(3), 177-186 disclose 4,5-disubstituted 1H-pyrazolo[3,4-b]pyridines unsubstituted at the 1-position.

Japanese laid-open patent application JP-2002-20386-A (Ono Yakuhin Kogyo KK) published on 23 Jan. 2002 discloses pyrazolopyridine compounds of the following formula:

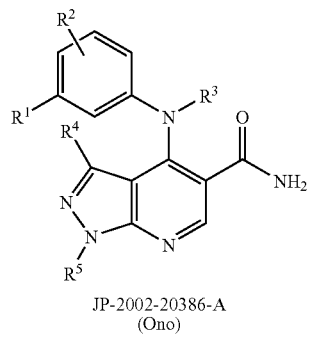

JP-2002-20386-A
(Ono)

wherein $R^1$ denotes 1) a group $—OR^6$, 2) a group $—SR^7$, 3) a C2-8 alkynyl group, 4) a nitro group, 5) a cyano group, 6) a C1-8 alkyl group substituted by a hydroxy group or a C1-8 alkoxy group, 7) a phenyl group, 8) a group $—C(O)R^8$, 9) a group $—SO_2NR^9R^{10}$, 10) a group $—NR^{11}SO_2R^{12}$, 11) a group $—NR^{13}C(O)R^{14}$ or 12) a group $—CH=NR^{15}$. $R^6$ and $R^7$ denote i) a hydrogen atom, ii) a C1-8 alkyl group, iii) a C1-8 alkyl group substituted by a C1-8 alkoxy group, iv) a trihalomethyl group, v) a C3-7 cycloalkyl group, vi) a C1-8 alkyl group substituted by a phenyl group or vii) a 3-15 membered mono-, di- or tricyclic hetero ring containing 1-4 nitrogen atoms, 1-3 oxygen atoms and/or 1-3 sulphur atoms. $R^2$ denotes 1) a hydrogen atom or 2) a C1-8 alkoxy group. $R^3$ denotes 1) a hydrogen atom or 2) a C1-8 alkyl group. $R^4$ denotes 1) a hydrogen atom, 2) a C1-8 alkyl group, 3) a C3-7 cycloalkyl group, 4) a C1-8 alkyl group substituted by a C3-7 cycloalkyl group, 5) a phenyl group which may be substituted by 1-3 halogen atoms or 6) a 3-15 membered mono-, di- or tricyclic hetero ring containing 1-4 nitrogen atoms, 1-3 oxygen atoms and/or 1-3 sulphur atoms. $R^5$ denotes 1) a hydrogen atom, 2) a C1-8 alkyl group, 3) a C3-7 cycloalkyl group, 4) a C1-8 alkyl group substituted by a C3-7 cycloalkyl group or 5) a phenyl group which may be substituted by 1-3 substituents. In group $R^3$, a hydrogen atom is preferred. In group $R^4$, methyl, ethyl, cyclopropyl, cyclobutyl or cyclopentyl are preferred. The compounds of JP-2002-20386-A are stated as having PDE4 inhibitory activity and as being useful in the prevention and/or treatment of inflammatory diseases and many other diseases.

1,3-Dimethyl-4-(arylamino)-pyrazolo[3,4-b]pyridines with a 5-C(O)$NH_2$ substituent similar or identical to those in JP-2002-20386-A were disclosed as orally active PDE4 inhibitors by authors from Ono Pharmaceutical Co. in: H. Ochiai et al., *Bioorg. Med. Chem. Lett.*, 5th Jan. 2004 issue, vol. 14(1), pp. 29-32 (available on or before 4th Dec. 2003 from the Web version of the journal: "articles in press"). Full papers on these and similar compounds as orally active PDE4 inhibitors are: H. Ochiai et al., *Bioorg. Med. Chem.*, 2004, 12(15), 4089-4100 (stated to have been available online 20 Jun. 2004), and H. Ochiai et al., *Chem. Pharm. Bull.*, 2004, 52(9), 1098-1104 (stated to have been published online 15 Jun. 2004).

EP 0 076 035 A1 (ICI Americas) discloses pyrazolo[3,4-b]pyridine derivatives as central nervous system depressants useful as tranquilisers or ataractic agents for the relief of anxiety and tension states.

J. W. Daly et al., *Med. Chem. Res.*, 1994, 4, 293-306 and D. Shi et al., *Drug Development Research*, 1997, 42, 41-56 disclose a series of 4-(amino) substituted 1H-pyrazolo[3,4-b] pyridine-5-carboxylic acid derivatives, including ethyl 4-cyclopentylamino-1-methyl-1H-pyrazolo[3,4-b]pyridine-5-carboxylate, and their affinities and antagonist activities at $A_1$- and $A_{2A}$-adenosine receptors, and the latter paper discloses their affinities at various binding sites of the $GABA_A$-receptor channel. S. Schenone et al., *Bioorg. Med. Chem. Lett.*, 2001, 11, 2529-2531, and F. Bondavalli et al., *J. Med. Chem.*, 2002, vol. 45 (Issue 22, 24 Oct. 2002, allegedly published on Web Sep. 24, 2002), pp. 4875-4887 disclose a series of 4-amino-1-(2-chloro-2-phenylethyl)-1H-pyrazolo[3,4-b]pyridine-5-carboxylic acid ethyl esters as $A_1$-adenosine receptor ligands.

WO 02/060900 A2 appears to disclose, as MCP-1 antagonists for treatment of allergic, inflammatory or autoimmune disorders or diseases, a series of bicyclic heterocyclic compounds with a —C(O)—NR$^4$—C(O)—NR$^5$R$^6$ substituent, including isoxazolo[5,4-b]pyridines and 1H-pyrazolo[3,4-b]pyridines (named as pyrazolo[5,4-b]pyridines) with the —C(O)—NR$^4$—C(O)—NR$^5$R$^6$ group as the 5-substituent and optionally substituted at the 1-, 3-, 4-, and/or 6-positions. Bicyclic heterocyclic compounds with a —C(O)NH$_2$ substituent instead of the —C(O)—NR$^4$—C(O)—NR$^5$R$^6$ substituent are alleged to be disclosed in WO 02/060900 as intermediates in the synthesis of the —C(O)—NR$^4$—C(O)—NR$^5$R$^6$ substituted compounds. See also WO 02/081463 A1 for similar MCP-1 antagonists.

WO 00/15222 (Bristol-Myers Squibb) discloses inter alia pyrazolo[3,4-b]pyridines having inter alia a C(O)—X$_1$ group at the 5-position and a group E$_1$ at the 4-position of the ring system. Amongst other things, X$_1$ can for example be —OR$_9$, —N(R$_9$)(R$_{10}$) or —N(R$_5$)(-A$_2$-R$_2$), and E$_1$ can for example be —NH-A$_1$-cycloalkyl, —NH-A$_1$-substituted cycloalkyl, or —NH-A$_1$-heterocyclo; wherein A$_1$ is an alkylene or substituted alkylene bridge of 1 to 10 carbons and A$_2$ can for example be a direct bond or an alkylene or substituted alkylene bridge of 1 to 10 carbons. The compounds are disclosed as being useful as inhibitors of cGMP phosphodiesterase, especially PDE type V, and in the treatment of various cGMP-associated conditions such as erectile dysfunction. Compounds with a cycloalkyl or heterocyclo group directly attached to —NH— at the 4-position of the pyrazolo[3,4-b]pyridine ring system and/or having PDE4 inhibitory activity do not appear to be disclosed in WO 00/15222.

G. Yu et. al., *J. Med. Chem.*, 2001, 44, 1025-1027 discloses some 4-[(3-chloro-4-methoxybenzyl)amino]-pyrazolopyridine-5-carboxamides as selective PDE5 inhibitors.

H. de Mello, A. Echevarria, et al., *J. Med. Chem.*, 2004, 47 (22), 5427-5432, believed to have been published online on or before 21 Sep. 2004, discloses 3-methyl or 3-phenyl 4-anilino-1H-pyrazolo[3,4-b]pyridine 5-carboxylic esters as potential anti-*Leishmania* drugs.

Copending patent application PCT/EP2003/014867, filed on 19 Dec. 2003 in the name of Glaxo Group Limited, published on 8 Jul. 2004 as WO 2004/056823 A1, discloses and claims pyrazolo[3,4-b]pyridine compounds or salts thereof with a 4-NR$^3$R$^{3a}$ group (R$^{3a}$ is preferably H) and with a group Het at the 5-position of the pyrazolo[3,4-b]pyridine, wherein Het is usually a 5-membered optionally substituted heteroaryl group. PCT/EP2003/014867 (WO 2004/056823 A1) also discloses the use of these compounds as PDE4 inhibitors and for the treatment and/or prophylaxis of inter alia COPD, asthma or allergic rhinitis.

Copending patent application PCT/EP03/11814, filed on 12 Sep. 2003 in the name of Glaxo Group Limited, published on 25 Mar. 2004 as WO 2004/024728 A2, discloses pyrazolo[3,4-b]pyridine compounds or salts thereof with a 4-NHR$^3$ group and a 5-C(O)—X group, according to this formula (I):

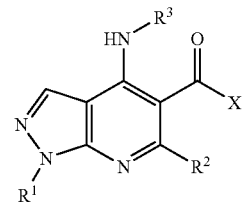

wherein:
R$^1$ is $C_{1-4}$alkyl, $C_{1-3}$fluoroalkyl, —CH$_2$CH$_2$OH or —CH$_2$CH$_2$CO$_2$C$_{1-2}$alkyl;
R$^2$ is a hydrogen atom (H), methyl or $C_1$fluoroalkyl;
R$^3$ is optionally substituted $C_{3-8}$cycloalkyl or optionally substituted mono-unsaturated-$C_{5-7}$cycloalkenyl or an optionally substituted heterocyclic group of sub-formula (aa), (bb) or (cc);

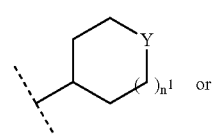

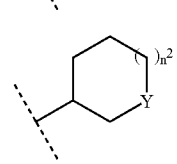

in which n$^1$ and n$^2$ independently are 1 or 2; and in which Y is O, S, SO$_2$, or NR$^{10}$; where R$^{10}$ is a hydrogen atom (H), $C_{1-4}$alkyl, $C_{1-2}$fluoroalkyl, CH$_2$C(O)NH$_2$, C(O)NH$_2$, C(O)—$C_{1-2}$alkyl, C(O)—$C_1$fluoroalkyl or —C(O)—CH$_2$O—$C_{1-2}$alkyl; or R$^3$ is a bicyclic group (dd) or (ee):

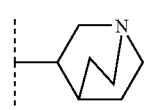

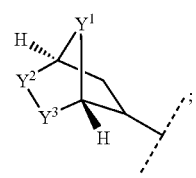

and wherein X is NR$^4$R$^5$ or OR$^{5a}$.
In PCT/EP03/11814 (WO 2004/024728 A2), R$^4$ is a hydrogen atom (H); $C_{1-6}$alkyl; $C_{1-3}$fluoroalkyl; or $C_{2-6}$alkyl substituted by one substituent R$^{11}$.
In PCT/EP03/11814 (WO 2004/024728 A2), R$^5$ can be: a hydrogen atom (H); $C_{1-8}$alkyl; $C_{1-8}$ fluoroalkyl; $C_{3-8}$cycloalkyl optionally substituted by a $C_{1-2}$alkyl group; —$(CH_2)_n{}^4$—$C_{3-8}$cycloalkyl optionally substituted, in the —$(CH_2)_n{}^4$— moiety or in the $C_{3-8}$cycloalkyl moiety, by a $C_{1-2}$alkyl group, wherein $n^4$ is 1, 2 or 3; $C_{2-6}$alkyl substituted by one or two independent substituents $R^{11}$; —$(CH_2)_n{}^{11}$—C(O)$R^{16}$; —$(CH_2)_n{}^{12}$—C(O)N$R^{12}R^{13}$; —CH$R^{19}$—C(O)N$R^{12}R^{13}$; —$(CH_2)_n{}^{12}$—C(O)O$R^{16}$; —$(CH_2)_n{}^{12}$—C(O)OH; —CH$R^{19}$—C(O)O$R^{16}$; —CH$R^{19}$—C(O)OH; —$(CH_2)_n{}^{12}$—$SO_2$—N$R^{12}R^{13}$; —$(CH_2)_n{}^{12}$—$SO_2R^{16}$; or —$(CH_2)_n{}^{12}$—CN; —$(CH_2)_n{}^{13}$-Het; or optionally substituted phenyl.

Alternatively, in PCT/EP03/11814 (WO 2004/024728 A2), $R^5$ can have the sub-formula (x), (y), (y1) or (z):

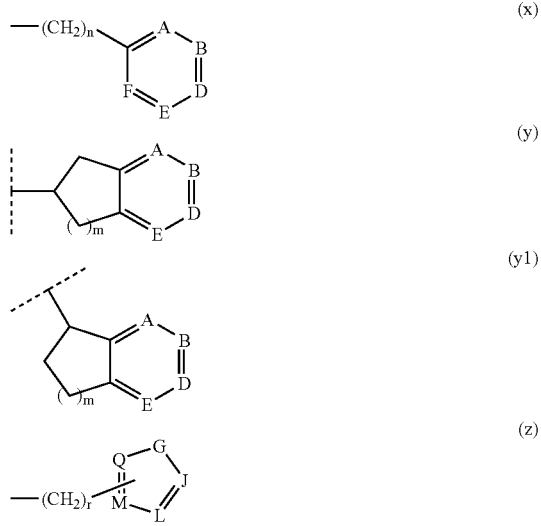

wherein in sub-formula (x), n=0, 1 or 2; in sub-formula (y) and (y1), m=1 or 2; and in sub-formula (z), r=0, 1 or 2; and wherein in sub-formula (x) and (y) and (y1), none, one or two of A, B, D, E and F are independently nitrogen or nitrogen-oxide ($N^+$—$O^-$) provided that no more than one of A, B, D, E and F is nitrogen-oxide, and the remaining of A, B, D, E and F are independently CH or C$R^6$; and provided that when n is 0 in sub-formula (x) then one or two of A, B, D, E and F are independently nitrogen or nitrogen-oxide ($N^+$—$O^-$) and no more than one of A, B, D, E and F is nitrogen-oxide;

In PCT/EP03/11814 (WO 2004/024728 A2), each $R^6$, independently of any other $R^6$ present, is: a halogen atom; $C_{1-6}$alkyl; $C_{1-4}$fluoroalkyl; $C_{1-4}$alkoxy; $C_{1-2}$fluoroalkoxy; $C_{3-6}$cycloalkyloxy; —C(O)$R^{16a}$; —C(O)O$R^{30}$; —S(O)$_2$—$R^{16a}$; $R^{16a}$—S(O)$_2$—N$R^{15a}$—; $R^7R^8$N—S(O)$_2$—; $C_{1-2}$alkyl-C(O)—$R^{15a}$N—S(O)$_2$—; $C_{1-4}$alkyl-S(O)—; Ph-S(O)—; $R^7R^8$N—CO—; —N$R^{15}$—C(O)$R^{16}$; $R^7R^8$N; OH; $C_{1-4}$alkoxymethyl; $C_{1-4}$alkoxyethyl; $C_{1-2}$alkyl-S(O)$_2$—$CH_2$—; $R^7R^8$N—S(O)$_2$—$CH_2$—; $C_{1-2}$alkyl-S(O)$_2$—N$R^{15a}$—$CH_2$—; —$CH_2$—OH; —$CH_2CH_2$—OH; —$CH_2$—N$R^7R^8$; —$CH_2$—$CH_2$—N$R^7R^8$; —$CH_2$—C(O)O$R^{30}$; —$CH_2$—C(O)—N$R^7R^8$; —$CH_2$—N$R^{15a}$—C(O)—$C_{1-3}$alkyl; —$(CH_2)_n{}^{14}$-Het$^1$ where $n^{14}$ is 0 or 1; cyano (CN); $Ar^{5b}$; or phenyl, pyridinyl or pyrimidinyl wherein the phenyl, pyridinyl or pyrimidinyl independently are optionally substitutes by one or two of fluoro, chloro, $C_{1-2}$alkyl, $C_1$fluoroalkyl, $C_{1-2}$alkoxy or $C_1$fluoroalkoxy; or two adjacent $R^6$ taken together can be —O—(C$Me_2$)-O— or —O—$(CH_2)_n{}^{14}$—O— where $n^{14}$ is 1 or 2.

The pyrazolo[3,4-b]pyridine compounds of formula (I) and salts thereof disclosed in PCT/EP03/11814 (WO 2004/024728 A2) are disclosed as being inhibitors of phosphodiesterase type IV (PDE4), and as being useful for the treatment and/or prophylaxis of a variety of diseases/conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder), depression, or pain. PCT/EP03/11814 (WO 2004/024728 A2) states that the compounds of formula (I) and/or their pharmaceutical compositions may be administered by oral, parenteral, inhaled (topical to the lung), or nasal administration. However, the use of the pyrazolo[3,4-b]pyridine compounds by external topical administration is not disclosed.

Also, PCT/EP03/11814 (WO 2004/024728 A2) does not disclose any specific pyrazolo[3,4-b]pyridine compounds having a 4-position group NH$R^3$ in which $R^3$ is an optionally substituted heterocyclic group of sub-formula (aa), (bb) or (cc) and in which Y is N$R^{10}$ wherein $R^{10}$ is C(O)NH$_2$.

WO 2004/024728 has been reviewed, and WO 2004/056823 mentioned, in *Expert Opin. Ther. Patents*, 2005 (January edition), 15(1), 111-114.

The Invention

We have now found a new pyrazolo[3,4-b]pyridine compound which, according to current measurements, is a potent inhibitor of phosphodiesterase type IV (PDE4) enzyme subtypes B (PDE4B) and D (PDE4D), which inhibits PDE4 in a whole blood (WB) assay, and which appears to inhibit the PDE4B enzyme more strongly than it inhibits the PDE3 or PDE5 enzymes. From a preliminary test, the compound appears to be capable of being used by external topical administration in the treatment and/or prophylaxis of atopic dermatitis: the compound (as a free base) appears to reduce inflammation in a pig model which induces an inflammatory skin lesion believed to be generally similar to that which occurs in atopic dermatitis.

The present invention therefore provides 4-{[1-(aminocarbonyl)-4-piperidinyl]amino}-N-[(3,4-dimethylphenyl)methyl]-1-ethyl-1H-pyrazolo[3,4-b]pyridine-5-carboxamide or a salt thereof, in particular a pharmaceutically acceptable salt thereof.

This compound or salt of the present invention is the compound of formula (I):

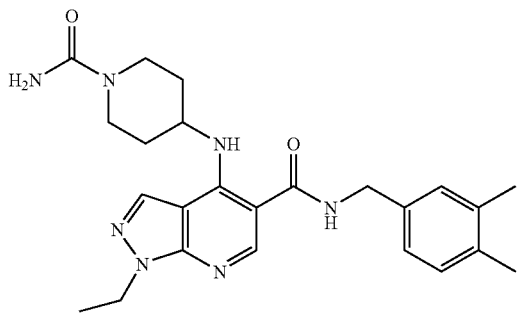

(I)

or a salt thereof, in particular a pharmaceutically acceptable salt thereof.

This compound of formula (I) or salt thereof is a compound of formula (IA) or a salt thereof (in particular, a pharmaceutically acceptable salt thereof):

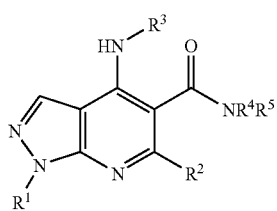

(IA)

wherein:
R$^1$ is ethyl;
R$^2$ is a hydrogen atom (H);
R$^3$ is an N-aminocarbonyl-piperidinyl group of sub-formula (bb) which is not substituted on a ring carbon:

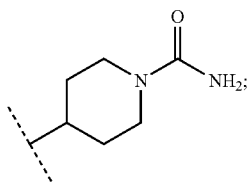

(bb)

R$^4$ is a hydrogen atom (H);
and R$^5$ is (3,4-dimethylphenyl)methyl.

The compound 4-{[1-(aminocarbonyl)-4-piperidinyl]amino}-N-[(3,4-dimethylphenyl)methyl]-1-ethyl-1H-pyrazolo[3,4-b]pyridine-5-carboxamide can alternatively be named 4-{[1-(aminocarbonyl)-4-piperidinyl]amino}-5-{[(3,4-dimethylphenyl)methyl]aminocarbonyl}-1-ethyl-1H-pyrazolo[3,4-b]pyridine.

In a presently-preferred embodiment, the compound of formula (I) or the salt thereof comprises (e.g. consists essentially of, or is) the compound of formula (I). That is, it comprises (e.g. consists essentially of, or is) the "free base" form.

Therefore, in a presently-preferred embodiment, the invention provides 4-{[1-(aminocarbonyl)-4-piperidinyl]amino}-N-[(3,4-dimethylphenyl)methyl]-1-ethyl-1H-pyrazolo[3,4-b]pyridine-5-carboxamide. This is the "free base" form.

Because of their potential use in medicine, the salts of the compound of formula (I) are preferably pharmaceutically acceptable. The pharmaceutically acceptable salt can suitably include (e.g. can consist essentially of, or be) an acid addition salt.

It is believed that a pharmaceutically acceptable acid addition salt can be formed by combination of a compound of formula (I) with a suitable acid (e.g. inorganic or organic acid), for example with a pharmaceutically acceptable acid (e.g. inorganic or organic acid) having a pKa of 2 or less, such as with a pharmaceutically acceptable acid having a pKa of 1.5 or less. For example, it is believed that a pharmaceutically acceptable acid addition salt can be formed by combination of a compound of formula (I) with hydrobromic, hydrochloric, sulfuric, nitric, phosphoric, p-toluenesulfonic, benzenesulfonic, methanesulfonic, ethanesulfonic, or naphthalenesulfonic (such as 2-naphthalenesulfonic) acid. For example, a pharmaceutically acceptable acid addition salt can (it is believed) be formed in a suitable solvent such as an organic solvent or mixed aqueous/organic solvent, to give the salt which is usually isolated, for example by crystallisation and filtration (e.g. on a large scale) or by evaporation (e.g. on a small scale).

For example, it is believed that a pharmaceutically acceptable acid addition salt of the compound of formula (I) can comprise (e.g. can consist essentially of, or be) a hydrobromide, hydrochloride, sulfate, nitrate, phosphate, p-toluenesulfonate, benzenesulfonate, methanesulfonate, ethanesulfonate, or naphthalenesulfonate (e.g. 2-naphthalenesulfonate) salt. The salt can in particular comprise (e.g. can consist essentially of, or be) a hydrochloride salt (e.g. monohydrochloride salt) of the compound of formula (I).

Therefore, in one embodiment, the invention provides a or the hydrochloride salt (e.g. monohydrochloride salt) of the compound of formula (I). That is, in this embodiment the invention provides 4-{[1-(aminocarbonyl)-4-piperidinyl]amino}-N-[(3,4-dimethylphenyl)methyl]-1-ethyl-1H-pyrazolo[3,4-b]pyridine-5-carboxamide hydrochloride (e.g. monohydrochloride).

Other non-pharmaceutically acceptable salts may be used, for example in the isolation of compounds of the invention, and are included within the scope of this invention.

The invention includes within its scope all possible stoichiometric and non-stoichiometric forms of the salts of the compound of formula (I).

Also included within the scope of the invention are all forms of the compound and/or salts of the invention, such as solvates, hydrates and/or complexes.

Certain salts included in the present invention may or may not be present as isomers. The present invention includes within its scope all such isomers, including racemates, enantiomers and mixtures thereof.

Certain of the groups included in compound of formula (I) or its salts may exist in one or more tautomeric forms. The present invention includes within its scope all such tautomeric forms, including mixtures.

The compound or salt of the invention can be present in isolated form and/or in solid form. According to one optional embodiment of the invention, the compound or salt of the invention is present in crystalline form (for example, at least 90% by molarity of the compound or salt being in crystalline form).

The compound of formula (I) has a molecular weight of about [449 to 450]. Molecular weight here refers to that of the unsolvated "free base" compound, that is excluding any molecular weight contributed by any addition salts, solvent (e.g. water) molecules, etc.

Synthetic Process Routes

The following processes can, it is believed, be used to make the compound of formula (I) which is the compound of formula (IA), as hereinbefore defined. $R^1$ is ethyl, $R^2$ is H, and $R^3$ is as defined above, throughout.

Process A

To form the compound of formula (I), which is the compound of formula (IA), a carboxylic acid of formula (II) can be converted into an activated compound of formula (III) wherein $X^1$=a leaving group substitutable by an amine (as defined below) and subsequently the activated compound can be reacted with an amine of formula $NHR^4R^5$:

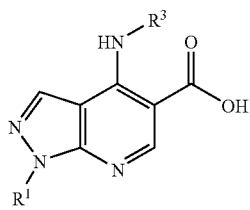

(II)

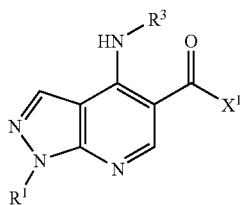

(III)

For example, the activated compound (the compound of formula (III)) can be the acid chloride. This can be formed from the carboxylic acid (II) e.g. by reaction with thionyl chloride, either in an organic solvent such as chloroform or without solvent. Alternatively, the activated compound (the compound of formula (III)) can be an activated ester wherein the leaving group $X^1$ is

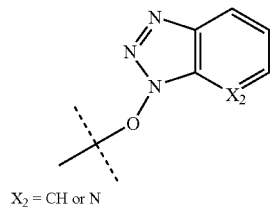

$X_2$ = CH or N

The latter activated compound of formula (III) can be formed from the carboxylic acid (II) either:

(a) by reaction of the carboxylic acid with a carbodiimide such as EDC (1-ethyl-3-(3'-dimethylaminopropyl)carbodiimide), or a salt thereof e.g. hydrochloride salt, preferably followed by reaction of the resulting product with 1-hydroxybenzotriazole (HOBT); reaction (a) being carried out usually in the presence of a solvent (e.g. anhydrous) such as dimethyl formamide (DMF) or acetonitrile and/or usually in the presence of a base, e.g. tertiary organic amine base, such as diisopropylethylamine ($^iPr_2NEt$=DIPEA) and/or usually at room temperature (e.g. about 20 to about 25° C.) and/or for example under anhydrous conditions; or:

(b) by reaction with 2-(1H-benzotriazole-1-yl)-1,1,3,3-tetramethyluronium tetrafluoroborate (TBTU) or O-(7-azabenzotriazol-1-yl)-N,N,N',N'-tetramethyluronium hexafluorophosphate (HATU), in the presence of a base, e.g. tertiary organic amine base, such as diisopropylethylamine ($^iPr_2NEt$=DIPEA), and usually in the presence of a solvent such as dimethyl formamide (DMF) or acetonitrile and/or for example under anhydrous conditions and/or usually at room temperature (e.g. about 20 to about 25° C.).

Compounds of formula (II) can be prepared by hydrolysis of an ester of formula (IV), wherein $R^7$ is alkyl such as $C_{1-4}$alkyl e.g. methyl or ethyl. This procedure can for example involve reaction of (IV) with either:

(a) a base, e.g. alkali metal hydroxide such as sodium hydroxide, potassium hydroxide or lithium hydroxide, in a solvent e.g. an aqueous solvent (e.g. aqueous solvent comprising a mixture of water and a water-miscible organic solvent) such as aqueous ethanol or aqueous dioxane, or (b) an acid such as hydrochloric acid in a solvent e.g. an aqueous solvent such as aqueous dioxane:

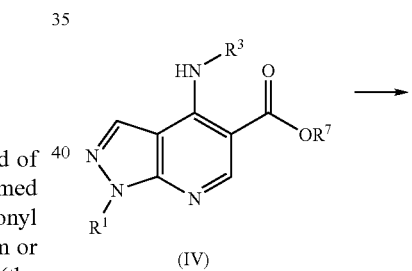

(IV)

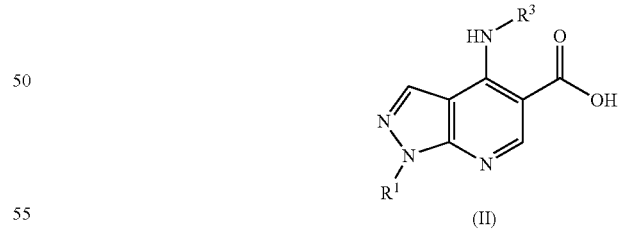

(II)

The invention also provides in one aspect a compound of formula (II), and in another aspect a compound of formula (IV), as defined herein.

The compound of formula (IV) can be prepared by reacting a compound of formula (IVa) or a salt thereof (e.g. hydrochloride salt thereof) with a urea-forming reagent capable of converting the (4-piperidinyl)amino group in the compound of formula (IVa) into a [(1-aminocarbonyl)-4-piperidinyl]amino group:

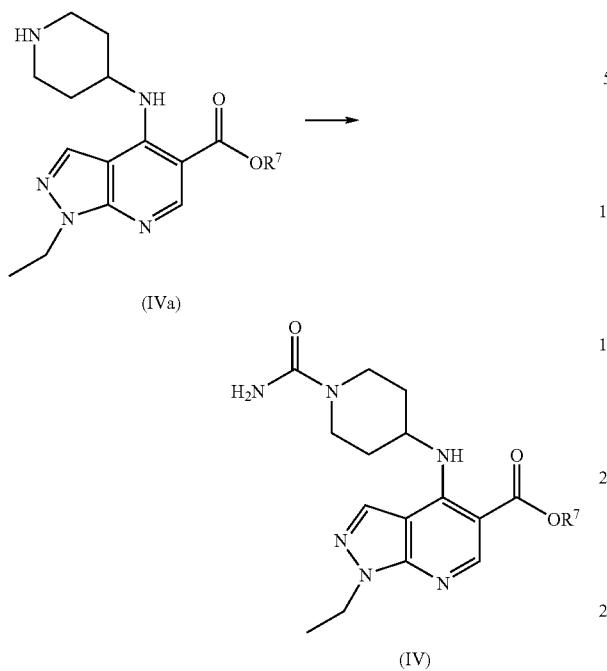

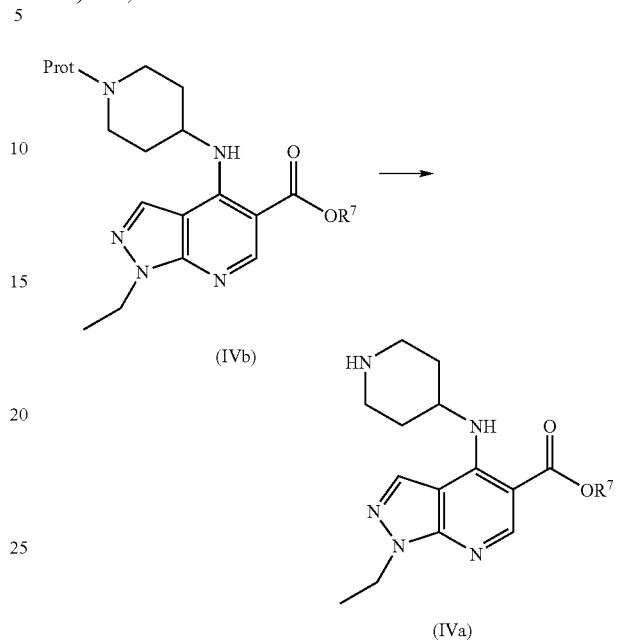

such as (tert-butyloxy)carbonyl (Boc), by deprotection of the nitrogen protecting group. Boc removal can be effected by suitable acidic conditions, such as hydrogen chloride (e.g. 4M) in 1,4-dioxane:

The urea-forming reagent may be benzyl isocyanate (followed later by debenzylation e.g. reductive debenzylation), or preferably the urea-forming reagent is tri($C_{1-4}$alkyl)silyl isocyanate such as a tri($C_{1-2}$alkyl)silyl isocyanate, preferably trimethylsilyl isocyanate. The reaction of the compound (IVa) or salt thereof to the compound (IV) can be carried out in the presence of a base such as N,N-diisopropylethylamine ($^i$Pr$_2$NEt=DIPEA), for example in more than one mole equivalent compared to the number of moles of (IVa) or salt. The reaction is optionally carried out at room temperature or by heating at reflux.

The reaction of the compound (IVa) or salt thereof to compound (IV) can be carried out in an organic solvent, the solvent preferably not being an aqueous-organic solvent system or mixture. The organic solvent can optionally be tetrahydrofuran (THF). However, although THF appears at first sight to work satisfactorily on an about 4 g scale (see Intermediate 4, $R^7$=ethyl, HCl salt of (IVa)), it appears at first sight that the yield might decrease when the reaction scaled up e.g. to about 33.5 g (see first half of Intermediate 4A, $R^7$=ethyl, HCl salt of (IVa)). It seems that the solubility of the HCl salt of (IVa) in THF is limited. Therefore, preferably the reaction of compound (IVa) or salt to compound (IV) is carried out in a solubilising organic solvent comprising (e.g. consisting essentially of or being) an organic solvent capable of dissolving the compound of formula (IVa) or salt thereof (whichever is used) to a substantially greater extent than THF. For example, the solubilising organic solvent can be dichloromethane (e.g. at room temperature or at reflux temperature) or (probably) chloroform. Dichloromethane appears to work satisfactorily on a scale of about 33.5 g, for $R^7$=ethyl and using the HCl salt of compound (IVa) (see e.g. second half of Intermediate 4A). (See also Intermediate 4B). In the reaction, the compound (IVa) or salt thereof is preferably substantially wholly in solution, rather than being at least partly in suspension, in the organic solvent.

Compound (IVa) or the salt thereof can be prepared from compound (IVb), wherein Prot is a nitrogen protecting group Compound (IVb), wherein $R^7$ is ethyl and Prot is Boc, can be prepared according to a method, for example as described in Intermediate 2 or 2A herein, by reaction of a compound of formula (V) (illustrated below wherein $R^7$=ethyl) with 1,1-dimethylethyl 4-amino-1-piperidinecarboxylate (e.g. commercially available from AstaTech, Philadelphia, USA). The reaction is optionally carried out in the presence of a base such as triethylamine or N,N-diisopropylethylamine (DIPEA), and/or in an organic solvent such as acetonitrile. The reaction may require heating e.g. to ca. 60-100° C. (e.g. ca. 80-90° C.), for example for about 16-18 hours:

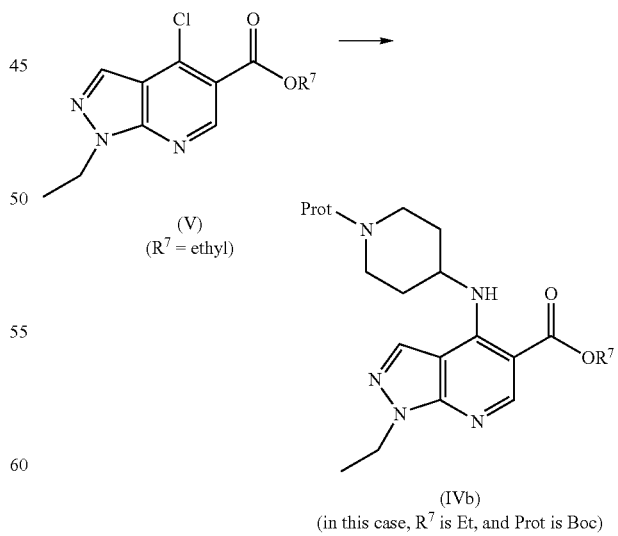

For one preparation of the compound of formula (V) wherein $R^7$ is ethyl, see e.g. Intermediate 1 herein, and/or see Scheme 1 and compound 12 in G. Yu et. al., *J. Med. Chem.*, 2001, 44, 1025-1027. Therefore, a compound of formula (V) can be prepared by reaction of a compound of formula (VI) with, for example, diethyl ethoxymethylene malonate (where $R^7$=Et) with heating, followed by reaction with phosphorous oxychloride, again with heating (see for example Intermediate 1 hereinafter):

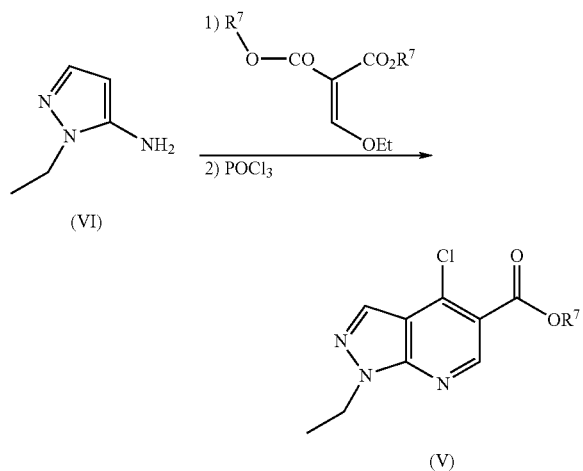

(VI)

(V)

According to one alternative optional embodiment of Process A, a compound of formula (IV), wherein $R^7$ is alkyl such as $C_{1-4}$alkyl e.g. methyl or ethyl, is optionally prepared according to a method, for example as described in Scheme 1 of Yu et. al., *J. Med Chem.*, 2001, 44, 1025-1027, by reaction of a compound of formula (V) with an amine of formula $R^3NH_2$. The reaction is optionally carried out in the presence of a base such as triethylamine or N,N-diisopropylethylamine, and/or in an organic solvent such as ethanol, dioxane or acetonitrile. The reaction may require heating e.g. to ca. 60-100° C., for example ca. 80-90° C.:

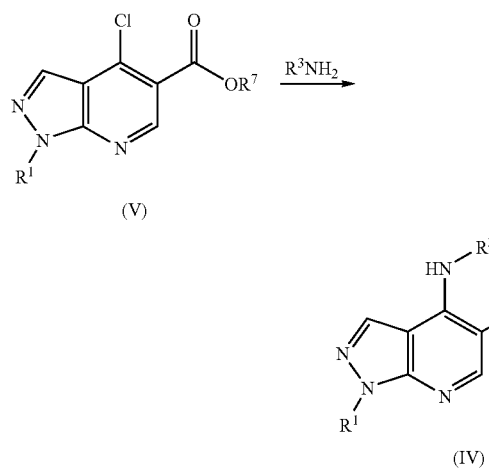

In another alternative embodiment of Process A, the 4-chloro substituent in the compound of formula (V) can be replaced by a bromine or iodine atom, or by another suitable leaving group which is displaceable by an amine of formula $R^3NH_2$. The leaving group can, for example, be an alkoxy group —$OR_{35}$ such as —$OC_{1-4}$alkyl (in particular —OEt) or a group —O—S(O)$_2$—$R^{37}$, wherein $R^{37}$ is $C_{1-8}$alkyl (e.g. $C_{1-4}$alkyl or $C_{1-2}$alkyl such as methyl), $C_{1-6}$fluoroalkyl (e.g. $C_{1-4}$fluoroalkyl or $C_{1-2}$fluoroalkyl such as $CF_3$ or $C_4F_9$), or phenyl wherein the phenyl is optionally substituted by one or two of independently $C_{1-2}$alkyl, halogen or $C_{1-2}$alkoxy (such as phenyl or 4-methyl-phenyl). The reaction may be carried out with or without solvent and may require heating.

Process B

The compound of formula (I), which is the compound of formula (IA), can be prepared by reaction of a compound of formula (VII) with an amine of formula $R^3NH_2$ or a salt (e.g. HCl salt) thereof. The reaction is preferably carried out in the presence of a base, e.g. tertiary organic amine base, such as triethylamine or N,N-diisopropylethylamine (DIPEA), and/or in an organic solvent such as ethanol, tetrahydrofuran (THF), dioxane or acetonitrile. The reaction may require heating, e.g. to ca. 60-100° C. or ca. 80-90° C., for example for 8-72 or 12-48 or 24-48 hours (see e.g. Example 1A herein):

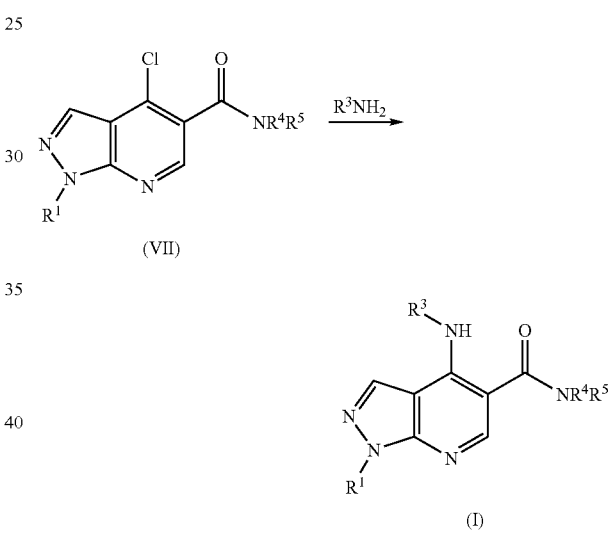

For an example of a preparation of the HCl salt of the amine of formula $R^3NH_2$ (4-amino-1-piperidinecarboxamide hydrochloride), see Intermediates 9 and 10 herein.

Compounds of formula (VII) can be prepared in a two step procedure (e.g. see Bare et. al. in *J. Med. Chem.* 1989, 32, 2561-2573). This process involves, first, reaction of a compound of formula (VIII) with thionyl chloride (or another agent suitable for forming an acid chloride from a carboxylic acid), either in an organic solvent such as chloroform or THF, or as a neat solution, preferably under substantially anhydrous conditions (e.g. under a nitrogen or argon atmosphere). This reaction may require heating (e.g. to reflux). The thus-formed acid chloride intermediate may or may not be isolated. Step two involves reaction of the resulting acid chloride intermediate with an amine of formula $R^4R^5NH$, in an organic solvent such as THF or chloroform and may also involve the use of a base such as triethylamine or diisopropylethylamine (DIPEA). See for example Intermediates 7 and 8 herein:

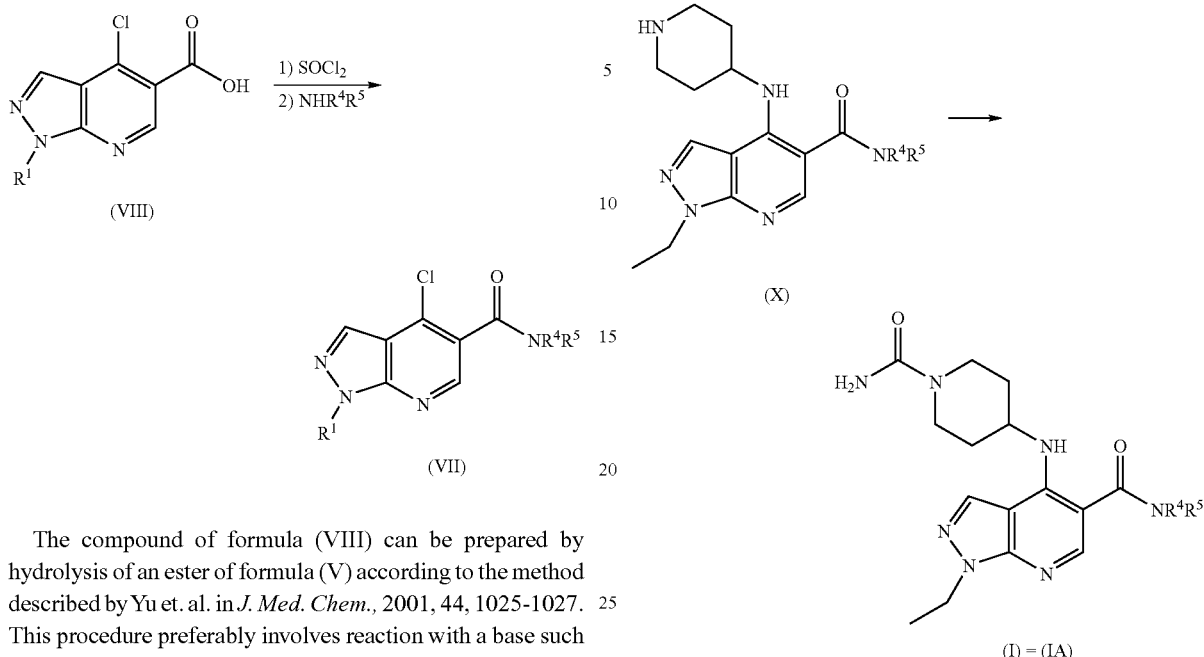

The compound of formula (VIII) can be prepared by hydrolysis of an ester of formula (V) according to the method described by Yu et. al. in *J. Med. Chem.*, 2001, 44, 1025-1027. This procedure preferably involves reaction with a base such as sodium hydroxide or potassium hydroxide in a solvent e.g. an aqueous solvent such as aqueous ethanol or aqueous dioxane:

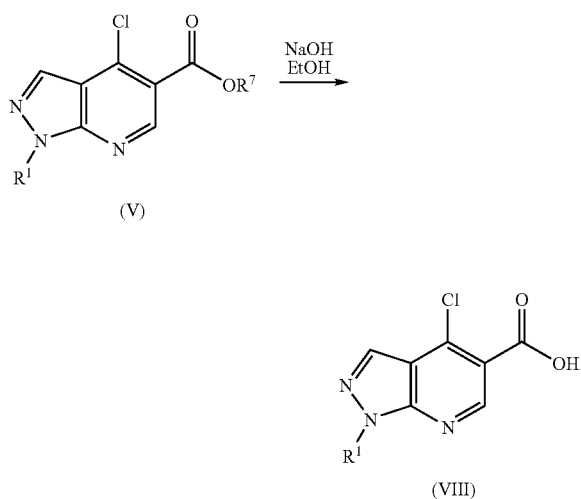

In an alternative embodiment of Process B, the 4-chloro substituent in the compound of formula (VII) can be replaced by a bromine or iodine atom.

Process C

It seems likely that the compound of formula (I)=(IA) can alternatively be prepared by reacting a compound of formula (X) or a salt thereof (e.g. hydrochloride salt thereof) with a urea-forming reagent capable of converting the (4-piperidinyl)amino group in the compound of formula (X) into a [(1-aminocarbonyl)-4-piperidinyl]amino group:

The urea-forming reagent is optionally benzyl isocyanate (followed later by debenzylation e.g. reductive debenzylation) or a tri($C_{1-4}$alkyl)silyl isocyanate such as a tri($C_{1-2}$alkyl) silyl isocyanate, preferably trimethylsilyl isocyanate.

Optionally, the reaction of the compound (X) or salt thereof to the compound (I)=(IA) is carried out in the presence of a tertiary organic amine base such as triethylamine or N,N-diisopropylethylamine ($^{i}Pr_2NEt$=DIPEA), for example in more than one mole equivalent of the base compared to the number of moles of (X) or salt. The reaction is optionally carried out at room temperature or at solvent-reflux temperature. Optionally, the reaction of the compound (X) or salt thereof to compound (I)=(IA) is carried out in an organic solvent, for example a solvent not being an aqueous-organic solvent system or mixture, e.g. an organic solvent such as dichloromethane (e.g. at reflux) or chloroform.

Compound (X) or the salt thereof is optionally prepared from compound of formula (XI), wherein Prot is a nitrogen protecting group such as (tert-butyloxy)carbonyl (Boc), by deprotection of the nitrogen protecting group. Boc removal can be effected by suitable acidic conditions, such as hydrogen chloride (e.g. 4M) in 1,4-dioxane:

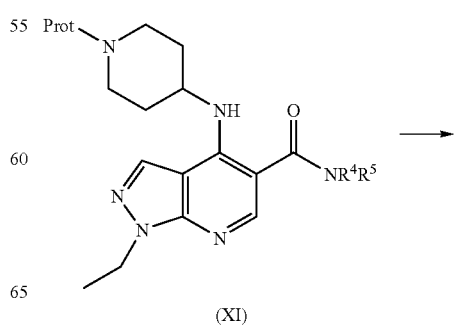

-continued

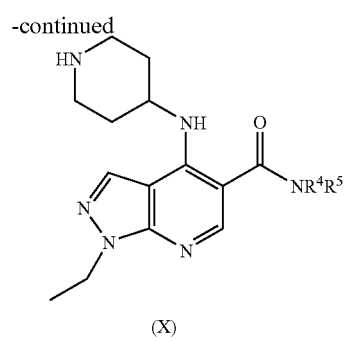

(X)

The compound of formula (XI), wherein Prot is (tert-butyloxy)carbonyl (Boc), is optionally prepared by reaction of a compound of formula (VII) with 1,1-dimethylethyl 4-amino-1-piperidinecarboxylate. The reaction is optionally carried out in the presence of DIPEA, and/or in acetonitrile solvent and/or under heating to ca. 60-100° C. (e.g. ca. 80-90° C.), for example for about 16-18 hours:

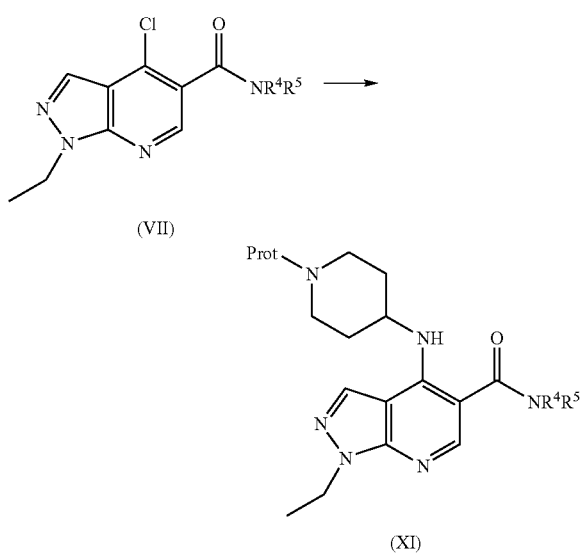

Alternatively, compound (XI) is optionally prepared from the corresponding 5-ester, compound (IVb), illustrated above, e.g. via the corresponding 5-carboxylic acid.

The present invention therefore also provides a method of preparing a compound of formula (I), which is formula (IA), or a salt thereof:

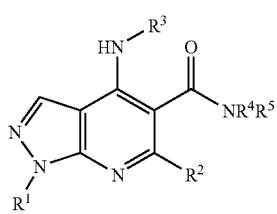

(IA)

wherein $R^1$, $R^2$, $R^3$, $R^4$ and $R^5$ are as defined herein, the method comprising:

(a) converting a compound of formula (II) into an activated compound of formula (III) wherein $X^1$=a leaving group substitutable by an amine:

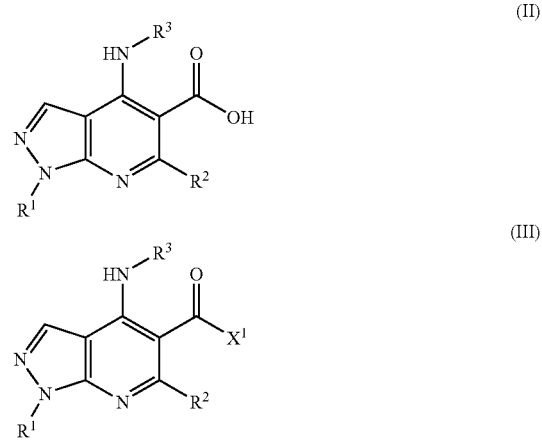

and subsequently reacting the activated compound of formula (III) with an amine of formula $R^4R^5NH$; or (b) reacting a compound of formula (VIIA):

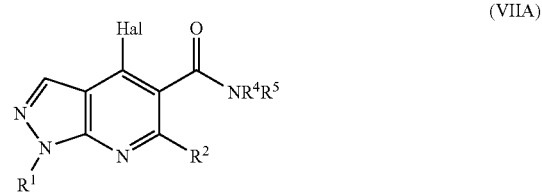

wherein Hal is a chlorine, bromine or iodine atom (such as a bromine atom or preferably a chlorine atom), with an amine of formula $R^3NH_2$ or a salt thereof; or (c) reacting a compound of formula (X) or a salt thereof (e.g. hydrochloride salt thereof):

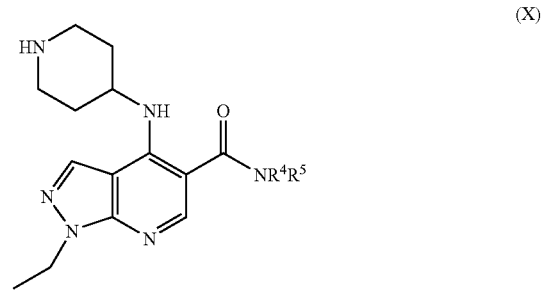

with a urea-forming reagent capable of converting the (4-piperidinyl)amino group in the compound of formula (X) into a [(1-aminocarbonyl)-4-piperidinyl]amino group; and, in the case of (a), (b) or (c), optionally converting the compound of formula (I) into a salt thereof e.g. a pharmaceutically acceptable salt thereof.

The present invention also provides: (g) a method of preparing a pharmaceutically acceptable salt of a compound of formula (I) comprising conversion of the compound of formula (I) or a salt thereof into the desired pharmaceutically acceptable salt thereof.

The present invention also provides a compound of formula (I) or a salt thereof, prepared by a method as defined herein.

In compounds usable in the above synthetic processes, an "alkyl" group or moiety may be straight-chain or branched. Alkyl groups, for example $C_{1-8}$alkyl or $C_{1-6}$alkyl or $C_{1-4}$alkyl or $C_{1-3}$alkyl or $C_{1-2}$alkyl, which may be employed include $C_{1-6}$alkyl or $C_{1-4}$alkyl or $C_{1-3}$alkyl or $C_{1-2}$alkyl such as methyl, ethyl, n-propyl, n-butyl, n-pentyl, or n-hexyl or any branched isomers thereof such as isopropyl, t-butyl, sec-butyl, isobutyl, 3-methylbutan-2-yl, 2-ethylbutan-1-yl, or the like.

A corresponding meaning is intended for "alkoxy", "alkylene", and like terms derived from alkyl. For example, "alkoxy" such as $C_{1-6}$alkoxy or $C_{1-4}$alkoxy or $C_{1-2}$alkoxy includes methoxy, ethoxy, propyloxy, and oxy derivatives of the alkyls listed above. "Alkylsulfonyl" such as $C_{1-4}$alkylsulfonyl includes methylsulfonyl (methanesulfonyl), ethanesulfonyl, and others derived from the alkyls listed above. "Alkylsulfonyloxy" such as $C_{1-4}$alkylsulfonyloxy includes methanesulfonyloxy (methylsulfonyloxy), ethanesulfonyloxy, et al.

"Fluoroalkyl" includes alkyl groups with one, two, three, four, five or more fluorine substituents, for example $C_{1-4}$fluoroalkyl or $C_{1-3}$fluoroalkyl or $C_{1-2}$fluoroalkyl such as monofluoromethyl, difluoromethyl, trifluoromethyl, pentafluoroethyl, 2,2,2-trifluoroethyl ($CF_3CH_2$—), 2,2-difluoroethyl ($CHF_2CH_2$—), 2-fluoroethyl ($CH_2FCH_2$—), etc. "Fluoroalkoxy" includes $C_{1-4}$fluoroalkoxy or $C_{1-2}$fluoroalkoxy such as trifluoromethoxy, pentafluoroethoxy, monofluoromethoxy, difluoromethoxy, etc. "Fluoroalkylsulfonyl" such as $C_{1-4}$fluoroalkylsulfonyl includes trifluoromethanesulfonyl, pentafluoroethylsulfonyl, etc.

A halogen atom ("halo") present in compounds means a fluorine, chlorine, bromine or iodine atom ("fluoro", "chloro", "bromo" or "iodo"), in particular chloro, bromo or iodo.

When the specification states that atom or moiety A is "bonded" or "attached" to atom or moiety B, it means that atom/moiety A is directly bonded to atom/moiety B usually by means of a covalent bond or a double covalent bond, and excludes A being indirectly attached to B via one or more intermediate atoms/moieties (e.g. excludes A-C-B); unless it is clear from the context that another meaning is intended.

Medical Uses

The present invention also provides a compound of formula (I) or a pharmaceutically acceptable salt thereof for use as an active therapeutic substance in a mammal such as a human. The compound or salt can be for use in the treatment and/or prophylaxis of any of the diseases/conditions described herein (e.g. for use in the treatment and/or prophylaxis of an inflammatory and/or allergic disease in a mammal such as a human; or e.g. for use in the treatment and/or prophylaxis of cognitive impairment or depression in a mammal such as a human); and/or can be for use as a phosphodiesterase 4 (PDE4) inhibitor. "Therapy" may include treatment and/or prophylaxis.

The compound or salt can for example be for use in the treatment and/or prophylaxis of an inflammatory and/or allergic skin disease, such as atopic dermatitis or psoriasis, in a mammal such as a human.

Also provided is the use of a compound of formula (I) or a pharmaceutically acceptable salt thereof in the manufacture of a medicament (e.g. pharmaceutical composition) for the treatment and/or prophylaxis of any of the diseases/conditions described herein in a mammal such as a human, e.g. for the treatment and/or prophylaxis of an inflammatory and/or allergic disease in a mammal such as a human, or e.g. for the treatment and/or prophylaxis of cognitive impairment or depression in a mammal.

Also provided is a method of treatment and/or prophylaxis of any of the diseases/conditions described herein in a mammal (e.g. human) in need thereof, e.g. a method of treatment and/or prophylaxis of an inflammatory and/or allergic disease, cognitive impairment or depression in a mammal (e.g. human) in need thereof, which method comprises administering to the mammal (e.g. human) a therapeutically effective amount of a compound of formula (I) as herein defined or a pharmaceutically acceptable salt thereof.

Phosphodiesterase 4 inhibitors are thought to be useful in the treatment and/or prophylaxis of a variety of diseases/conditions, especially inflammatory and/or allergic diseases, in mammals such as humans, for example: asthma, chronic obstructive pulmonary disease (COPD) (e.g. chronic bronchitis and/or emphysema), atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock, adult respiratory distress syndrome, multiple sclerosis, cognitive impairment (e.g. in a neurological disorder such as Alzheimer's disease), depression, or pain (e.g. inflammatory pain). Ulcerative colitis and/or Crohn's disease are collectively often referred to as inflammatory bowel disease.

In the treatment and/or prophylaxis, the inflammatory and/or allergic disease is preferably chronic obstructive pulmonary disease (COPD), asthma, rheumatoid arthritis, allergic rhinitis, psoriasis or atopic dermatitis in a mammal (e.g. human). More preferably, the treatment and/or prophylaxis is of COPD, psoriasis or atopic dermatitis in a mammal (e.g. human).

Most preferably, the treatment and/or prophylaxis is of atopic dermatitis in a mammal such as a human or pig, preferably in a human, in particular in a human aged 21 years or less, e.g. 18 years or less. For treatment and/or prophylaxis of atopic dermatitis in a mammal, external topical administration to the mammal of the compound of formula (I) or a pharmaceutically acceptable salt thereof (e.g. topical administration to the skin e,g. to skin affected by the atopic dermatitis) is preferably used. For treatment and/or prophylaxis of atopic dermatitis, inhaled administration is usually not suitable.

"Atopic dermatitis" has been proposed to include two general sub-classes: (1) an "allergic (extrinsic)" type of atopic dermatitis which generally occurs in the context of sensitization to environmental allergens and/or which is generally accompanied by elevated serum IgE levels; and (2) an "non-allergic (intrinsic)" type of atopic dermatitis generally with little or no detectable sensitization and/or generally with normal or low serum IgE levels (N. Novak et al., *J. Allergy Clin. Immunol*, 2003, 112, 252-262; and T. C. Roos et al., *Drugs*, 2004, 64(23), 2639-2666, see e.g. pages 2640-2641). The compound of formula (I) or the pharmaceutically acceptable salt thereof can therefore be for the treatment and/or prophylaxis of allergic (extrinsic) atopic dermatitis and/or non-allergic (intrinsic) atopic dermatitis in a mammal (e.g. human or pig, preferably human).

"External topical" administration means topical administration to an external body part (i.e. excluding, for example, the lung or mouth, but including the lips), preferably excluding the eye.

"External topical" administration preferably is topical administration to the skin, for example to the skin of an arm, hand, leg, foot, head (e.g. face), neck and/or torso of a mammal such as a human. External topical administration can for example be to those parts of a mammal's skin affected by or susceptible to atopic dermatitis.

For the use of PDE4 inhibitors in atopic dermatitis, see for example:

J. M. Hanifin et al., "Type 4 phosphodiesterase inhibitors have clinical and in vitro anti-inflammatory effects in atopic dermatitis", *J. Invest. Dermatol.*, 1996, 107(1), 51-56; which reports reductions of inflammatory parameters in atopic dermatitis patients treated with PDE4 inhibitor CP80,633 (0.5% ointment, twice daily topical application);

C. E. M. Griffiths et al., "Randomized comparison of the type 4 phosphodiesterase inhibitor cipamfylline cream, cream vehicle and hydrocortisone 17-butyrate cream for the treatment of atopic dermatitis", *Br. J. Dermatol.*, 2002, 147(2), 299-307, which reports that cipamfylline (0.15%) cream is significantly more effective than vehicle, but significantly less effective than hydrocortisone 17-butyrate (0.1%) cream, in the treatment of atopic dermatitis patients;

T. C. Roos et al., "Recent advances in treatment strategies for atopic dermatitis", *Drugs*, 2004, 64(23), 2639-2666 (see e.g. page 2657 and refs. 201-209 therein);

A. M. Doherty, *Current Opinion Chem. Biol.*, 1999, 3(4), 466-473 (e.g. see p. 470); and H. J. Dyke et al., *Expert Opinion Invest. Drugs*, 2002, 11(1), 1-13 (e.g. see p. 7 and refs. 74, 75 and 76 cited therein);

and references cited in the above references.

For the use of the PDE4 inhibitors SB 207499 (cilomilast) and AWD 12-281 in mouse models of the allergic type of dermatitis, see W. Bäumer et al., *Eur. J. Pharmacol.*, 2002, 446, 195-200 and W. Bäumer et al., *J. Pharmacy Pharmacol.*, 2003, 55, 1107-1114.

PDE4 inhibitors are thought to be effective in the treatment of COPD. For example, see S. L. Wolda, *Emerging Drugs*, 2000, 5(3), 309-319; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; A. M. Vignola, *Respiratory Medicine*, 2004, 98, 495-503; D. Spina, *Drugs*, 2003, 63(23), 2575-2594; and references cited in the aforementioned publications; and G. Krishna et al., *Expert Opinion on Investigational Drugs*, 2004, 13(3), 255-267 (see especially pp. 259-261 and refs. 102-111 and 201 therein).

The PDE4 inhibitor cilomilast (Ariflo™) at 15 mg orally twice daily appears to improve forced expiratory volume in 1s (FEV$_1$) in COPD patients (C. H. Compton et al., *The Lancet*, 2001, vol. 358, 265-270), and appears to have antiinflammatory effects in COPD patients (E. Gamble et al., *Am. J. Respir. Crit. Care Med.*, 2003, 168, 976-982). On cilomilast, see also R. D. Border et al., *Chest*, 2003, vol. 124 Suppl. 4, p. 170S (abstract) and J. D. Eddleston et al., *Am. J. Respir. Crit. Care Med.*, 2001, 163, A277 (abstract). The PDE4 inhibitor roflumilast appears to show small improvements in FEV$_1$ in COPD patients (see B. J. Lipworth, *The Lancet*, 2005, 365, 167-175, and refs 49-50 therein).

COPD is often characterised by the presence of airflow obstruction due to chronic bronchitis and/or emphysema (e.g., see S. L. Wolda, *Emerging Drugs*, 2000, 5(3), 309-319).

PDE4 inhibitors are thought to be effective in the treatment of asthma (e.g. see M. A. Giembycz, *Drugs*, February 2000, 59(2), 193-212; Z. Huang et al., *Current Opinion in Chemical Biology*, 2001, 5: 432-438; H. J. Dyke et al., *Expert Opinion on Investigational Drugs*, January 2002, 11(1), 1-13; C. Burnouf et al., *Current Pharmaceutical Design*, 2002, 8(14), 1255-1296; A. M. Doherty, *Current Opinion Chem. Biol.*, 1999, 3(4), 466-473; P. J. Barnes, *Nature Reviews—Drug Discovery*, October 2004, 831-844; and references cited in the aforementioned publications).

PDE4 inhibitors are thought to be effective in the treatment of allergic rhinitis (e.g. see B. M. Schmidt et al., *J. Allergy & Clinical Immunology*, 108(4), 2001, 530-536).

PDE4 inhibitors are thought to be effective in the treatment of rheumatoid arthritis and multiple sclerosis (e.g. see H. J. Dyke et al., *Expert Opinion on Investigational Drugs*, January 2002, 11(1), 1-13; C. Burnouf et al., *Current Pharmaceutical Design*, 2002, 8(14), 1255-1296; and A. M. Doherty, *Current Opinion Chem. Biol.*, 1999, 3(4), 466-473; and references cited in these publications).

PDE4 inhibitors have been suggested as having analgesic properties and thus being effective in the treatment of pain (A. Kumar et al., *Indian J. Exp. Biol.*, 2000, 38(1), 26-30).

In the invention, the treatment and/or prophylaxis can be of cognitive impairment e.g. cognitive impairment in a neurological disorder such as Alzheimer's disease. For example, the treatment and/or prophylaxis can comprise cognitive enhancement e.g. in a neurological disorder. See for example: H. T. Zhang et al. in: *Psychopharmacology*, June 2000, 150 (3), 311-316 and *Neuropsychopharmacology*, 2000, 23(2), 198-204; and T. Egawa et al., *Japanese J. Pharmacol.*, 1997, 75(3), 275-81.

PDE4 inhibitors such as rolipram have been suggested as having antidepressant properties (e.g. J. Zhu et al., *CNS Drug Reviews*, 2001, 7(4), 387-398; O'Donnell, *Expert Opinion on Investigational Drugs*, 2000, 9(3), 621-625; and H. T. Zhang et al., *Neuropsychopharmacology*, October 2002, 27(4), 587-595; J. M. O'Donnell and H.-T. Zhang, *Trends Pharmacol. Sci.*, March 2004, 25(3), 158-163; and T. E. Renau, *Curr. Opinion Invest. Drugs*, 2004, 5(1), 34-39).

PDE4 inhibition has been suggested for the treatment of inflammatory bowel disease (e.g. ulcerative colitis and/or Crohn's disease), see K. H. Banner and M. A. Trevethick, *Trends Pharmacol. Sci.*, August 2004, 25(8), 430-436.

Pharmaceutical Compositions, Routes of Administration, and Dosing

For use in medicine, the compound or salt of the present invention is suitably administered as a pharmaceutical composition.

The present invention therefore provides in a further aspect a pharmaceutical composition comprising a compound of formula (I) or a pharmaceutically acceptable salt thereof and one or more pharmaceutically acceptable carriers and/or excipients.

The pharmaceutical composition can be for use in the treatment and/or prophylaxis of any of the conditions described herein, in particular atopic dermatitis in a mammal such as a human.

The invention also provides a method of preparing a pharmaceutical composition comprising a compound of formula (I), as herein defined, or a pharmaceutically acceptable salt thereof, and one or more pharmaceutically acceptable carriers and/or excipients, the method comprising mixing the compound or salt with the one or more pharmaceutically acceptable carriers and/or excipients.

The invention also provides a pharmaceutical composition prepared by said method.

The compounds of formula (I) and/or the pharmaceutical composition may be administered, for example, by external topical (e.g. skin topical), parenteral (e.g. intravenous, subcutaneous, or intramuscular), inhaled or nasal administration.

Accordingly, the pharmaceutical composition can be suitable for (e.g. adapted for) external topical (e.g. skin topical), parenteral (e.g. intravenous, subcutaneous, or intramuscular), inhaled or nasal administration. The pharmaceutical composition is preferably suitable for inhaled administration or more preferably is suitable for external topical (e.g. skin topical) administration, e.g. to a mammal such as a human. Inhaled administration involves topical administration to the lung e.g. by aerosol or dry powder composition.

Although the compound of formula (I) or salt thereof may be administered orally, oral administration is not presently thought to be a preferred route of administration. This is because, without intending to be bound by this data, preliminary tests appear to indicate a low systemic exposure after oral administration of the compound of formula (I) ("free base" form) to rat(s), at a dose level of about 1 mg of the compound per kg bodyweight, when formulated in approximately [10% DMSO and 90% PEG200/water (70:30 PEG200:water ratio)].

The pharmaceutical composition can optionally be in unit dose form. The unit dose form can for example be: (a) a rupturable or peel-openable sealed dose container containing a dry powder inhalable pharmaceutical composition (e.g. a plurality of which are usually disposed inside a suitable inhalation device); (b) a vial, ampoule or filled syringe for parenteral administration e.g. comprising a solution or suspension of the compound or pharmaceutically acceptable salt in a suitable carrier such as an aqueous carrier or e.g. containing a lyophilised parenteral pharmaceutical composition (the vial or ampoule can optionally be manufactured using a blow-fill-seal process); or (c) (less preferred) a tablet or capsule for oral administration e.g. for oral administration to a human.

Alternatively, the composition can be in a form adapted for the administration of varying amounts of composition as desired by the user, such as a spreadable or sprayable external topical composition such as a cream, an ointment, a gel, or a liquid.

Pharmaceutical Compositions Suitable for External Topical Administration

The pharmaceutical composition of the invention is preferably suitable for (e.g. adapted for) external topical (e.g. skin topical) administration, for example to a mammal such as a human. More preferably, the pharmaceutical composition suitable for external topical administration is for the treatment and/or prophylaxis of atopic dermatitis in a mammal such as a human.

"External topical administration" is defined above under the "medical uses" section. External topical administration can for example be to those parts of the skin affected by or susceptible to the disease or condition e.g. atopic dermatitis, in particular in a mammal (e.g. human) suffering from or susceptible to atopic dermatitis.

An external-topical pharmaceutical composition, e.g. skin topical pharmaceutical composition, can for example be an ointment, a cream (usually an oil-in-water or water-in-oil pharmaceutical composition, usually an emulsion), an aqueous gel, or a microemulsion. The pharmaceutical composition can alternatively be a DMSO-containing solution such as a DMSO/acetone solution or DMSO/water solution (DMSO=dimethyl sulfoxide); a DMSO-containing solution can be used for experimental animal tests, but is not usually desirable for use in humans.

In the external-topical pharmaceutical composition, e.g. an ointment or an oil-in-water or water-in-oil composition, the compound of formula (I) or the pharmaceutically acceptable salt thereof is suitably present in 0.05% to 10%, preferably 0.1% to 5%, more preferably 0.1% to 3%, still more preferably 0.2% to 3% (e.g. about 0.5% or about 2.5%), yet more preferably 0.2% to 1.5% (e.g. about 0.5%), by weight of the composition (w/w).

In one optional embodiment, the compound of formula (I) or the pharmaceutically acceptable salt thereof can optionally be in a particle-size-reduced form, for example obtained or obtainable by micronisation. This can be, for example, for use in a pharmaceutical composition suitable for (e.g. adapted for) external topical (e.g. skin topical) administration. See the Particle size reduction sub-section below, within the Inhalable pharmaceutical compositions section, for more details.

Aqueous solubility: A preliminary screen aims to estimate roughly the aqueous solubility of compounds by (as an approximate summary): (i) creating a ca. 10 mM solution of the compound in DMSO, (ii) diluting a portion of this DMSO solution by mixing about 19 parts by volume of pH 7.4 aqueous phosphate buffered saline (PBS) buffer with 1 part by volume of the ca. 10 mM DMSO solution, (iii) "filtering" the mixture with the aid of centrifugation, and then (iv) measuring the concentration of the dissolved compound in the "filtrate". Although some DMSO (about 5% by volume) is present in this solubility screen "filtrate", the results from this preliminary screen (about 60 micrograms of compound (I)/ml) appear to suggest generally that the compound of formula (I) (in the "free base" form) has a generally moderate aqueous solubility at about room temperature.

Lipophilicity: The compound of formula (I) (as the free base) is thought to have a clogP (calculated log of the octanol/water partition coeficient (P)) of approximately 2.5, suggesting moderate lipophilicity. The compound of formula (I) (as the free base) is believed to have a measured logD (D=distribution coefficient, wherein log D is generally log P corrected for ionization) of approximately 3.4 at pH=7.4, again suggesting modest/moderate lipophilicity.

Solubilising and/or skin-penetration-enhancing agents: An external-topical pharmaceutical composition, e.g. an ointment or an oil-in-water cream or water-in-oil cream, preferably includes an agent which acts as a skin-penetration enhancer for and/or a solubiliser of the compound of formula (I) or the salt thereof. The skin-penetration-enhancing- and/or solubilising-agent can for example be propylene glycol, diethylene glycol monoethyl ether (e.g. TRANSCUTOL™) and/or caprylocaproyl macrogolglycerides (e.g. LABRASOL™), preferably propylene glycol. The solubiliser and/or skin-penetration enhancer suitably does not comprise DMSO. The solubiliser and/or skin-penetration enhancer is preferably both a solubiliser and skin-penetration enhancer, and/or is suitably present in 0.5% to 50%, preferably 5% to 50%, more preferably 7% to 30%, still more preferably 7% to 25%, yet more preferably about 10% to about 20% (e.g. about 10% or about 20%), by weight of the composition (w/w).

The skin-penetration enhancer is for delivery of the compound of formula (I) or salt thereof ("active agent" or "drug") through the skin. Solubilization of the drug also helps. The solubilising and/or skin-penetration-enhancing agents should ideally (a) be safe and/or tolerable, (b) have as low a potential for skin irritancy as possible consistent with being an effective skin penetration enhancer, and (c) be compatibile with the active pharmaceutical ingredient. Note that the agent preferably functions both as a solubilising agent and a skin-penetration-enhancing agent.

Surfactants: An external-topical pharmaceutical composition, e.g. an ointment or an oil-in-water cream or water-in-oil cream, preferably includes a surfactant (e.g. as an emulsifier), for example for achieving emulsification of compositions having two or more phases. The total surfactant content can for example be 0.3% to 20%, e.g. 0.5% to 15% or 0.5% to 12% or 0.5% to 10% or 1% to 12% or 3% to 10%, by weight of the composition (w/w). The surfactant can for example comprise one or more of the following: a polyoxyl $C_{12\text{-}22}$alkyl ether (e.g. a polyoxyl $C_{14\text{-}20}$alkyl ether such as polyoxyl cetyl ether or polyoxyl stearyl ether) (e.g. present at 0.5% to 10% w/w, e.g. 2.5% to 10% w/w such as about 5% to about 8% w/w), glycerol monostearate (e.g. Arlacel 165™) (e.g. present at 0.5% to 10% w/w, e.g. about 2% w/w), sorbitan monostearate (e.g. Span 60™) (e.g. present at 0.05% to 10% w/w, e.g. about 1% w/w), cetyl alcohol and/or stearyl alcohol (e.g. wherein the total of any cetyl alcohol and any stearyl alcohol present is 0.1% to 15% w/w, e.g. 1% to 10% w/w such as about 2% to about 5% w/w), and sodium dodecyl sulphate (SDS) (e.g. present at 0.3% to 2% w/w such as about 1% w/w). Polyoxyl stearyl ether (steareth) can e.g. be polyoxyl 2 stearyl ether (steareth 2) or polyoxyl 21 stearyl ether (steareth 21).

DMSO-containing solutions: One possible external-topical pharmaceutical composition is a solution of the compound of formula (I) or the pharmaceutically acceptable salt thereof present at ca. 0.5% to ca. 2.5% w/w in a DMSO-containing solvent such as in DMSO/acetone or in DMSO/water; for example a solution of the compound or salt present at ca. 0.5% to ca. 2.5% w/w in DMSO/acetone (1:1). DMSO-containing solutions, often being capable of high skin penetration, are often good experimental pre-clinical formulations for use in animals, but their likely skin irritancy generally make them less suitable for use in humans such as patients, e.g. atopic dermatitis patients.

Ointments and creams (and oil phase): An external-topical pharmaceutical composition can be an ointment or an oil-in-water cream or water-in-oil cream. The ointment or cream typically contains an oil phase (oily ointment base). The oil phase (ointment base) typically comprises an oil and/or a fat, preferably of a consistency suitable for skin-spreadability.

Preferably, an oil comprising or being white soft paraffin (white petrolatum) and/or a mineral oil (such as liquid paraffin) can be used. (Mineral oil can also be used as a solubiliser and/or emollient). The white soft paraffin (white petrolatum) can be of various grades, for example (for Penreco supplier) Penreco Regent White grade, Penreco Snow White grade, or Penreco Ultima White grade, in particular high melting point white soft paraffin (e.g. of Penreco Ultima White grade). Microcrystalline wax or beeswax or beeswax substitute can be used as an oil/fat in the oil phase.

Alternatively or additionally, one or more fats like straight or branched chain mono- or di-alkyl esters such as isopropyl myristate, isopropyl palmitate, diisopropyl adipate, isocetyl stearate, isostearyl isostearate, decyl oleate, butyl stearate, 2-ethylhexyl palmitate, propylene glycol diester of coconut fatty acids, or a mixed ester of 2-ethyl hexanoic acid with a blend of cetyl or stearyl alcohols (e.g. known as Crodamol CAP) may be used in the oil phase (some of these are also solubilisers and/or surfactants). These may be used singly or in combination depending on the properties required.

The oil phase (oily ointment base) can for example be present at 25 to 85% w/w (e.g. 50 to 80% w/w) in an ointment (e.g. emulsion or homogeneous single phase), at 25 to 85% w/w (e.g. 35 to 70% w/w) in an water-in-oil cream (e.g. emulsion), or at 8 to 55% w/w (e.g. 10 to 45% w/w) in an water-in-oil cream (e.g. emulsion).

Exemplary ointments: An exemplary external-topical pharmaceutical composition is an ointment comprising:
  the compound of formula (I) or pharmaceutically acceptable salt thereof present at 0.1% to 5% w/w (e.g. 0.1% to 3% w/w or 0.2% to 1.5% w/w);
  an oil phase (oily ointment base) present at 25% to 99% w/w or 25% to 85% w/w or 50% to 80% w/w (for example, the oil phase can comprise white petrolatum present at 25 to 75% w/w or 45 to 75% w/w, and optionally also comprising mineral oil (e.g. as solubiliser and emollient) present at 2.5% to 15% w/w such as 4% to 12% w/w);
  one or more surfactants (e.g. polyoxyl stearyl ether) present in total at 0.5% to 10% w/w or 3% to 10% w/w; and
  one or more agents acting as a skin-penetration enhancer (preferably acting as both a solubiliser and skin-penetration enhancer and/or preferably hydrophilic such as propylene glycol) present in total at 0.5% to 50% w/w, such as 5% to 50% w/w or 7% to 30% w/w; and
  optionally one or more antioxidants (e.g. butylated hydroxyanisole), e.g. present in total at 0.001 to 2% w/w such as 0.02 to 2% w/w; and
  optionally one or more preservatives, e.g. present in total at 0.01 to 4% w/w such as 0.05 to 1% w/w (e.g. methylparaben present at 0.05 to 2% w/w and/or propylparaben present at 0.01 to 2% w/w).

The above exemplary composition, including the oil "phase" and the penetration enhancer, can optionally be a homogeneous single phase. However, in one embodiment of the above exemplary ointment composition, e.g. when using propylene glycol or another hydrophilic solubiliser and penetration enhancer, the oil phase (oily ointment base) and a hydrophilic phase containing the hydrophilic solubiliser and penetration enhancer (e.g. propylene-glycol-containing phase) have been emulsified to form an ointment emulsion.

Ointment compositions having two phases can optionally be prepared using an emulsification process whereby the hydrophilic phase (e.g. propylene-glycol-containing phase) and oil phase are first prepared in separate vessels. The hydrophilic phase can optionally contain a penetration enhancer such as propylene glycol, and optionally some or all of the compound of formula (I) or salt thereof. The oil phase can optionally contain a surfactant. Temperatures of both phases are maintained at elevated temperatures, such as about 55-90° C. or preferably from above 70 to 90° C., the oil phase temperature being sufficiently high (e.g. from above 70 to 90° C.) to melt the oil phase. While hot, one phase is added to another while mixing, e.g. using a high shear mixer, to effect emulsification, preferably keeping the temperature above 70° C. such as from above 70 to 90° C. The resulting ointment emulsion is allowed to cool, e.g. to about 15-35° C. such as to about 18-30° C., preferably while the agitation continues e.g. at lower speeds. The ointment emulsion can then optionally be dispensed from the manufacturing vessel and filled into primary packaging, for example tubes or sachets.

Optionally, an ointment can comprise a polyethylene glycol base, e.g. present at 25 to 98% w/w such as 50 to 95% w/w, instead of or as well as an oily ointment base.

Creams: An external-topical pharmaceutical composition can be a cream, e.g. a water-in-oil cream or an oil-in-water cream. Creams can sometimes be more fluid than ointments, can sometimes provide more moisture, and hence may in principle in certain cases allow for improved and/or good efficacy in patients with atopic dermatitis.

Water-in-oil creams: These usually have an increased aqueous content compared to ointments. Preferably, the water-in-oil cream is a water-in-oil cream emulsion. That is, preferably, in the water-in-oil cream, an oil phase and an aqueous phase have been emulsified to form a water-in-oil cream emulsion.

An exemplary external-topical pharmaceutical composition is a water-in-oil cream (e.g. cream emulsion) comprising:
- the compound of formula (I) or pharmaceutically acceptable salt thereof present at 0.1% to 5% w/w (e.g. 0.1% to 3% w/w or 0.2% to 1.5% w/w);
- an oil phase (oily ointment base) present at 25% to 85% w/w or 35% to 70% w/w (for example comprising white petrolatum present at 25% to 75% w/w or 30% to 65% w/w, and optionally also comprising mineral oil (e.g. as solubiliser and emollient) present at 2.5% to 15% w/w or 4% to 12% w/w);
- water present in 2% to 30% w/w, e.g. 5% to 25% or 10% to 22% w/w;
- one or more surfactants (e.g. polyoxyl stearyl ether) present in total at 0.5% to 12% w/w, such as 3% to 10% w/w; and
- one or more agents acting as a skin-penetration enhancer (preferably acting as both a solubiliser and skin-penetration enhancer and/or preferably hydrophilic such as propylene glycol) present in total at 0.5% to 50% w/w, such as 5% to 50% w/w or 7% to 30% w/w; and
- optionally one or more antioxidants (e.g. butylated hydroxyanisole), e.g. present in total at 0.001 to 2% w/w such as 0.02 to 2% w/w; and
- optionally one or more preservatives, e.g. present in total at 0.01 to 4% w/w such as 0.05 to 1% w/w (e.g. methylparaben present at 0.05 to 2% w/w and/or propylparaben present at 0.01 to 2% w/w).

Oil-in-water creams: These usually have an increased aqueous content compared to ointments and water-in-oil creams. Preferably, the oil-in-water cream is a oil-in-water cream emulsion. That is, preferably, in the oil-in-water cream, an oil phase and an aqueous phase have been emulsified to form a oil-in-water cream emulsion.

Preferable oil-in-water creams are high-occlusion creams, wherein, after topical administration to the skin, moisture loss from the skin and/or from the cream is reduced or limited by means of sufficiently high coverage of the skin and/or by providing a sufficient barrier at the site of application.

Preferably, the oil-in-water cream contains one or more emollients (hydrating agents), such as silicones (e.g. dimethicone, e.g. dimethicone 360 or dimethicone 20), a high-viscosity wax such as microcrystalline wax, and/or mineral oil. A sufficiently high water content is also preferred, for example wherein the water is present in 15% to 60% w/w, 20% to 50% w/w, or 25% to 40% w/w.

An exemplary external-topical pharmaceutical composition is a oil-in-water cream (e.g. cream emulsion) comprising:
- the compound of formula (I) or pharmaceutically acceptable salt thereof present at 0.1% to 5% w/w (e.g. 0.1% to 3% w/w or 0.2% to 1.5% w/w);
- an oil phase (oily ointment base) containing one or more ingredients capable of acting as emollients, the oil phase being present at 5% to 60% w/w or preferably 20% to 60% w/w or 30% to 60% w/w or more preferably 30% to 55% w/w;
- water present in 12% to 75% w/w or 15% to 75% w/w or 15% to 60% w/w, preferably 15% to 50% w/w or 20% to 40% w/w;
- one or more surfactants present in total at 0.5% to 12% w/w, e.g. 3% to 10% w/w; and
- one or more agents acting as a skin-penetration enhancer (preferably acting as both a solubiliser and skin-penetration enhancer and/or preferably hydrophilic such as propylene glycol) present in total at 0.5% to 50% w/w, preferably 5% to 50% w/w or 7% to 25% w/w; and
- optionally one or more solubilisers (e.g. isopropyl myristate), e.g. present at 0.5% to 20% w/w, e.g. 3 to 12% w/w; and
- optionally one or more buffers (e.g. citric acid and/or dibasic sodium phosphate), e.g. present in total at 0.05 to 5% w/w.

In the above exemplary oil-in-water cream composition, the oil phase preferably comprises mineral oil (e.g. as emollient and solubiliser) present at 15% to 50% w/w or 20% to 45% w/w, and/or comprises a high-viscosity wax such as microcrystalline wax (e.g. as emollient) present at 5% to 25% w/w such as 8% to 15% w/w, and/or comprises a silicone (such as dimethicone e.g. dimethicone 360 or dimethicone 20, e.g. as emollient) present at 0.5% to 20% such as 0.5% to 10% or 1% to 5% w/w.

In the above exemplary oil-in-water cream composition, the one or more surfactants preferably comprise: glycerol monostearate present at 0.5% to 10% w/w, and/or sorbitan monostearate present at 0.05% to 10% w/w, and/or [cetyl alcohol and/or stearyl alcohol] present in total at 0.1% to 15% or 1 to 10% w/w.

Cream emulsions, e.g. water-in-oil or oil-in-water cream emulsions, can be prepared by a process in which an aqueous phase is prepared, e.g. prepared before emulsification. The aqueous phase usually contains water and a solubiliser and/or skin-penetration enhancer such as propylene glycol, and optionally contains some or all of the compound of formula (I) or salt thereof, and/or optionally contains surfactant. The oil phase, e.g. containing white petrolatum and/or mineral oil, and/or optionally containing surfactant, can be prepared in a separate vessel. Temperatures of both phases are maintained at elevated temperatures, such as about 55-90° C. or preferably from above 70 to 90° C., the oil phase temperature being sufficiently high (e.g. from above 70 to 90° C.) to melt the oil phase. While hot, one phase is added to another while mixing, e.g. using a high shear mixer, to effect emulsification, preferably keeping the temperature above 70° C. such as from above 70 to 90° C. The resulting emulsion is allowed to cool, e.g. to about 15-35° C. such as to about 18-30° C., preferably while the agitation continues e.g. at lower speeds. The cream emulsion can then optionally be dispensed from the manufacturing vessel and filled into primary packaging, for example tubes or sachets.

Typically, a pharmaceutical composition of the invention suitable for external topical administration can be administered once daily, twice daily or more than twice daily, to external body part(s), e.g. on the skin such as at a site of diseased skin, e.g. skin suffering from atopic dermatitis.

Inhalable and Intranasal Pharmaceutical Compositions, and Particle Size Reduction Compositions suitable for (e.g. adapted for) nasal or inhaled administration may conveniently be formulated as aerosols, drops, gels or dry powders.

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide, or an organic propellant such as a chlorofluorocarbon (CFC) or more preferably a hydrofluorocarbon (HFC). Suitable CFC propellants include dichlorodifluoromethane, trichlorofluoromethane and dichlorotetrafluoroethane. Suitable HFC propellants include 1,1,1,2,3,3,3-heptafluoropropane and 1,1,1,2-tetrafluoroethane. The aerosol dosage forms can also take the form of a pump-atomiser.

Particle size reduction: For pharmaceutical compositions suitable for (e.g. adapted for) inhaled administration, it is preferred that the compound or salt of formula (I) is in a particle-size-reduced form. The size-reduced form can for example be obtained or obtainable by micronisation. Micronisation usually involves subjecting the compound/salt to collisional and/or abrasional forces in a fast-flowing circular or spiral/vortex-shaped airstream often including a cyclone component. The preferable particle size of the size-reduced (e.g. micronised) compound or salt is defined by a D50 value of about 0.5 to about 10 microns, e.g. about 1 to about 7 microns (e.g. as measured using laser diffraction). For example, it is preferable for the compound or salt of formula (I) to have a particle size defined by: a D10 of about 0.3 to about 3 microns (e.g. about 0.5 to about 2 microns, or about 1 micron), and/or a D50 of about 0.5 to about 10 microns or about 1 to about 7 microns (e.g. about 2 to about 5 microns or about 2 to about 4 microns), and/or a D90 of about 1 to about 30 microns or about 2 to about 20 microns or about 3 to about 15 microns (e.g. about 5 to about 15 microns or about 5 to about 10 microns); for example as measured using laser diffraction.

In particle size measurements, D90, D50 and D10 respectively mean that 90%, 50% and 10% of the material is less than the micron size specified. D50 is the median particle size. DV90, DV50 and DV10 respectively mean that 90%, 50% and 10% by volume of the material is less than the micron size specified. DM90, DM50 and DM10 respectively mean that 90%, 50% and 10% by weight of the material is less than the micron size specified.

Laser diffraction measurement of particle size can use a dry method (wherein a suspension of the compound/salt in an airflow crosses the laser beam) or a wet method [wherein a suspension of the compound/salt in a liquid dispersing medium, such as isooctane or (e.g. if compound is soluble in isooctane) 0.1% Tween 80 in water, crosses the laser beam]. With laser diffraction, particle size is preferably calculated using the Fraunhofer calculation; and/or preferably a Malvern Mastersizer or Sympatec apparatus is used for measurement. For example, particle size measurement and/or analysis by laser diffraction can use any or all of (preferably all of) the following: a Malvern Mastersizer longbed version, a dispersing medium of 0.1% Tween 80 in water, a stir rate of ca. 1500 rpm, ca. 3 mins sonification prior to final dispersion and analysis, a 300 RF (Reverse Fourier) lens, and/or the Fraunhofer calculation with Malvern software.

For a small-scale non-limiting example of micronisation, see the Micronisation Example hereinafter.

Dry powder inhalable compositions: For pharmaceutical compositions suitable (e.g. adapted for) inhaled administration, the pharmaceutical composition may for example be a dry powder inhalable composition. Such a composition can comprise a powder base such as lactose or starch, the compound of formula (I) or salt thereof (preferably in particle-size-reduced form, e.g. in micronised form), and optionally a ternary agent such as L-leucine, mannitol, trehalose, magnesium stearate and/or cellobiose octaacetate (e.g. alpha-D-isomer of cellobiose octaacetate, e.g. available from Aldrich). For cellobiose octaacetate and storage stability, see WO 03/088943.

Preferably, the dry powder inhalable composition comprises a dry powder blend of lactose and the compound of formula (I) or salt thereof. The lactose is preferably lactose hydrate e.g. lactose monohydrate and/or is preferably inhalation-grade and/or fine-grade lactose. Preferably, the particle size of the lactose is defined by 90% or more (by weight or by volume) of the lactose particles being less than 1000 microns (micrometres) (e.g. 10-1000 microns e.g. 30-1000 microns) in diameter, and/or 50% or more of the lactose particles being less than 500 microns (e.g. 10-500 microns) in diameter. More preferably, the particle size of the lactose is defined by 90% or more of the lactose particles being less than 300 microns (e.g. 10-300 microns e.g. 50-300 microns) in diameter, and/or 50% or more of the lactose particles being less than 100 microns in diameter. Optionally, the particle size of the lactose is defined by 90% or more of the lactose particles being less than 100-200 microns in diameter, and/or 50% or more of the lactose particles being less than 40-70 microns in diameter. It is suitable that about 3 to about 30% (e.g. about 10%) (by weight or by volume) of the particles are less than 50 microns or less than 20 microns in diameter. For example, without limitation, a suitable inhalation-grade lactose is E9334 lactose (10% fines) (Borculo Domo Ingredients, Hanzeplein 25, 8017 JD Zwolle, Netherlands).

In the dry powder inhalable composition, the compound of formula (I) or salt thereof can for example be present in about 0.1% to about 70% (e.g. about 1% to about 50%, e.g. about 5% to about 40%, e.g. about 20 to about 30%) by weight of the composition.

An illustrative non-limiting example of a dry powder inhalable composition is given in the Composition Examples below.

Dry powder inhalation devices: Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose, e.g. of the dry powder composition, can be administered by inhalation via a device such as the DISKUS™ device, marketed by GlaxoSmithKline. The DISKUS™ inhalation device is usually substantially as described in GB 2,242,134 A. In such device at least one container for the pharmaceutical composition in powder form (the at least one container preferably being a plurality of sealed dose containers mounted longitudinally in a strip or ribbon) is defined between two members peelably secured to one another; the device comprises: means defining an opening station for the said at least one container; means for peeling the members apart at the opening station to open the container; and an outlet, communicating with the opened container, through which a user can inhale the pharmaceutical composition in powder form from the opened container.

Pharmaceutical Compositions for Oral or Parenteral Administration

A pharmaceutical composition suitable for (e.g. adapted for) parenteral (e.g. intravenous, subcutaneous, or intramuscular) administration can comprise a solution or suspension of the compound or pharmaceutically acceptable salt in a sterile parenterally acceptable aqueous carrier (e.g. sterile water) or parenterally acceptable oil. Alternatively, the solution can be lyophilised. A lyophilised pharmaceutical composition suitable for (e.g. adapted for) parenteral administration may, in use, optionally be reconstituted with a suitable solvent, e.g. sterile water or a sterile parenterally acceptable aqueous solution, just prior to administration.

Oral administration is not preferred, as described above. However, a pharmaceutical composition for oral administration may be liquid or solid; for example it may be a syrup, suspension or emulsion, a tablet, a capsule or a lozenge.

A liquid formulation may optionally consist of a suspension or solution of the compound or pharmaceutically acceptable salt in a pharmaceutically acceptable liquid carrier(s), for example an aqueous solvent such as water, ethanol or glycerine, or a non-aqueous solvent, such as polyethylene glycol or an oil. The formulation may also contain a suspending agent, preservative, flavouring and/or colouring agent.

A pharmaceutical composition for oral administration being a tablet, though not preferred, may comprise one or more pharmaceutically acceptable carriers and/or excipients suitable for preparing tablet formulations. The carrier may for example be or include lactose, cellulose (for example microcrystalline cellulose), or mannitol. The tablet may also or instead contain one or more pharmaceutically acceptable excipients, for example a binding agent such as hydroxypropylmethylcellulose or povidone (polyvinylpyrollidone), a lubricant e.g. an alkaline earth metal stearate such as magnesium stearate, and/or a tablet disintegrant such as sodium starch glycollate, croscarmellose sodium, or crospovidone (cross-linked polyvinylpyrollidone). A pharmaceutical composition being a tablet may be prepared by a method comprising the steps of: (i) mixing the compound of formula (I), as herein defined, or a pharmaceutically acceptable salt thereof, with the one or more pharmaceutically acceptable carriers and/or excipients, (ii) compressing the resulting mixture (which is usually in powder form) into tablets, and (iii) optionally coating the tablet with a tablet film-coating material.

A pharmaceutical composition for oral administration being a capsule, though not preferred, may be prepared using encapsulation procedures. For example, pellets or powder containing the active ingredient may be prepared using a suitable pharmaceutically acceptable carrier and then filled into a hard gelatin capsule. Alternatively, a dispersion or suspension may be prepared using any suitable pharmaceutically acceptable carrier, for example an aqueous gum or an oil and the dispersion or suspension then filled into a soft gelatin capsule.

Dosing Regimens

In a pharmaceutical composition suitable for (e.g. adapted for) external topical administration, e.g. an ointment or an oil-in-water or water-in-oil composition, the compound of formula (I) or the pharmaceutically acceptable salt thereof can be present in 0.05% to 10%, preferably 0.1% to 5%, more preferably 0.1% to 3%, still more preferably 0.2% to 3% (e.g. about 0.5% or about 2.5%), yet more preferably 0.2% to 1.5% (e.g. about 0.5%), by weight of the composition. Typically, an external-topical pharmaceutical composition can be administered once daily, twice daily or more than twice daily, to external body part(s), e.g. to the skin such as at a site of diseased skin. The amount administered is usually such as substantially to cover the site(s) of diseased skin.

In the pharmaceutical composition, a or each dosage unit for oral or parenteral administration can for example contain from 0.01 to 3000 mg, for example 0.5 to 1000 mg, of a compound of the formula (I) or a pharmaceutically acceptable salt thereof, calculated as the free base. A or each dosage unit for nasal or inhaled administration can for example contain from 0.001 to 50 mg, e.g. 0.01 to 5 mg, of a compound of the formula (I) or a pharmaceutically acceptable salt thereof, calculated as the free base.

When a parenteral or oral composition is used, a pharmaceutically acceptable compound or salt of the invention can optionally be administered to a mammal (e.g. human) in a daily oral or parenteral dose of 0.001 mg to 50 mg per kg body weight per day (mg/kg/day), for example 0.01 to 20 mg/kg/day or 0.03 to 10 mg/kg/day or 0.1 to 2 mg/kg/day, of the compound of the formula (I) or a pharmaceutically acceptable salt thereof, calculated as the free base.

When an inhaled or nasal composition is used, a pharmaceutically acceptable compound or salt of the invention can optionally be administered to a mammal (e.g. human) in a daily nasal or inhaled dose of: 0.0001 to 5 mg/kg/day or 0.0001 to 1 mg/kg/day, e.g. 0.001 to 1 mg/kg/day or 0.001 to 0.3 mg/kg/day or 0.001 to 0.1 mg/kg/day or 0.005 to 0.3 mg/kg/day, of the compound of the formula (I) or a pharmaceutically acceptable salt thereof, calculated as the free base.

The pharmaceutically acceptable compounds or salts of the invention can optionally be administered to a human in a daily dose (for an adult patient) of, for example, an oral or parenteral dose of 0.01 mg to 3000 mg per day or 0.5 to 1000 mg per day e.g. 2 to 500 mg per day, or a nasal or inhaled dose of 0.001 to 300 mg per day or 0.001 to 50 mg per day or 0.01 to 30 mg per day or 0.01 to 5 mg per day or 0.02 to 2 mg per day, of the compound of the formula (I) or a pharmaceutically acceptable salt thereof, calculated as the free base.

Combinations

The compounds, salts and/or pharmaceutical compositions according to the invention may also be used in combination with another therapeutically active agent, for example, a $\beta_2$ adrenoreceptor agonist, an anti-histamine, an anti-allergic, an anti-inflammatory agent, an antiinfective agent or an immunosuppressant.

The invention thus provides, in a further aspect, a combination comprising a compound of formula (I) or a pharmaceutically acceptable salt thereof together with another therapeutically active agent, for example, a $\beta_2$-adrenoreceptor agonist, an anti-histamine, an anti-allergic, an anti-inflammatory agent, an antiinfective agent or an immunosuppressant.

Preferably, the $\beta_2$-adrenoreceptor agonist is salmeterol (e.g. as racemate or a single enantiomer such as the R-enantiomer), salbutamol, formoterol, salmefamol, fenoterol or terbutaline, or a salt thereof (e.g. pharmaceutically acceptable salt thereof), for example the xinafoate salt of salmeterol, the sulphate salt or free base of salbutamol or the fumarate salt of formoterol. Long-acting $\beta_2$-adrenoreceptor agonists are preferred, especially those having a therapeutic effect over a 12-24 hour period such as salmeterol or formoterol. Preferably, the $\beta_2$-adrenoreceptor agonist is for inhaled administration, e.g. once per day and/or for simultaneous inhaled administration; and more preferably the $\beta_2$-adrenoreceptor agonist is in particle-size-reduced form e.g. as defined herein. Preferably, the β₂-adrenoreceptor agonist combination is for treatment and/or prophylaxis of COPD or asthma. Salmeterol or a pharmaceutically acceptable salt thereof, e.g. salmeterol xinofoate, is preferably administered to humans at an inhaled dose of 25 to 50 micrograms twice per day (measured as the free base). Preferred long acting β₂-adrenoreceptor agonists include those described in WO 02/066422A, WO 03/024439, WO002/070490 and WO 02/076933.

Preferred long-acting β₂-adrenoreceptor agonists include compounds of formula (XX) (described in WO 02/066422):

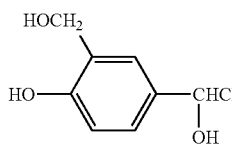

(XX)

or a salt or solvate thereof, wherein in formula (XX):
$m^x$ is an integer of from 2 to 8;
$n^x$ is an integer of from 3 to 11,
with the proviso that $m^x+n^x$ is 5 to 19,
$R^{11X}$ is —XSO₂NR$^{16X}$R$^{17X}$ wherein X is —(CH₂)$_{p^x}$— or C$_{2-6}$ alkenylene;
$R^{16X}$ and $R^{17X}$ are independently selected from hydrogen, C$_{1-6}$alkyl, C$_{3-7}$cycloalkyl, C(O)NR$^{18X}$R$^{19X}$, phenyl, and phenyl (C$_{1-4}$alkyl)-, or R$^{16X}$ and R$^{17X}$, together with the nitrogen to which they are bonded, form a 5-, 6-, or 7-membered nitrogen containing ring, and R$^{16X}$ and R$^{17X}$ are each optionally substituted by one or two groups selected from halo, C$_{1-6}$alkyl, C$_{1-6}$haloalkyl, C$_{1-6}$alkoxy, hydroxy-substituted C$_{1-6}$alkoxy, —CO₂R$^{18X}$, —SO₂NR$^{18X}$R$^{19X}$, —CONR$^{18X}$R$^{19X}$, —NR$^{18X}$C(O)R$^{19X}$, or a 5-, 6- or 7-membered heterocylic ring;
$R^{18X}$ and $R^{19X}$ are independently selected from hydrogen, C$_{1-6}$alkyl,
C$_{3-6}$cycloalkyl, phenyl, and phenyl (C$_{1-4}$alkyl)-; and
$p^x$ is an integer of from 0 to 6, preferably from 0 to 4;
$R^{12X}$ and $R^{13X}$ are independently selected from hydrogen, C$_{1-6}$alkyl, C$_{1-6}$alkoxy, halo, phenyl, and C$_{1-6}$haloalkyl; and
$R^{14X}$ and $R^{15X}$ are independently selected from hydrogen and C$_{1-4}$alkyl with the proviso that the total number of carbon atoms in R$^{14X}$ and R$^{15X}$ is not more than 4.

Preferred β₂-adrenoreceptor agonists disclosed in WO 02/066422 include:
3-(4-{[6-({(2R)-2-hydroxy-2-[4-hydroxy-3-(hydroxymethyl)-phenyl]ethyl}amino)hexyl]oxy}butyl)benzenesulfonamide and
3-(3-{[7-({(2R)-2-hydroxy-2-[4-hydroxy-3-hydroxymethyl)phenyl]ethyl}-amino)heptyl]oxy}propyl)benzenesulfonamide.

A preferred β₂-adrenoreceptor agonist disclosed in WO 03/024439 is:
4-{(1R)-2-[(6-{2-[(2,6-dichlorobenzyl)oxy]ethoxy}hexyl) amino]-1-hydroxyethyl}-2-(hydroxymethyl)phenol.

An anti-histamine, usable in a combination of a compound of formula (I) or salt can for example be for oral administration (e.g. as a combined composition such as a combined tablet), and can be for treatment and/or prophylaxis of allergic rhinitis. Examples of anti-histamines include methapyrilene, or H1 antagonists such as cetirizine, loratadine (e.g. Clarityn™), desloratadine (e.g. Clarinex™) or fexofenadine (e.g. Allegra™).

The invention also provides, in a further aspect, a combination comprising a compound of formula (I) or a pharmaceutically acceptable salt thereof together with an anticholinergic compound, e.g. a muscarinic (M) receptor antagonist in particular an M₁, M₂, M₁/M₂, or M₃ receptor antagonist, more preferably a M₃ receptor antagonist, still more preferably a M₃ receptor antagonist which selectively antagonises (e.g. antagonises 10 times or more strongly) the M₃ receptor over the M₁ and/or M₂ receptor. For combinations of anticholinergic compounds/muscarinic (M) receptor antagonist with PDE4 inhibitors, see for example WO 03/011274 A2 and WO 02/069945 A2/US 2002/0193393 A1 and US 2002/052312 A1, and some or all of these publications give examples of anticholinergic compounds/muscarinic (M) receptor antagonists which may be used with the compounds of formula (I) or salts, and/or suitable pharmaceutical compositions. For example, the muscarinic receptor antagonist can comprise or be an ipratropium salt (e.g. ipratropium bromide), an oxitropium salt (e.g. oxitropium bromide), or more preferably a tiotropium salt (e.g. tiotropium bromide); see e.g. EP 418 716 A1 for tiotropium.

The anticholinergic compound or muscarinic (M) receptor antagonist, e.g. M₃ receptor antagonist, is preferably for inhaled administration, more preferably in particle-size-reduced form e.g. as defined herein. More preferably, both the muscarinic (M) receptor antagonist and the compound of formula (I) or the pharmaceutically acceptable salt thereof are for inhaled administration. Preferably, the anticholinergic compound or muscarinic receptor antagonist and the compound of formula (I) or salt are for simultaneous administration. The muscarinic receptor antagonist combination is preferably for treatment and/or prophylaxis of COPD.

Other possible combinations include, for example, a combination comprising a compound of formula (I) or a pharmaceutically acceptable salt thereof together with another anti-inflammatory agent such as an anti-inflammatory corticosteroid; or a non-steroidal anti-inflammatory drug (NSAID) such as a leukotriene antagonist (e.g. montelukast), an iNOS inhibitor, a tryptase inhibitor, a elastase inhibitor, a beta-2 integrin antagonist, a adenosine 2a agonist, or a 5-lipoxogenase inhibitor; or an antiinfective agent (e.g. an antibiotic or an antiviral). An iNOS inhibitor is preferably for oral administration. Suitable iNOS inhibitors (inducible nitric oxide synthase inhibitors) include those disclosed in WO 93/13055, WO 98/30537, WO 02/50021, WO 95/34534 and WO 99/62875.

Exemplary combinations, in particular for external topical administration (e.g. versus atopic dermatitis), include, for example, a combination comprising a compound of formula (I) or a pharmaceutically acceptable salt thereof together with an immunosuppressant, e.g. a calcineurin inhibitor such as pimecrolimus or tacrolimus. The immunosuppressant can in particular be an externally-topically administrable immunosuppressant such as pimecrolimus (e.g. pimecrolimus at ca. 1% w/w concentration in a topical composition such as a cream, and/or e.g. Elidel™) or tacrolimus (e.g. tacrolimus at from about 0.03% to about 0.1% w/w concentration in a topical composition such as an ointment, and/or e.g. Protopic™). The externally-topically administrable immunosuppressant can be administered or administrable in a external-topical composition separately from the compound or salt of the invention, or it can be contained with the compound of formula (I) or pharmaceutically acceptable salt in a combined externally-topically-administrable composition.

For external topical administration, e.g. versus atopic dermatitis, a combination of the compound or salt of the invention together with an anti-infective agent can include an externally-topically-administrable antibacterial such as mupiricin or a salt (e.g. calcium salt) thereof (e.g. Bactroban™), or an externally-topically-administrable pleuromutilin antibacterial. Alternatively or additionally, for external topical administration an externally-topically-administrable antifungal such as clortrimazole, clotrimazole or ketoconazole can be used. For external topical administration, e.g. versus atopic dermatitis, a combination with an anti-itch compound may optionally be used.

In a combination comprising a compound of formula (I) or a pharmaceutically acceptable salt thereof together with an anti-inflammatory corticosteroid (which can for example be for treatment and/or prophylaxis of asthma, COPD, allergic rhinitis or atopic dermatitis), then the anti-inflammatory corticosteroid can for example be fluticasone propionate (e.g. see U.S. Pat. No. 4,335,121), beclomethasone 17-propionate ester, beclomethasone 17,21-dipropionate ester, dexamethasone or an ester thereof, mometasone or an ester thereof e.g. mometasone furoate), ciclesonide, budesonide, flunisolide, or a compound as described in WO 02/12266 A1 (e.g. as claimed in any of claims 1 to 22 therein), or a pharmaceutically acceptable salt of any of the above. If the anti-inflammatory corticosteroid is a compound as described in WO 02/12266 A1, then preferably it is Example 1 therein {which is 6α,9α-difluoro-17α-[(2-furanylcarbonyl)oxy]-11β-hydroxy-16α-methyl-3-oxo-androsta-1,4-diene-17β-carbothioic acid S-fluoromethyl ester} or Example 41 therein {which is 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester}, or a pharmaceutically acceptable salt thereof. The anti-inflammatory corticosteroid can be for external topical, intranasal or inhaled administration. Fluticasone propionate is preferred and is preferably for inhaled administration to a human either (a) at a dose of 250 micrograms once per day or (b) at a dose of 50 to 250 micrograms twice per day.

Also provided is a combination comprising a compound of formula (I) or a pharmaceutically acceptable salt thereof together with $β_2$-adrenoreceptor agonist and an anti-inflammatory corticosteroid, for example as described in WO 03/030939 A1. Preferably this combination is for treatment and/or prophylaxis of asthma, COPD or allergic rhinitis. The $β_2$-adrenoreceptor agonist and/or the anti-inflammatory corticosteroid can be as described above and/or as described in WO 03/030939 A1. Most preferably, in this "triple" combination, the $β_2$-adrenoreceptor agonist is salmeterol or a pharmaceutically acceptable salt thereof (e.g. salmeterol xinafoate) and the anti-inflammatory corticosteroid is fluticasone propionate.

The combinations referred to above may be presented for use in the form of a pharmaceutical composition and thus a pharmaceutical composition comprising a combination as defined above together with one or more pharmaceutically acceptable carriers and/or excipients represent a further aspect of the invention.

The individual compounds of such combinations may be administered either sequentially or simultaneously in separate or combined pharmaceutical composition.

In one embodiment, the combination as defined herein can be for simultaneous inhaled administration and is disposed in a combination inhalation device. Such a combination inhalation device is another aspect of the invention. Such a combination inhalation device can comprise a combined pharmaceutical composition for simultaneous inhaled administration (e.g. dry powder composition), the composition comprising all the individual compounds of the combination, and the composition being incorporated into a plurality of sealed dose containers mounted longitudinally in a strip or ribbon inside the inhalation device, the containers being rupturable or peel-openable on demand; for example such inhalation device can be substantially as described in GB 2,242,134 A (DISKUS™) and/or as described above. Alternatively, the combination inhalation device can be such that the individual compounds of the combination are administrable simultaneously but are stored separately (or wholly or partly stored separately for triple combinations), e.g. in separate pharmaceutical compositions, for example as described in PCT/EP03/00598 filed on 22 Jan. 2003, published as WO 03/061743 (e.g. as described in the claims thereof e.g. claim 1).

The invention also provides a method of preparing a combination as defined herein, the method comprising either
(a) preparing a separate pharmaceutical composition for administration of the individual compounds of the combination either sequentially or simultaneously, or
(b) preparing a combined pharmaceutical composition for administration of the individual compounds of the combination simultaneously,
wherein the pharmaceutical composition comprises the combination together with one or more pharmaceutically acceptable carriers and/or excipients.

The invention also provides a combination as defined herein, prepared by a method as defined herein.

Biological Test Methods

PDE 3, PDE 4B, PDE 4D, PDE 5, PDE 6 Primary Assay Methods

The activity of the compound or salt of the invention can be measured in the assay methods shown below. The compound of formula (I) appears to be a selective PDE4 inhibitor (compared to PDE3 and PDE5), i.e. it inhibits PDE4B and/or PDE4D more strongly than it inhibits PDE3 and more strongly than it inhibits PDE5.

Possible PDE Enzyme Sources and Literature References

Human recombinant PDE4B, in particular the 2B splice variant thereof (HSPDE4B2B), is disclosed in WO 94/20079 and also M. M. McLaughlin et al., "A low Km, rolipram-sensitive, cAMP-specific phosphodiesterase from human brain: cloning and expression of cDNA, biochemical characterisation of recombinant protein, and tissue distribution of mRNA", *J. Biol. Chem.*, 1993, 268, 6470-6476. For example, in Example 1 of WO 94/20079, human recombinant PDE4B is described as being expressed in the PDE-deficient yeast *Saccharomyces cerevisiae* strain GL62, e.g. after induction by addition of 150 uM $CuSO_4$, and 100,000×g supernatant fractions of yeast cell lysates are described for use in the harvesting of PDE4B enzyme.

Human recombinant PDE4D (HSPDE4D3A) is disclosed in P. A. Baecker et al., "Isolation of a cDNA encoding a human rolipram-sensitive cyclic AMP phoshodiesterase (PDE $IV_D$)", *Gene*, 1994, 138, 253-256.

Human recombinant PDE5 is disclosed in K. Loughney et al., "Isolation and characterisation of cDNAs encoding PDE5A, a human cGMP-binding, cGMP-specific 3',5'-cyclic nucleotide phosphodiesterase", *Gene,* 1998, 216, 139-147.

PDE3 can be purified from bovine aorta, e.g. as described by H. Coste and P. Grondin, "Characterisation of a novel potent and specific inhibitor of type V phosphodiesterase", *Biochem. Pharmacol.,* 1995, 50, 1577-1585.

PDE6 can be purified from bovine retina, e.g. as described by: P. Catty and P. Deterre, "Activation and solubilization of the retinal cGMP-specific phosphodiesterase by limited proteolysis", *Eur. J. Biochem.,* 1991, 199, 263-269; A. Tar et al. "Purification of bovine retinal cGMP phosphodiesterase", *Methods in Enzymology,* 1994, 238, 3-12; and/or D. Srivastava et al. "Effects of magnesium on cyclic GMP hydrolysis by the bovine retinal rod cyclic GMP phosphodiesterase", *Biochem. J.,* 1995, 308, 653-658.

Inhibition of PDE 3, PDE 4B, PDE 4D, PDE 5 or PDE 6 Activity: Radioactive Scintillation Proximity Assay (SPA)

The ability of compounds to inhibit catalytic activity at PDE4B or 4D (human recombinant), PDE3 (from bovine aorta), PDE5 (human recombinant) or PDE6 (from bovine retina) can optionally be determined by Scintillation Proximity Assay (SPA) in a 96-well format.

Test compounds (as a solution in DMSO, preferably about 2 microliters (ul) volume of DMSO solution) are preincubated at ambient temperature (room temperature, e.g. 19-23° C.) in Wallac Isoplates (code 1450-514) with PDE enzyme in 50 mM Tris-HCl buffer pH 7.5, 8.3 mM $MgCl_2$, 1.7 mM EGTA, 0.05% (w/v) bovine serum albumin for 10-30 minutes (usually 30 minutes). The enzyme concentration is adjusted so that no more than 20% hydrolysis of the substrate defined below occurs in control wells without compound, during the incubation. For the PDE3, PDE4B and PDE4D assays, [5',8-3H]Adenosine 3',5'-cyclic phosphate (Amersham Pharmacia Biotech, code TRK.559; or Amersham Biosciences UK Ltd, Pollards Wood, Chalfont St Giles, Buckinghamshire HP8 4SP, UK) is added to give 0.05uCi per well and about 10 nM final concentration. For the PDE5 and PDE6 assays, [8-$^3$H] Guanosine 3',5'-cyclic phosphate (Amersham Pharmacia Biotech, code TRK.392) is added to give 0.05uCi per well and about 36 nM final concentration. Plates containing assay mixture, preferably approx. 100 ul volume of assay mixture, are mixed on an orbital shaker for 5 minutes and incubated at ambient temperature for 1 hour. Phosphodiesterase SPA beads (Amersham Pharmacia Biotech, code RPNQ 0150) are added (about 1 mg per well) to terminate the assay. Plates are sealed and shaken and allowed to stand at ambient temperature for 35 minutes to 1 hour (preferably 35 minutes) to allow the beads to settle. Bound radioactive product is measured using a WALLAC TRILUX 1450 Microbeta scintillation counter. For inhibition curves, 10 concentrations (e.g. 1.5 nM-30 uM) of each compound are assayed. Curves are analysed using ActivityBase and XLfit (ID Business Solutions Limited, 2 Ocean Court, Surrey Research Park, Guildford, Surrey GU2 7QB, United Kingdom) Results are expressed as $pIC_{50}$ values.

In an alternative to the above radioactive SPA assay, PDE4B or PDE4D inhibition can be measured in the following Fluorescence Polarisation (FP) assay:

Inhibition of PDE4B or PDE4D Activity: Fluorescence Polarisation (FP) Assay

The ability of compounds to inhibit catalytic activity at PDE4B (human recombinant) or PDE4D (human recombinant) can optionally be determined by IMAP Fluorescence Polarisation (FP) assay (IMAP Explorer kit, available from Molecular Devices Corporation, Sunnydale, Calif., USA; Molecular Devices code: R8062) in a 384-well format.

The IMAP FP assay is able to measure PDE activity in an homogenous, non-radioactive assay format. The FP assay uses the ability of immobilised trivalent metal cations, coated onto nanoparticles (tiny beads), to bind the phosphate group of Fl-AMP that is produced on the hydrolysis of fluorescein-labelled (Fl) cyclic adenosine mono-phosphate (Fl-cAMP) to the non-cyclic Fl-AMP form. Fl-cAMP substantially does not bind. Binding of Fl-AMP product to the beads (coated with the immobilised trivalent cations) slows the rotation of the bound Fl-AMP and leads to an increase in the fluorescence polarisation ratio of parallel to perpendicular light. Inhibition of the PDE reduces/inhibits this signal increase.

Test compounds (small volume, e.g. ca. 0.5 to 1 microliters (ul), preferably ca. 0.5 ul, of solution in DMSO) are preincubated at ambient temperature (room temperature, e.g. 19-23° C.) in black 384-well microtitre plates (supplier: NUNC, code 262260) with PDE enzyme in 10 mM Tris-HCl buffer pH 7.2, 10 mM $MgCl_2$, 0.1% (w/v) bovine serum albumin, and 0.05% $NaN_3$ for 10-30 minutes. The enzyme level is set by experimentation so that reaction is linear throughout the incubation. Fluorescein adenosine 3',5'-cyclic phosphate (from Molecular Devices Corporation, Molecular Devices code: R7091) is added to give about 40 nM final concentration (final assay volume usually ca. 20-40 ul, preferably ca. 20 ul). Plates are mixed on an orbital shaker for 10 seconds and incubated at ambient temperature for 40 minutes. IMAP binding reagent (as described above, from Molecular Devices Corporation, Molecular Devices code: R7207) is added (60 ul of a 1 in 400 dilution in binding buffer of the kit stock solution) to terminate the assay. Plates are allowed to stand at ambient temperature for 1 hour. The Fluorescence Polarisation (FP) ratio of parallel to perpendicular light is measured using an Analyst™ plate reader (from Molecular Devices Corporation). For inhibition curves, 10 concentrations (e.g. 1.5 nM-30 uM) of each compound are assayed. Curves are analysed using ActivityBase and XLfit (ID Business Solutions Limited, 2 Ocean Court, Surrey Research Park, Guildford, Surrey GU2 7QB, United Kingdom). Results are expressed as $pIC_{50}$ values.

In the FP assay, reagents are generally dispensed using Multidrop™ (available from Thermo Labsystems Oy, Ratastie 2, PO Box 100, Vantaa 01620, Finland).

For a given PDE4 inhibitor, the PDE4B (or PDE4D) inhibition values measured using the SPA and FP assays can differ slightly. However, in a regression analysis of 100 test compounds (not necessarily the compound of the invention), the $pIC_{50}$ inhibition values measured using SPA and FP assays have been found generally to agree within about 0.5 log units, for each of PDE4B and PDE4D (linear regression coefficient 0.966 for PDE4B and 0.971 for PDE4D; David R. Mobbs et al., "Comparison of the IMAP Fluorescence Polarisation Assay with the Scintillation Proximity Assay for Phosphodiesterase Activity", poster presented at 2003 Molecular Devices UK & Europe User Meeting, 2nd Oct. 2003, Down Hall, Harlow, Essex, United Kingdom).

Biological Data obtained for Example 1 and/or Example 1A (i.e. the compound of formula (I)) (PDE4B and PDE4D inhibitory activities, usually as an average of more than one reading) are as follows, based on current measurements only, and using the above or similar or analogous assay methods. PDE3 and PDE5 inhibitory activities obtained are as follows, and (independently for each) are using either an SPA assay or similar or analogous assay(s), or an appropriately modified Fluorescence Polarisation (FP) assay(s) or similar or analogous assay not specifically described above. In each of the SPA and FP assays, absolute accuracy of measurement is not possible, and the readings given are generally accurate only up to about ±0.5 of a log unit, depending on the number of readings made and averaged:

| Assay done on Example = compound of formula (I) | PDE pIC$_{50}$ data (±about 0.5) (n = no. of tests) |
|---|---|
| PDE4B pIC$_{50}$ (FP assay, mean value) | 9.17 (±about 0.5) (n = 2) |
| PDE4D pIC$_{50}$ (FP assay, mean value) | 9.26 (±about 0.5) (n = 2) |
| PDE3 pIC$_{50}$ | 5.04 (±about 0.5) (n = 1) |
| PDE5 pIC$_{50}$ | 6.31 (±about 0.5) (n = 1) |

Emesis: Some known PDE4 inhibitors can cause emesis and/or nausea to greater or lesser extents, e.g. after systemic exposure (e.g. see Z. Huang et al., *Current Opinion in Chemical Biology*, 2001, 5: 432-438, see especially pages 433-434 and refs cited therein). Therefore, it would be preferable, but not essential, if the compound or salt of the invention were to cause only limited or manageable emetic side-effects, e.g. after external topical, oral or parenteral (e.g. external topical) administration. Emetic side-effects can for example be measured by the emetogenic potential of the compound or salt when administered to ferrets; for example one can measure the time to onset, extent, frequency and/or duration of vomiting, retching and/or writhing in ferrets after oral or parenteral administration of the compound or salt. See for example In vivo Assay 4 hereinafter for one optional measurement method for anti-inflammatory effect, emetic side-effects and therapeutic index (TI) in the ferret. See also for example A. Robichaud et al., "Emesis induced by inhibitors of [PDE IV] in the ferret", *Neuropharmacology*, 1999, 38, 289-297, erratum *Neuropharmacology*, 2001, 40, 465-465. However, optionally, emetic side-effects and therapeutic index (TI) after oral administration in rats can be conveniently measured by monitoring the pica feeding behaviour of rats after administration of the compound or salt of the invention (see In Vivo Assay 2 below).

Other side effects: Some known PDE4 inhibitors can cause other side effects such as headache and other central nervous system (CNS-) mediated side effects; and/or gastrointestinal (GI) tract disturbances. Therefore, it would be preferable, but not essential, if the compound or salt of the invention were to cause only limited or manageable side-effects in one or more of these side-effect categories.

Other Optional In Vitro Assays:

Inhibition of TNF-α (TNF-alpha) Production in Human Whole Blood

This is an optional supplementary test, e.g. for potentially orally-administrable PDE4 inhibitors. Also, as the assay measures the effect of PDE4 inhibitors after loss by protein binding, it might also be relevant to externally-topically-administrable PDE4 inhibitors as protein-binding-loss of compound is possible during transport through the skin.

Test compounds are prepared as a ca. 10 mM stock solution in DMSO and a dilution series prepared in DMSO with 8 successive 3-fold dilutions, either directly from the 10 mM stock solution or from a more dilute solution in DMSO. The compound is added to assay plates using a Biomek Fx liquid handling robot.

Heparinised blood drawn from normal volunteers is dispensed (ca. 100 μl=ca. 100 ul) into microtitre plate wells containing ca. 0.5 or ca. 1.0 μl (ul, microliters) of an appropriately diluted test compound solution. After ca. 1 hr incubation at ca. 37° C., 5% $CO_2$, ca. 25 μl (ca. 25 ul) of LPS (lipopolysaccharide) solution (S. typhosa) in RPMI 1640 (containing 1% L-glutamine and 1% Penicillin/streptomycin) is added (ca. 50 ng/ml final). The samples are incubated at ca. 37° C., 5% $CO_2$, for ca. 20 hours, and ca. 100 μl (ca. 100 ul) physiological saline (0.138% NaCl) is added, and diluted plasma is collected using a Platemate or Biomek FX liquid handling robot after centrifugation at ca. 1300 g for ca. 10 min. Plasma TNFα content is determined by electrochemiluminescence assay using the IGEN technology (see below) or by enzyme linked immunosorbant assay (ELISA) (see below).

Results: For the compound of formula (I) using the above or a similar assay: Inhibition of TNF-α (TNF-alpha) production in Human Whole Blood: pIC50=8.13 (n=6).

Inhibition of TNF-α (TNF-alpha) Production in Human PBMC (Peripheral Blood Mononuclear Cell) Assay This is an optional supplementary test, e.g. for potentially inhalably-administrable PDE4 inhibitors.

Test compounds are prepared as a ca. 10 mM stock solution in DMSO and a dilution series prepared in DMSO with 8 successive 3-fold dilutions, either directly from the 10 mM stock solution or from a more dilute solution in DMSO. The compound is added to assay plates using a Biomek Fx liquid handling robot.

PBMC cells (peripheral blood mononuclear cells) are prepared from heparinised human blood from normal volunteers by centrifugation on histopaque at ca. 1000 g for ca. 30 minutes. The cells are collected from the interface, washed by centrifugation (ca. 1300 g, ca. 10 minutes) and resuspended in assay buffer (RPMI 1640 containing 10% foetal calf serum, 1% L-glutamine and 1% penicillin/streptomycin) at $1 \times 10^6$ cells/ml. Ca. 50 μl (ca. 50 ul) cells are added to microtitre wells containing ca. 0.5 or ca/1.0 μl (ul) of an appropriately diluted compound solution. Ca. 75 μl (ul) LPS (ca. 1 ng/ml final) is added and the samples are incubated at 37° C., 5% $CO_2$, for 20 hours. The supernatant is removed and the concentrations of TNF are determined by electrochemiluminescence assay using the IGEN technology or by ELISA (see below).

Results: For the compound of formula (I) using the above or a similar assay: Inhibition of TNF-α (TNF-alpha) production in PBMCs: pIC50=8.74 (n=9).

TNF-α IGEN Assay

Ca. 50 μl supernatant from either whole blood or PBMC assay plates is transferred to a 96 well polypropylene plate. Each plate also contains a TNF-α standard curve (ca. 0 to 30000 pg/ml: R+D Systems, 210-TA). Ca. 50 μl (ul) of streptavidin/biotinylated anti-TNF-α antibody mix, ca. 25 μl ruthenium tagged anti-TNF-α monoclonal and ca. 100 μl PBS containing 0.1% bovine serum albumin are added to each well and the plates are sealed and shaken for ca. 2 hours before being read on an IGEN instrument.

TNF-α ELISA Assay

Human TNF-α can be assayed using a commercial assay kit (AMS Biotechnology, 211-90-164-40) according to the manufacturers' instructions but with TNF-α calibration curves prepared using Pharmingen TNF-α (cat. No. 555212).

In Vivo Biological Assays

The in vitro enzymatic PDE4B inhibition assay(s) described above or generally similar assays should be regarded as being the primary test(s) of biological activity. However, some additional in vivo biological tests, which are optional and which are not an essential measure of any of activity, efficacy or side-effects, and which have not necessarily been carried out, are described below.

In Vivo Assay A:

Activity of Topically-Applied Compounds in a Pig Model of Atopic Dermatitis: Effect of Compounds, Applied by Skin Topical Administration, on the Dinitrofluorobenzene (DNFB)-Induced Delayed Type Hypersensitivity (DTH) Response in Pigs General Study Design:

The pig DTH (delayed type hypersensitivity) model of contact hypersensitivity utilizes the Th2-mediated inflammatory response in pig skin to mimic the pathology of atopic dermatitis in humans. The model measures the potential anti-inflammatory effect of compounds, topically-applied to the skin, on the acute DTH (delayed type hypersensitivity) response in castrated male Yorkshire pigs.

In general in the assay, pigs (domestic Yorkshire pigs, 15-18 kg at time of sensitization, castrated males) are first sensitized by topical application of ca. 10% (w/v) dinitrofluorobenzene (DNFB) dissolved in DMSO:acetone:olive oil (ca. 1:5:3) (ca. 40 mg DNFB, 400 microlitre solution total) to the ears (outer) and groin (inner). The pigs are then challenged 12 days later with ca. 0.6% (w/v) DNFB applied to randomized sites on the shaved back of the pigs (ca. 90 micrograms/site; sites are identified and numbered by grid made with marking pen).

On the day of challenge, the treatments are performed at about 2 hours prior to and about 6 hours after challenge (for DMSO/acetone solutions/suspensions, to maximize exposure to drug), or at about 30 minutes after and about 6 hours after challenge (for topical ointments or creams, representing a more clinically relevant treatment protocol).

One day (about 24 hrs) after challenge, and optionally again at ca. 48 hrs post challenge, test sites are visually evaluated for intensity and extent of erythema by measuring the diameter of the reaction at its widest point and assigning scores of 0 to 4 for each of erythema intensity and erythema extent. Induration (a measure of swelling) is also scored 0 to 4. Scores for erythema intensity, erythema extent and induration are assigned according to the following criteria: Intensity of Erythema: 0=normal, 1=minimal, barely visible, 2=mild, 3=moderate, 4=severe. Extent of Erythema (not raised): 0=no edema, 1=macules of pin head size, 2=lentil sized macules, 3=confluent macules, 4=diffuse over entire site. Induration (palpable): 0=normal, 1=nodules of pin head size, 2=doughy lentil sized nodules, 3=confluent firm nodules, 4=diffuse hard lesion. The summed visual score at ca. 24 hours includes the individual scores for erythema intensity, erythema extent, and induration; so the maximal summed score for each site would be 12. High summed scores can generally indicate a high inflammatory response. Visual scores are subject to some inaccuracy/error.

Differences in the summed score between adjacent control (placebo) and treatment sites on the grids are calculated. This difference value is then used to determine the percent inhibition compared to the summed score for the control (placebo) sites. The more negative the difference value, the greater the calculated inhibition. Percent inhibition of (percent inhibition compared to) the mean summed score can be calculated.

About 24 hours after challenge, treatment sites can optionally also be visually evaluated for lesion area.

Specific Study Design and Results:

The anti-inflammatory effect of the compound of formula (I) ("free base" form), applied topically to the skin, on the acute DTH response in castrated male Yorkshire pigs is compared to that of another PDE4 inhibitor cipamfylline (BRL-61063) and the topical immunomodulator pimecrolimus.

In the above assay, the compound of formula (I) is topically administered: either (A) at ca. 2.5% (w/v) concentration in a solution of ca. 10% DMSO/90% acetone (ca. 50 microliters or ca. 1.5 mg/site) at about 2 hours prior to and about 6 hours after the DNFB challenge; or (B) at ca. 0.5% (w/w) concentration in an ointment containing propylene glycol (PG)*(ca. 25 mg of formulation/site) at about 30 minutes after and about 6 hours after the DNFB challenge. (*The PG ointment used or usable with the compound of formula (I) generally contains inter alia approximately the following constituents [in % (w/w)]: ca. 69-70% white petrolatum, ca. 5% mineral oil, ca. 5% polyoxyl stearyl ether (e.g. Volpo S2) and ca. 20% propylene glycol. See for example Composition Example C1 hereinafter for a suitable ointment formulation.)

The compound of formula (I) at ca. 0.5% (w/w) in PG ointment inhibits the mean summed score by about 13-14% compared to the placebo PG ointment ($p<0.05$ by ANOVA). The compound of formula (I) administered at ca. 2.5% (w/v) in DMSO/acetone solution gives a reduction of about 21% in the mean summed score compared to vehicle alone ($p<0.05$ by ANOVA). In comparison, cipamfylline at ca. 2.5% (w/v) in DMSO/acetone and cipamfylline at ca. 0.25% (w/w) in ointment reduces the summed scores by about 8% and about 6-7%, respectively (effects that are not statistically significant), whereas pimecrolimus applied in a 1% (w/w) cream formulation inhibits the summed scores by about 29% ($p<0.05$ by ANOVA).

Further, the skin administration of compound of formula (I) appears to decrease the lesion area when added in DMSO/acetone or PG ointment (results subject to some inaccuracy/error).

These results appear to demonstrate the potential anti-inflammatory activity of the compound of formula (I) ("free base" form) in an acute pig DTH (delayed type hypersensitivity) model when the compound is topically administered to the skin in a suitable formulation.

In Vivo Assay 1. LPS-Induced Pulmonary Neutrophilia in Rats: Effect of Orally Administered PDE4 Inhibitors Pulmonary neutrophil influx is thought to be a significant component to the family of pulmonary diseases like chronic obstructive pulmonary disease (COPD) which can involve chronic bronchitis and/or emphysema (G. F. Filley, *Chest*. 2000; 117(5); 251s-260s). The purpose of this neutrophilia model is to study the potentially anti-inflammatory effects in vivo of orally administered PDE4 inhibitors on neutrophilia induced by inhalation of aerosolized lipopolysaccharide (LPS), modelling the neutrophil inflammatory component(s) of COPD. See the literature section below for scientific background.

Male Lewis rats (Charles River, Raleigh, N.C., USA) weighing approximately 300-400 grams are pretreated with either (a) test compound, for example suspended in about 0.5% methylcellulose (obtainable from Sigma-Aldrich, St Louis, Mo., USA) in water or (b) vehicle only, delivered orally in a dose volume of ca. 10 ml/kg. Generally, dose response curves can for example be generated using the following approx. doses of PDE4 inhibitors: 2.0, 0.4, 0.08, 0.016 and 0.0032 mg/kg. About thirty minutes following pretreatment, the rats are exposed to aerosolized LPS (Serotype *E. Coli* 026:B6 prepared by trichloroacetic acid extraction, obtainable from Sigma-Aldrich, St Louis, Mo., USA), generated from a nebulizer containing a ca. 100 μg/ml LPS solution (ca. 100 ug/ml). Rats are exposed to the LPS aerosol at a rate of ca. 4 L/min for ca. 20 minutes. LPS exposure is carried out in a closed chamber with internal dimensions of roughly 45 cm length×24 cm width×20 cm height. The nebulizer and exposure chamber are contained in a certified fume hood. At about 4 hours-post LPS exposure the rats are euthanized by overdose with pentobarbital at ca. 90 mg/kg, administered intraperitoneally. Bronchoalveolar lavage (BAL) is performed through a 14 gauge blunt needle into the exposed trachea. Five, 5 ml washes are performed to collect a total of 25 ml of BAL fluid. Total cell counts and leukocyte differentials are performed on BAL fluid in order to calculate neutrophil influx into the lung. Percent neutrophil inhibition at each dose (cf. vehicle) is calculated and a variable slope, sigmoidal dose-response curve is generated, usually using Prism Graph-Pad. The dose-response curve is used to calculate an ED50 value (in mg per kg of body weight) for inhibition by the PDE4 inhibitor of the LPS-induced neutrophilia.

Alternative method: In an alternative simpler embodiment of the procedure, a single oral dose of 10 mg/kg, or more usually 1.0 mg/kg or 0.3 mg/kg of the PDE4 inhibitor (or vehicle) is administered to the rats, and percent neutrophil inhibition is calculated and reported for that specific dose.

Literature:

Filley G. F. Comparison of the structural and inflammatory features of COPD and asthma. *Chest.* 2000; 117(5) 251s-260s.

Howell R E, Jenkins L P, Fielding L E, and Grimes D. Inhibition of antigen-induced pulmonary eosinophilia and neutrophilia by selective inhibitors of phosphodiesterase types 3 and 4 in brown Norway rats. *Pulmonary Pharmacology.* 1995; 8: 83-89.

Spond J, Chapman R, Fine J, Jones H, Kreutner W, Kung T T, Minnicozzi M. Comparison of PDE 4 inhibitors, Rolipram and SB 207499 (Ariflo™), in a rat model of pulmonary neutrophilia. *Pulmonary Pharmacology and Therapeutics.* 2001; 14:157-164.

Underwood D C, Osborn R R, Bochnowicz S, Webb E F, Riemarm D J, Lee J C, Romanic A M, Adams J L, Hay D W P, and Griswold D E. SB 239063, a p38 MAPK inhibitor, reduces neutrophilia, inflammatory cytokines, MMP-9, and fibrosis in lung. *Am J Physiol Lung Cell Mol Physiol.* 2000; 279: L895-L902.

In Vivo Assay 2. Rat Pica Model of Emesis

Background: Selective PDE4 inhibitors are thought to inhibit inflammation in various in vitro and in vivo models by increasing intracellular levels of cAMP of many immune cells (e.g. lymphocytes, monocytes). However, a side effect of some PDE4 inhibitors in some species is emesis. Because many rat models of inflammation are well characterized, they can be used in procedures (see e.g. In Vivo Assay 1 above) to show beneficial anti-inflammatory effects of PDE 4 inhibitors. However rats have no emetic response (they have no vomit reflex), so that the relationship between beneficial anti-inflammatory effects of PDE 4 inhibitors and emesis is difficult to study directly in rats.

However, in 1991, Takeda et al. (see Literature section below) demonstrated that the pica feeding response is analogous to emesis in rats. Pica feeding is a behavioural response to illness in rats wherein rats eat non-nutritive substances such as earth or in particular clay (e.g. kaolin) which may help to absorb toxins. Pica feeding can be induced by motion and chemicals (especially chemicals which are emetic in humans), and can be inhibited pharmacologically with drugs that inhibit emesis in humans. The Rat Pica Model, In Vivo Assay 2, can determine the level of pica response of rats to PDE 4 inhibition at pharmacologically relevant doses in parallel to in vivo anti-inflammatory Assays in (a separate set of) rats (e.g. In Vivo Assay 1 above).

Anti-inflammatory and pica assays in the same species together can provide data on the "therapeutic index" (TI) in the rat of the compounds/salts of the invention. The Rat TI can for example be calculated as the ratio of a) the potentially-emetic Pica Response ED50 dose from Assay 2 to b) the rat anti-inflammatory ED50 dose (e.g. measured by rat neutrophilia-inhibition in eg In Vivo Assay 1), with larger TI ratios possibly indicating lower emesis at many anti-inflammatory doses. This might allow a choice of a non-emetic or low-emetic pharmaceutical dose of the compounds or salts of the invention which has an anti-inflammatory effect. It is recognised however that achieving a low-emetic PDE4 inhibitory compound is not essential to the invention.

Procedure: On the first day of the experiment, the rats are housed individually in cages without bedding or "enrichment". The rats are kept off of the cage floor by a wire screen. Pre-weighed food cups containing standard rat chow and clay pellets are placed in the cage. The clay pellets, obtainable from Languna Clay Co, City of Industry, Calif., USA, are the same size and shape as the food pellets. The rats are acclimated to the clay for 72 hours, during which time the cups and food and clay debris from the cage are weighed daily on an electronic balance capable of measuring to the nearest 0.1 grams. By the end of the 72 hour acclimation period the rats generally show no interest in the clay pellets.

At the end of 72 hours the rats are placed in clean cages and the food cups weighed. Rats that are still consuming clay regularly are removed from the study. Immediately prior to the dark cycle (the time when the animals are active and should be eating) the animals are split into treatment groups and dosed orally with a dose of a compound/salt of the invention (different doses for different treatment groups) or with vehicle alone, at a dose volume of ca. 2 ml/kg. In this oral dosing, the compound/salt can for example be in the form of a suspension in about 0.5% methylcellulose (obtainable Sigma-Aldrich, St. Louis, Mo., USA) in water. The food and clay cups and cage debris are weighed the following day and the total clay and food consumed that night by each individual animal is calculated.

A dose response is calculated by first converting the data into quantal response, where animals are either positive or negative for the pica response. A rat is "pica positive" if it consumes greater than or equal to 0.3 grams of clay over the mean of its control group. The D50 value is usually calculated using logistic regression performed by the Statistica software statistical package. A Pica Response ED50 value in mg per kg of body weight can then be calculated.

The Pica Response ED50 value can be compared to the neutrophilia-inhibition ED50 values for the same compound administered orally to the rat (measurable by In Vivo Assay 1 above), so that a Therapeutic Index (TI) in rats can be calculated thus:

$$\text{Rat Therapeutic index}(TI)(50/50) = \frac{\text{Pica Response } ED50 \text{ value}}{\text{rat neutrophilia-inhibition } ED50 \text{ value}}$$

In general, the Therapeutic Index (TI) calculated this way is often substantially different to, and for example can often be substantially higher than, the TI (D20/D50) calculated in the ferret (see In vivo Assay 4 below).

Alternatively, e.g. for a simpler test, the In Vivo Assay 2 (pica) can use only a single oral dose of the test compound (e.g. 10 mg/kg orally).

Literature:

Beavo J A, Contini, M., Heaslip, R. J. Multiple cyclic nucleotide phosphodiesterases. *Mol Pharmacol.* 1994; 46:399-405.

Spond J, Chapman R, Fine J, Jones H, Kreutner W, Kung T T, Minnicozzi M. Comparison of PDE 4 inhibitors, Rolipram and SB 207499 (Ariflo™), in a rat model of pulmonary neutrophilia. *Pulmonary Pharmacology and Therapeudtics.* 2001; 14:157-164.

Takeda N, Hasegawa S, Morita M, and Matsunaga T. Pica in rats is analogous to emesis: an animal model in emesis research. *Pharmacology, Biochemistry and Behavior.* 1991; 45:817-821.

Takeda N, Hasegawa S, Morita M, Horii A, Uno A, Yamatodani A and Matsunaga T. Neuropharmacological mechanisms of emesis. I. Effects of antiemetic drugs on motion- and apomorphine-induced pica in rats. *Meth Find Exp Clin Pharmacol.* 1995; 17(9) 589-596.

Takeda N, Hasegawa S, Morita M, Horii A, Uno A, Yamatodani A and Matsunaga T. Neuropharmacological mechanisms of emesis. II. Effects of antiemetic drugs on cisplatin-induced pica in rats. *Meth Find Exp Clin Pharmacol.* 1995; 17(9) 647-652.

In Vivo Assay 3. LPS Induced Pulmonary Neutrophilia in Rats: Effect of Intratracheally Administered PDE4 Inhibitors This assay is an animal model of inflammation in the lung—specifically neutrophilia induced by lipopolysaccharide (LPS)— and allows the study of putative inhibition of such neutrophilia (anti-inflammatory effect) by intratracheally (i.t.) administered PDE4 inhibitors. The PDE4 inhibitors are preferably in dry powder or wet suspension form. I.t. administration is one model of inhaled administration, allowing topical delivery to the lung.

Animals: Male CD (Sprague Dawley Derived) rats supplied by Charles River, Raleigh, N.C., USA or Charles River, United Kingdom are housed in groups of 5 rats per cage, acclimatised after delivery for at least 5 days with bedding/nesting material regularly changed, fed on SDS diet R1 pelleted food given ad lib, and supplied with daily-changed pasteurised animal grade drinking water.

Device for dry powder administration: Disposable 3-way tap between dosing needle and syringe. The intratracheal dosing device (a 3-way sterile tap, Vycon 876.00; or Penn Century dry powder insufflator, DP-4) is weighed, the drug blend or inhalation grade lactose (vehicle control) is then added to the tap, the tap is closed to prevent loss of drug, and the tap is re-weighed to determine the weight of drug in the tap. After dosing, the tap is weighed again to determine the weight of drug that had left the tap. The needle, a Sigma Z21934-7 syringe needle 19-gauge 152 mm (6 inches) long with luer hub, is cut by engineering to approximately 132 mm (5.2 inches), a blunt end is made to prevent them damaging the rat's trachea, and the needle is weighed prior to and after drug delivery to confirm that no drug is retained in the needles after dosing.

Device for wet suspension administration: This is similar to the above but a blunt dosing needle, whose forward end is slightly angled to the needle axis, is used, with a flexible plastic portex canula inserted into the needle.

Drugs and Materials: Lipopolysaccharide (LPS) (Serotype:0127:B8) is dissolved in phosphate-buffered saline (PBS). PDE4 inhibitors are preferably used in size-reduced (e.g. micronised) form, for example according to the Micronisation Example given herein.

For dry powder administration of the drug, the Dry Powder Formulation Example given herein, comprising drug and inhalation-grade lactose, can optionally be used. one suitable inhalation-grade lactose that can be used has 10% fines (10% of material under 15 um (15 micron) particle size measured by Malvern particle size).

Wet suspensions of the drug (aqueous) can be prepared by adding the required volume of vehicle to the drug; the vehicle used can for example be saline alone or a mixture of saline/tween (e.g. 0.2% tween 80). The wet suspension is usually sonicated for ca. 10 minutes prior to use.

Preparation, and dosing with PDE 4 inhibitor: Rats are anaesthetised by placing the animals in a sealed Perspex chamber and exposing them to a gaseous mixture of isoflourane (4.5%), nitrous oxide (3 liters.minute$^{-1}$) and oxygen (1 litre.minute$^{-1}$). Once anaesthetised, the animals are placed onto a stainless steel i.t. dosing support table. They are positioned on their back at approximately a 35° angle. A light is angled against the outside of the throat to highlight the trachea. The mouth is opened and the opening of the upper airway visualised. The procedure varies for wet suspension and dry powder administration of PDE4 inhibitors as follows:

Dosing with a Wet suspension: A portex cannula is introduced via a blunt metal dosing needle that has been carefully inserted into the rat trachea. The animals are intratracheally dosed with vehicle or PDE4 inhibitor via the dosing needle with a new internal canula used for each different drug group. The formulation is slowly (ca. 10 seconds) dosed into the trachea using a syringe attached to the dosing needle.

Dosing with a Dry Powder: The intratracheal dosing device (a three-way sterile tap device, Vycon 876.00; or Penn Century dry powder insufflator, DP-4) and needle are inserted into the rat trachea up to a pre-determined point established to be located approximately 1 cm above the primary bifurcation. Another operator holds the needle at the specified position whilst 2×4 ml of air (using 3-way tap device) is delivered through the three-way tap by depressing the syringes (ideally coinciding with the animal inspiring), aiming to expel the entire drug quantity from the tap. (Alternatively, 2×3 ml of air is delivered using Penn Century dry powder insufflator device.) After dosing, the needle and tap or device are removed from the airway, and the tap closed off to prevent any retained drug leaving the tap.

After dosing with either wet suspension or dry powder, the animals are then removed from the table and observed constantly until they have recovered from the effects of anaesthesia. The animals are returned to the holding cages and given free access to food and water; they are observed and any unusual behavioural changes noted.

Exposure to LPS: About 2 hours after i.t. dosing with vehicle control or the PDE4 inhibitor, the rats are placed into sealed Perspex containers and exposed to an aerosol of LPS (nebuliser concentration ca. 150 µg.ml$^{-1}$=ca. 150 ug/ml) for ca. 15 minutes. Aerosols of LPS are generated by a nebuliser (DeVilbiss, USA) and this is directed into the Perspex exposure chamber. Following the 15-minute LPS-exposure period, the animals are returned to the holding cages and allowed free access to both food and water.

[In an alternative embodiment, the rats can be exposed to LPS less than 2 hours (e.g. about 30 minutes) after i.t. dosing. In another alternative embodiment, the rats can be exposed to LPS more than 2 hours (e.g. ca. 4 to ca. 24 hours) after i.t. dosing by vehicle or PDE4 inhibitor, to test whether or not the PDE4 inhibitor has a long duration of action (which is not essential).]

Bronchoalveolar lavage: About 4 hours after LPS exposure the animals are killed by overdose of sodium pentobarbitone (i.p.). The trachea is cannulated with polypropylene tubing and the lungs are lavaged (washed out) with 3×5 mls of heparinised (25 units.ml$^{-1}$) phosphate buffered saline (PBS).

Neutrophil cell counts: The Bronchoalveolar lavage (BAL) samples are centrifuged at ca. 1300 rpm for ca. 7 minutes. The supernatant is removed and the resulting cell pellet resuspended in ca. 1 ml PBS. A cell slide of the resuspension fluid is prepared by placing ca. 100 μl (ca. 100 ul) of resuspended BAL fluid into cytospin holders and then is spun at ca. 5000 rpm for ca. 5 minutes. The slides are allowed to air dry and then stained with Leishmans stain (ca. 20 minutes) to allow differential cell counting. The total cells are also counted from the resuspension. From these two counts, the total numbers of neutrophils in the BAL are determined. For a measure of PDE4-inhibitor-induced inhibition of neutrophilia, a comparison of the neutrophil count in rats treated with vehicle and rats treated with PDE4 inhibitors is conducted.

By varying the dose of the PDE4 inhibitor used in the dosing step (e.g. 0.2 or 0.1 mg of PDE4 inhibitor per kg of body weight, down to e.g. 0.01 mg/kg), a dose-response curve can be generated.

In Vivo Assay 4. Evaluation of Therapeutic Index of Orally-Administered PDE 4 Inhibitors in the Conscious Ferret 1.1 Materials The following materials can be used for these studies:

PDE4 inhibitors are prepared for oral (p.o.) administration by dissolving in a fixed volume (ca. 1 ml) of acetone and then adding cremophor to ca. 20% of the final volume. Acetone is evaporated by directing a flow of nitrogen gas onto the solution. Once the acetone is removed, the solution is made up to final volume with distilled water. LPS is dissolved in phosphate buffered saline.

1.2 Animals

Male ferrets (Mustela Pulorius Furo, weighing 1-2 kg) are transported and allowed to acclimatise for not less than 7 days. The diet comprises SDS diet C pelleted food given ad lib with Whiskers™ cat food given 3 times per week. The animals are supplied with pasteurised animal grade drinking water changed daily.

1.3 Experimental Protocol(s)

1.3.1 Dosing with PDE4 Inhibitors

PDE4 inhibitors are administered orally (p.o.), using a dose volume of ca. 1 ml/kg. Ferrets are fasted overnight but allowed free access to water. The animals are orally dosed with vehicle or PDE 4 inhibitor using a ca. 15 cm dosing needle that is passed down the back of the throat into the oesophagus. After dosing, the animals are returned to holding cages fitted with perspex doors to allow observation, and given free access to water. The animals are constantly observed and any emetic episodes (retching and vomiting) or behavioural changes are recorded. The animals are allowed access to food ca. 60-90 minutes after p.o. dosing.

1.3.2 Exposure to LPS

About thirty minutes after oral dosing with compound or vehicle control, the ferrets are placed into sealed perspex containers and exposed to an aerosol of LPS (ca. 30 μg/ml=ca. 30 ug/ml) for ca. 10 minutes. Aerosols of LPS are generated by a nebuliser (DeVilbiss, USA) and this is directed into the perspex exposure chamber. Following a 10-minute exposure period, the animals are returned to the holding cages and allowed free access to water, and at a later stage, food. General observation of the animals continues for a period of at least 2.5 hours post oral dosing. All emetic episodes and behavioural changes are recorded.

1.3.3 Bronchoalveolar Lavage and Cell Counts

About six hours after LPS exposure the animals are killed by overdose of sodium pentobarbitone administered intraperitoneally. The trachea is then cannulated with polypropylene tubing and the lungs lavaged twice with ca. 20 ml heparinised (10 units/ml) phosphate buffered saline (PBS). The bronchoalveolar lavage (BAL) samples are centrifuged at ca. 1300 rpm for ca. 7 minutes. The supernatant is removed and the resulting cell pellet re-suspended in ca. 1 ml PBS. A cell smear of re-suspended fluid is prepared and stained with Leishmans stain to allow differential cell counting. A total cell count is made using the remaining re-suspended sample. From this, the total number of neutrophils in the BAL sample is determined.

1.3.4 Pharmacodynamic Readouts

The following parameters are recorded:
a) % inhibition of LPS-induced pulmonary neutrophilia to determine the dose of PDE4 inhibitor which gives 50% inhibition (D50).
b) Emetic episodes—the number of vomits and retches are counted to determine the dose of PDE4 inhibitor that gives a 20% incidence of emesis (D20).
c) A therapeutic index (TI), using this assay, is then calculated for each PDE4 inhibitor using the following equation:

$$\text{Ferret Therapeutic index } (TI)(D20/D50) = \frac{D20 \text{ incidence of emesis in ferret}}{D50 \text{ inhibition of neutrophilia in ferret}}$$

It is noted that the Ferret Therapeutic index (TI) (D20/D50) calculated using this in vivo Assay 4 is often substantially different to, and for example is often substantially lower than, the Rat TI (50/50) calculated using the rat oral inflammation and pica feeding Assays 1+2.

All publications, including but not limited to patents and patent applications, cited in this specification are herein incorporated by reference as if each individual publication were specifically and individually indicated to be incorporated by reference herein as though fully set forth.

EXAMPLES

The various aspects of the invention will now be described by reference to the following examples. These examples are merely illustrative and are not to be construed as a limitation of the scope of the present invention. In this section, "Intermediates" represent syntheses of intermediate compounds intended for use in the synthesis of the "Example(s)". "Examples" are generally exemplary compounds or salts of the invention, for example the compound of formula (I) or salts thereof. The "Composition Examples" are non-limiting illustrations of the pharmaceutical compositions of the invention.

Abbreviations used herein:
DCM dichloromethane
DIPEA diisopropylethyl amine ($^i$Pr$_2$NEt)
DMF dimethyl formamide
DMSO dimethyl sulfoxide
EDC 1-(3-Dimethylaminopropyl)-3-ethylcarbodiimide hydrochloride
EtOAc ethyl acetate
EtOH ethanol
h hours HATU O-(7-Azabenzotriazol-1-yl)-N,N,N',N'-tetramethyluronium hexafluorophosphate
HCl hydrogen chloride or hydrochloric acid
HOBT hydroxybenzotriazole=1-hydroxybenzotriazole
M molarity, or moles per litre
MeCN acetonitrile
MeOH methanol
NaHCO$_3$ sodium bicarbonate
NaOH sodium hydroxide
Na$_2$SO$_4$ sodium sulfate
KOH potassium hydroxide
THF tetrahydrofuran
HPLC high pressure liquid chromatography
SPE solid phase extraction
NMR nuclear magnetic resonance (in which: s=singlet, d=doublet, t=triplet, q=quartet, dd=doublet of doublets, m=multiplet, br=broad, H=no. of protons)
LCMS liquid chromatography/mass spectroscopy
TLC thin layer chromatography
h hours
T$_{RET}$ retention time (generally from LCMS)
Room (ambient) temperature: this is usually in the range of about 20 to about 25° C.

General Experimental Details

Machine Methods Generally Used Herein:
  LCMS (Liquid Chromatography/Mass Spectroscopy)
  Waters ZQ mass spectrometer operating in positive ion electrospray mode, mass range 100-1000 amu.
UV wavelength: 215-330 nM
Column: 3.3 cm×4.6 mm ID, 3 µm ABZ+PLUS
Flow Rate: 3 ml/min
Injection Volume: 5 µl
Solvent A: 95% acetonitrile+0.05% formic acid
Solvent B: 0.1% formic acid+10 mMolar ammonium acetate
Gradient: 0% A/0.7 min, 0-100% A/3.5 min, 100% A/1.1 min, 100-0% A/0.2 min
  It should be noted that retention times (T$_{RET}$) quoted herein may vary slightly (+/−0.1 min.) when samples are run on different Waters machines, even when the same type of column and identical flow rates, injection volumes, solvents and gradients are used.

LCMS (Liquid Chromatography/Mass Spectroscopy) (for Intermediates 2A, 3A, 4A and 5A, and Example 1B Only)
Agilent 1100 mass spectrometer operating in positive ion electrospray mode, mass range 100-700 amu.
UV wavelength: 214-254 nM
Column: 2.1 cm×50 mm ID, 5 µm Zorbax
Flow Rate: 1 ml/min
Injection Volume: 1 µl
Solvent A: water+0.02% trifluoroacetic acid
Solvent B: acetonitrile+0.018% trifluoroacetic acid
Gradient: 10-80% A/3.0 min, 80% A/1.2 min, 80-10% A/1.0 min Mass Directed Autoprep HPLC
Prep. column: a Supelcosil ABZplus (10 cm×2.12 cm) (usually 10 cm×2.12 cm×5 µm).
UV wavelength: 200-320 nM
Flow: 20 ml/min
Injection Volume: 1 ml; or more preferably 0.5 ml
Solvent A: 0.1% formic acid
Solvent B: 95% acetonitrile+5% formic acid; or more usually 99.95% acetonitrile+0.05% formic acid
Gradient: 100% A/1 min, 100-80% A/9 min, 80-1% A/3.5 min, 1% A/1.4 min, 1-100% A/0.1 min Autoprep Gilson Reverse-Phase HPLC (for Example 1B)
Prep column: YMC ODS-A (50 mm×50 mm)
UV wavelength: 215-254 nM
Flow: 70 ml/min
Injection Volume: 3 ml
Solvent A: water
Solvent B: acetonitrile
Gradient: 35-95% B/5 min Chiral Columns for Chromatographic Purification ChiralPak AS columns can be obtained from:
Chiral Technologies Europe Sarl, Illkirch, France (Telephone: +33 (0)388795200; (cte@chiral.fr; www.chiral.fr).

Intermediates and Examples

Reagents not detailed in the text below are usually commercially available from chemicals suppliers, e.g. established suppliers such as Sigma-Aldrich. The addresses and/or contact details of the suppliers for some of the starting materials mentioned in the Intermediates and Examples below or the Assays above, or suppliers of chemicals in general, are as follows:
  Aldrich (catalogue name), Sigma-Aldrich Company Ltd., Dorset, United Kingdom, telephone: +44 1202 733114; Fax: +44 1202 715460; ukcustsv@eurnotes.sial.com; or
  Aldrich (catalogue name), Sigma-Aldrich Corp., P.O. Box 14508, St. Louis, Mo. 63178-9916, USA; telephone: 314-771-5765; fax: 314-771-5757; custserv@sial.com; or
  Aldrich (catalogue name), Sigma-Aldrich Chemie GmbH, Munich, Germany; telephone: +49 89 6513 0; Fax: +49 89 6513 1169; deorders@eurnotes.sial.com.
  AstaTech, Inc., 8301 Torresdale Ave., 19C, Philadelphia, Pa. 19136, USA
  Fluka Chemie AG, Industriestrasse 25, P.O. Box 260, CH-9471 Buchs, Switzerland
  Lancaster Synthesis Ltd., Newgate, White Lund, Morecambe, Lancashire LA3 3DY, United Kingdom
  Trans World Chemicals, Inc., 14674 Southlawn Lane, Rockville, Md. 20850, USA

| Table of Intermediates | |
|---|---|
| Intermediate No. | Name |
| 1 | Ethyl 4-chloro-1-ethyl-1H-pyrazolo[3,4-b]pyridine-5-carboxylate |
| 2, 2A | Ethyl 4-[(1-{[(1,1-dimethylethyl)oxy]carbonyl}-4-piperidinyl)amino]-1-ethyl-1H-pyrazolo[3,4-b]pyridine-5-carboxylate |
| 3, 3A | Ethyl 1-ethyl-4-(4-piperidinylamino)-1H-pyrazolo[3,4-b]pyridine-5-carboxylate hydrochloride |
| 4, 4A, 4B | Ethyl 4-{[1-(aminocarbonyl)-4-piperidinyl]amino}-1-ethyl-1H-pyrazolo[3,4-b]pyridine-5-carboxylate |
| 5, 5A | 4-{[1-(aminocarbonyl)-4-piperidinyl]amino}-1-ethyl-1H-pyrazolo[3,4-b]pyridine-5-carboxylic acid |
| 6 | 4-chloro-1-ethyl-1H-pyrazolo[3,4-b]pyridine-5-carboxylic acid |
| 7 | 4-chloro-1-ethyl-1H-pyrazolo[3,4-b]pyridine-5-carbonyl chloride |
| 8 | 4-chloro-N-[(3,4-dimethylphenyl)methyl]-1-ethyl-1H-pyrazolo[3,4-b]pyridine-5-carboxamide |

-continued

Table of Intermediates

| Intermediate No. | Name |
|---|---|
| 9 | 1,1-dimethylethyl [1-(aminocarbonyl)-4-piperidinyl]carbamate |
| 10 | 4-amino-1-piperidinecarboxamide hydrochloride |

Intermediate 1

Ethyl 4-chloro-1-ethyl-1H-pyrazolo[3,4-b]pyridine-5-carboxylate

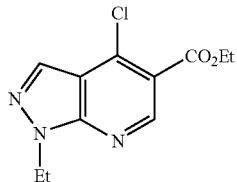

A mixture of 5-amino-1-ethyl pyrazole (806 g) (e.g. commercially available from Aldrich) and diethyl ethoxymethylenemalonate (1621 ml) (e.g. commercially available from Aldrich) was stirred and heated at 160° C. under nitrogen, in a 5 litre flask fitted with a Dean-Stark apparatus, for 1.5 h. Ethanol that distilled out of the reaction mixture (320 ml) was collected in the Dean-Stark apparatus. The reaction mixture was stirred and heated at 160° C., under nitrogen, for a further 6 h, cooled to room temperature and divided into two batches (1200 ml+1000 ml: "Batch 1" and "Batch 2"). The first (1200 ml) batch ("Batch 1") was divided into two roughly equal portions. Phosphorus oxychloride (1.85 liters) was added to each portion. The reaction mixtures were then heated at reflux in two 5l flasks for 13 h. Excess phosphorus oxychloride was distilled from both flasks under reduced pressure. The residues were cooled to room temperature, then the contents of both flasks were poured slowly onto one portion (10 kg) of crushed ice. The mixture was stirred for 15 min and then extracted with diethyl ether (3×2.5 liters). The combined organics were washed with water (2 liters) and brine (2×2 liters), then dried over $Na_2SO_4$. Evaporation of the solvent afforded the crude Intermediate 1 as a brown oil (865 g) which solidified immediately on cooling. An identical procedure was used to prepare a further 710 g of crude Intermediate 1 as a solid from "Batch 2" using 3.1 liters of phosphorus oxychloride; i.e. a total of 1575 g of crude Intermediate 1 was isolated as a solid. This solid (430 g) was dissolved in hexane (4.3 liters, i.e. 10 vols.) by heating to 50° C. with stirring. Activated charcoal (64.5 g) was added. The mixture was stirred at 50° C. for 1.0 h, then filtered through a celite bed. The celite bed was washed with hexane (2×430 ml). The combined filtrate and the washings were concentrated to about 950 ml and left to stand at 10-15° C. overnight. The resultant suspension was filtered. The residual solid was washed with chilled hexane (3×215 ml slurry wash, plus 2×400 ml displacement wash) and dried to give Intermediate 1 (280 g) as a pale yellow solid. The combined mother liquor and the washings were concentrated to about 300 ml, then cooled and left to stand at 10-15° C. overnight to afford an additional 30 g of Intermediate 1. LCMS showed $MH^+=254$; $T_{RET}=3.09$ min.

Intermediate 2

Ethyl 4-[(1-{[(1,1-dimethylethyl)oxy]carbonyl}-4-piperidinyl)amino]-1-ethyl-1H-pyrazolo[3,4-b]pyridine-5-carboxylate

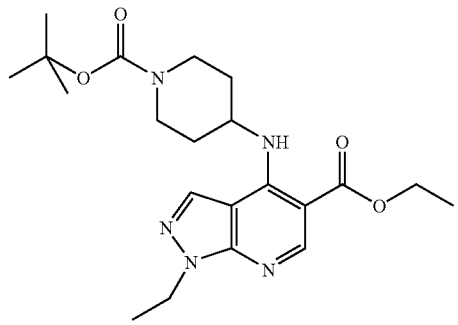

A solution of Intermediate 1 (0.5 g, 2 mmol), 1,1-dimethylethyl 4-amino-1-piperidinecarboxylate (0.59 g, 2.9 mmol) (e.g. available from AstaTech) and DIPEA (0.87 ml, 5 mmol, 2.5 equivalents) in MeCN (15 ml) was heated at reflux for 18 h. The reaction mixture was cooled. The solvent was removed under reduced pressure and the residue was partitioned between DCM (50 ml) and saturated $NaHCO_3$ solution (40 ml). The organic fraction was collected through a hydrophobic frit and concentrated under reduced pressure. The residue was purified by passing through a 100 g silica cartridge, using a gradient of 0% to 100% EtOAc in cyclohexane as the eluent, and the fractions containing the product were concentrated under reduced pressure to yield Intermediate 2 as a solid (0.74 g). LCMS showed $MH^+=418$; $T_{RET}=3.43$ min.

Alternative optional synthesis: A solution of Intermediate 1 (2.3 g) and 1,1-dimethylethyl 4-amino-1-piperidinecarboxylate (2 g) in MeCN (50 ml) and DIPEA (8.6 ml) (optionally also with about 1.5-2 ml EtOH) is heated, for example at 85° C. or 90° C., for 16 h. The solvents are removed under reduced pressure and the residue is partitioned between DCM (e.g. about 65 ml) and water (e.g. about 30 ml). The organic fraction is collected through a hydrophobic frit and the solvents are removed under reduced pressure to yield Intermediate 2.

Intermediate 3

Ethyl 1-ethyl-4-(4-piperidinylamino)-1H-pyrazolo[3,4-b]pyridine-5-carboxylate hydrochloride

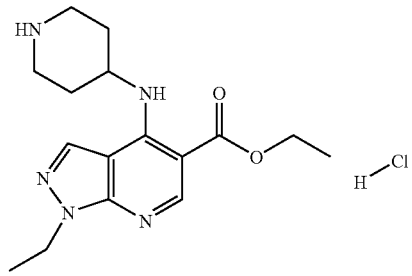

Intermediate 2 (4.1 g) was treated with 4.0 M hydrogen chloride in 1,4-dioxane (30 ml) and the reaction mixture was stirred at 22° C. for 1 h. The solvents were removed to give Intermediate 3 as a white solid (4.0 g). LCMS showed MH$^+$=318; T$_{RET}$=2.1 min.

Intermediate 4

Ethyl 4-{[1-(aminocarbonyl)-4-piperidinyl]amino}-1-ethyl-1H-pyrazolo[3,4-b]pyridine-5-carboxylate

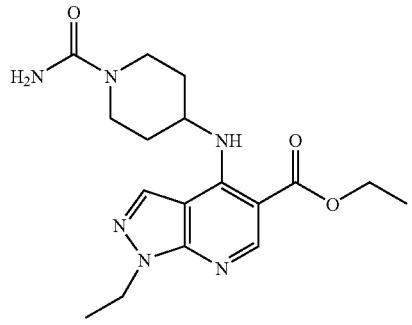

A suspension of Intermediate 3 (4 g) in THF (100 ml) was treated with DIPEA (2.6 ml) followed by trimethylsilyl isocyanate (1.99 ml, 1.7 g) and the solution was stirred at 22° C. for 2 h. The volatile solvents were removed under reduced pressure and the residue was partitioned between DCM (e.g. 50 ml) and water (e.g. 25 ml). The organic and aqueous layers were separated. The aqueous phase was extracted with DCM (e.g. 50 ml). The organic layers were combined, separated from water by passing through a hydrophobic frit and concentrated under reduced pressure to yield Intermediate 4 as a solid (4 g). LCMS showed MH$^+$=361; T$_{RET}$=2.45 min.

Intermediate 5

4-{[1-(aminocarbonyl)-4-piperidinyl]amino}-1-ethyl-1H-pyrazolo[3,4-b]pyridine-5-carboxylic acid

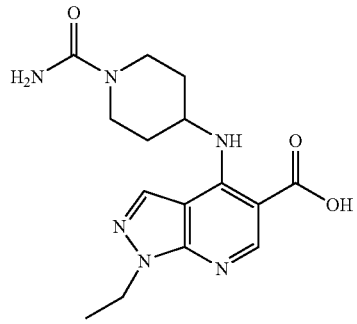

A solution of Intermediate 4 (4 g) in EtOH (50 ml) was treated with a solution of NaOH (1.77 g) in water (20 ml) and the reaction mixture was heated at 60° C. for 5 h. The solvents were removed and the residue was dissolved in water (ca. 8 ml), the pH was adjusted to 3 (2M HCl) and the resultant precipitate was collected by filtration and dried at 60° C. under vacuum. LCMS indicated that partial hydrolysis of the piperidine urea to the piperidine had occurred. Therefore, the precipitate from the reaction was dissolved in EtOH (100 ml), the solution was treated with trimethylsilyl isocyanate (3 ml) and DIPEA (10 ml) and then stirred at room temperature overnight. The solvents were removed, water was added to the residue, the pH was adjusted to 3 (2M HCl), the mixture was cooled to 0° C. for 30 minutes, and the resultant precipitate was collected by filtration and dried to give Intermediate 5 as a white solid (2.66 g). LCMS showed MH$^+$=333; T$_{RET}$=2.0 min.

Intermediate 6

4-chloro-1-ethyl-1H-pyrazolo[3,4-b]pyridine-5-carboxylic acid

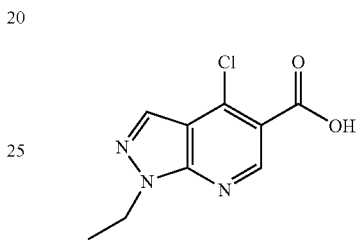

A solution of Intermediate 1 (20.0 g, 78.8 mmol) in 1,4-dioxane (100 ml) was treated with a solution of KOH (18 g of pellets) in water (30 ml) and the reaction mixture was stirred at room temperature for 24 h. The solvent was evaporated and the residue was acidified to pH3 (2M hydrochloric acid). The resultant white precipitate was collected by filtration and dried under vacuum overnight to give Intermediate 6 as a white solid (16.9 g). LCMS showed MH$^+$=226; T$_{RET}$=2.61 min.

Intermediate 7

4-chloro-1-ethyl-1H-pyrazolo[3,4-b]pyridine-5-carbonyl chloride

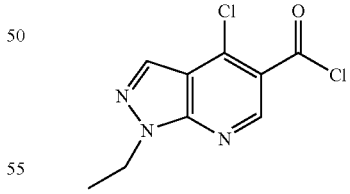

A solution of Intermediate 6 (17.8 g, 78.8 mmol) in thionyl chloride (SOCl$_2$, 100 ml) was heated at reflux under nitrogen for 3.5 h. The solution was allowed to cool to room temperature overnight. The thionyl chloride was removed in vacuo, any remaining thionyl chloride was removed in vacuo by azeotropic distillation with toluene (ca. 30 ml), and this was repeated to remove thionyl chloride, to give Intermediate 7 as a beige solid (16.86 g). LCMS (in MeOH, hence methyl ester) showed MH$^+$=240 (MH$^+$ for methyl ester); T$_{RET}$=2.88 min.

Intermediate 8

4-chloro-N-[(3,4-dimethylphenyl)methyl]-1-ethyl-1H-pyrazolo[3,4-b]pyridine-5-carboxamide

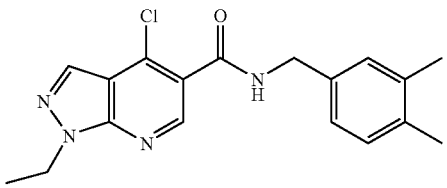

A solution of Intermediate 7 (6 g) and DIPEA (3.17 g) in THF (60 ml) was stirred for 20 min. A one-third aliquot (20 ml) of the resultant solution was added to 3,4-dimethyl-benzylamine (1.11 g) (e.g. available from Trans World Chemicals). The reaction mixture was stirred under nitrogen at room temperature for 24 h, more THF (20 ml) being added to aid dissolution of the reactants. The solvent was removed in vacuo and the residue was partitioned between DCM (50 ml) and 5% citric acid solution (50 ml). The organic layer was separated using a hydrophobic frit, washed with 0.5M NaHCO$_3$ solution (50 ml), dried (Na$_2$SO$_4$), filtered and concentrated in vacuo to give Intermediate 8 as a white powder (2.39 g). LCMS showed MH$^+$=343; T$_{RET}$=3.34 min.

Intermediate 9

1,1-dimethylethyl [1-(aminocarbonyl)-4-piperidinyl]carbamate

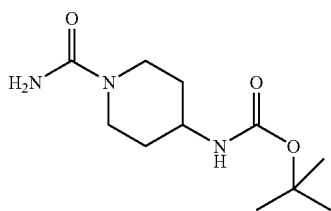

A solution of 1,1-dimethylethyl 4-piperidinylcarbamate (0.35 g) (e.g. available from AstaTech) in DCM (10 ml) was treated with trimethylsilyl isocyanate (1.1 ml, 0.86 g). The reaction mixture was stirred at room temperature for 8 h and then left to stand at room temperature over the weekend. The mixture was diluted with DCM (10 ml) and washed with saturated NaHCO$_3$ solution (20 ml). The organic phase was separated and collected through a hydrophobic frit. The aqueous phase was extracted with DCM. The organics were combined and evaporated to dryness to give Intermediate 9 as a white foam (0.29 g). $^1$H NMR (400 MHz in CDCl$_3$, 27° C., δ ppm) 4.45 (br. s, 3H), 3.90 (d, 2H), 3.65 (br. m, 1H), 2.9-3.0 (dt, 2H), 1.95-2.0 (br. dd, 2H), 1.45 (s, 9H), 1.3-1.4 (dq, 2H).

Intermediate 10

4-amino-1-piperidinecarboxamide hydrochloride

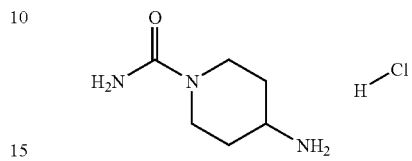

Intermediate 9 (0.29 g) was treated with a 4M solution of hydrogen chloride in 1,4-dioxane (5 ml), and was stirred at room temperature for 4 h. The reaction mixture was evaporated to dryness and co-evaporated with DCM to give a white foam. This was triturated with diethyl ether and a small amount (a few drops) of MeOH and the resulting white solid was filtered off and dried by suction to give Intermediate 10 as a white solid (0.27 g, impurities present). $^1$H NMR (400 MHz in d$_6$-DMSO, 27° C., δ ppm) 8.1 (br. s, 2H), 3.95 (d, 2H), 3.15 (m, 1H), 2.7 (dt, 2H), 1.85 (dd, 2H), 1.35 (m, 2H); impurities present.

Intermediate 2A

Ethyl 4-[(1-{[(1,1-dimethylethyl)oxy]carbonyl}-4-piperidinyl)amino]-1-ethyl-1H-pyrazolo[3,4-b]pyridine-5-carboxylate

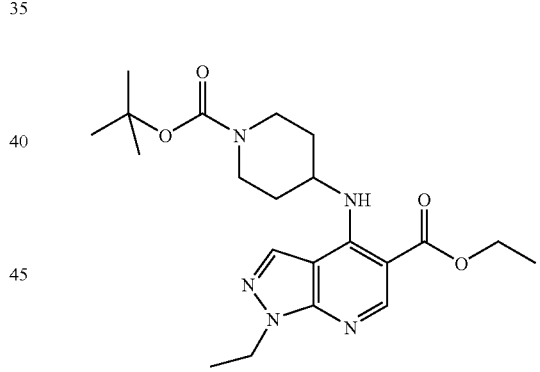

A solution of Intermediate 1 (25 g) in MeCN (565 ml) was treated with solid 1,1-dimethylethyl 4-amino-1-piperidinecarboxylate (21.7 g) and DIPEA (93.4 ml, 69.3 g). The reaction mixture was heated at 90° C. for 16 h. After cooling the reaction mixture, the solvents were removed under reduced pressure and the residue was partitioned between DCM (1100 ml) and water (800 ml). The organic fraction was dried (MgSO$_4$), was filtered and the solvents were removed under reduced pressure. The residue was subject to flash column chromatography (3:1 hexane/EtOAc) to yield Intermediate 2A as a yellow solid (39.54 g). LCMS showed MH$^+$=418; T$_{RET}$=3.13 min.

1H NMR (400 MHz, chloroform-d) δ ppm 9.44 (d, J=7.83 Hz, 1H), 8.89 (s, 1H), 7.94 (s, 1H), 4.49 (q, J=7.33 Hz, 2H), 4.35 (q, J=7.16 Hz, 2H), 3.95-4.11 (m, 3H), 3.18 (t, J=10.86 Hz, 2H), 2.10-2.20 (br d, 2H), 1.62-1.73 (m, 2H), 1.47-1.53 (m, 12H), 1.41 (t, J=7.07 Hz, 3H).

Intermediate 3A

Ethyl 1-ethyl-4-(4-piperidinylamino)-1H-pyrazolo[3,4-b]pyridine-5-carboxylate hydrochloride

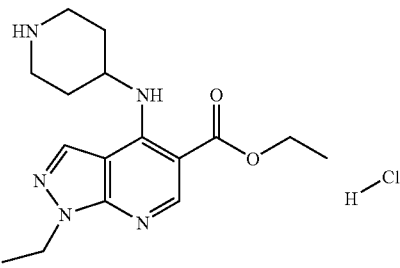

Intermediate 2A (39.54 g) was treated with 4M HCl in 1,4-dioxane (300 ml) and the reaction mixture was stirred at room temperature for 1 h. The solvents were removed and the residue subject to vacuum overnight, to give Intermediate 3A as a white solid (34.21 g, some dioxane still present; from NMR theoretically 33.5 g present excluding dioxane). LCMS showed MH$^+$=318; T$_{RET}$=1.90 min.

1H NMR (400 MHz, DMSO-d$_6$) δ ppm 9.33 (d, J=8.08 Hz, 1H), 9.21 (br s, 1H), 9.10 (br s, 1H), 8.74 (s, 1H), 8.44 (s, 1H), 4.43 (q, J=7.20 Hz, 2H), 4.32 (q, J=7.09 Hz, 2H), 3.20-3.35 (m, 4H), 2.23 (d, J=11.62 Hz, 2H), 1.76-1.87 (m, 2H), 1.38 (q, J=7.20 Hz, 3H), 1.34 (q, J=7.09 Hz, 3H).

Intermediate 4A

Ethyl 4-{[1-(aminocarbonyl)-4-piperidinyl]amino}-1-ethyl-1H-pyrazolo[3,4-b]pyridine-5-carboxylate

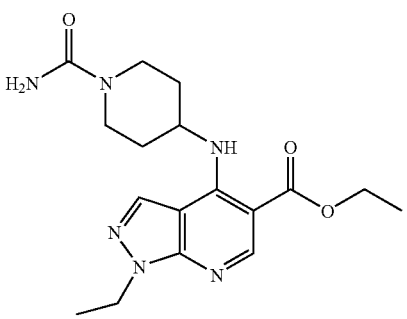

A suspension of Intermediate 3A (theoretical 33.5 g excluding dioxane present) in THF (880 ml) was treated with trimethylsilyl isocyanate (17.5 ml, 14.9 g) followed by DIPEA (22.6 ml, 16.8 g) and the solution was stirred at room temperature for 5 h. LCMS indicated formation of only a small amount of product, so more DIPEA (22.6 ml) was added and the mixture was stirred for an additional 24 h. The THF was removed under reduced pressure. The residue was dissolved/diluted in DCM (1000 ml), was washed with brine (200 ml), was dried (MgSO$_4$) and was evaporated under reduced pressure to give a residue which from LCMS appeared to contain a small amount of product.

The residue was dissolved in DCM (1000 ml), was treated with trimethylsilyl isocyanate (17.5 ml) followed by DIPEA (22.6 ml) and the solution was stirred at room temperature for 48 h. Trimethylsilyl isocyanate (17.5 ml, 14.9 g) followed by DIPEA (22.6 ml, 16.8 g) were again added and the solution was stirred at room temperature for an additional 48 h. The volatile solvents were removed under reduced pressure and the residue was dissolved in DCM (600 ml) and washed with brine (2×200 ml). The organic layer was dried (MgSO$_4$), was filtered and was concentrated under reduced pressure. The solid residue was stirred in diethyl ether (1000 ml) for 2 h until pulverized and was collected by filtration to yield Intermediate 4A as a light-yellow solid (24.56 g). LCMS showed MH$^+$=361; T$_{RET}$=2.19 min. m.p.=126-127° C.

1H NMR (400 MHz, chloroform-d) δ ppm 9.48 (d, J=7.83 Hz, 1H), 8.90 (s, 1H), 7.95 (s, 1H), 4.65 (s, 2H), 4.50 (q, J=7.24 Hz, 2H), 4.35 (q, J=7.12 Hz, 2H), 4.1-4.2 (m, 1H), 3.87-3.93 (m, 2H), 3.26 (ddd, J=13.58, 10.17, 3.03 Hz, 2H), 2.16-2.23 (m, 2H), 1.70-1.80 (m, 2H), 1.51 (t, J=7.24 Hz, 3H), 1.41 (t, J=7.12 Hz, 3H).

Intermediate 4B

Ethyl 4-{[1-(aminocarbonyl)-4-piperidinyl]amino}-1-ethyl-1H-pyrazolo[3,4-b]pyridine-5-carboxylate

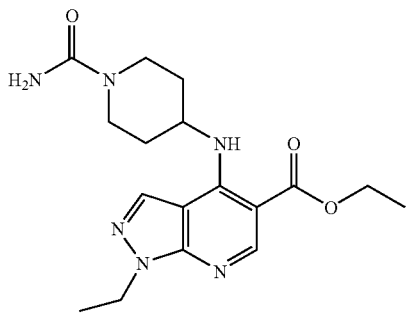

A suspension of ethyl 1-ethyl-4-(4-piperidinylamino)-1H-pyrazolo[3,4-b]pyridine-5-carboxylate hydrochloride (13 g, 36.77 mmol) (e.g. Intermediate 3) in DCM (300 ml) was treated with trimethylsilyl isocyanate (5 g) followed by DIPEA (10 ml) and was stirred at 22° C. for 3 h. The mixture was diluted with water, the organic layer was separated from the aqueous layer by passing through a hydrophobic frit, and the solvents were removed from the organic layer to give Intermediate 4B (10 g). LCMS showed MH$^+$=361; T$_{RET}$=2.6 min.

Intermediate 5A

4-{[1-(aminocarbonyl)-4-piperidinyl]amino}-1-ethyl-1H-pyrazolo[3,4-b]pyridine-5-carboxylic acid

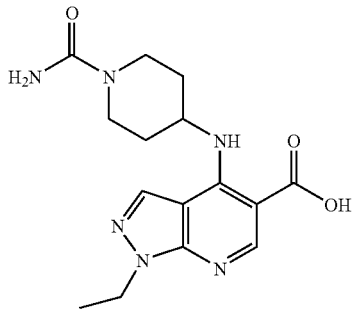

A solution of Intermediate 4A (24.26 g) in EtOH (360 ml) and water (120 ml) was treated with lithium hydroxide monohydrate (11 g) and the reaction mixture was stirred at room temperature overnight. The EtOH was removed under reduced pressure. Aqueous 1N HCl solution (300 ml) was added to the residue and the resultant precipitate was cooled in an ice bath for 1 h, was collected by filtration, washed with cold water, dried in a vacuum dessicator overnight, and then further dried in a vacuum oven under reduced pressure at 60° C. overnight to give Intermediate 5A as a white solid (22.4 g). LCMS showed MH$^+$=333; T$_{RET}$=1.23 min. m.p.=204-206° C.

1H NMR (400 MHz, DMSO-d$_6$) δ ppm 9.50 (d, J=8.08 Hz, 1H), 8.69 (s, 1H), 8.25 (s, 1H), 6.04 (br s, 2H), 4.37 (q, J=7.20 Hz, 2H), 4.14-4.24 (m, 1H), 3.80 (d, J=13.64 Hz, 2H), 3.15 (t, J=10.86 Hz, 2H), 1.96-2.03 (m, 2H), 1.39-1.47 (m, 2H), 1.37 (t, J=7.20 Hz, 3H).

EXAMPLES

Example 1

4-{[1-(aminocarbonyl)-4-piperidinyl]amino}-N-[(3,4-dimethylphenyl)methyl]-1-ethyl-1H-pyrazolo[3,4-b]pyridine-5-carboxamide

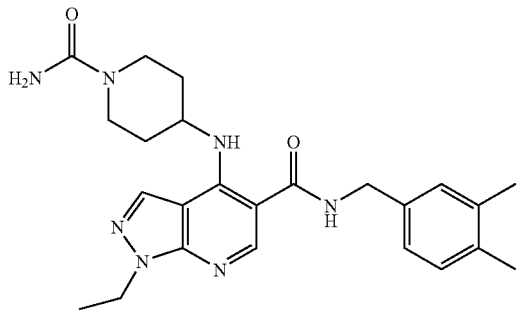

A solution of Intermediate 5 (100 mg, 0.3 mmol) in dry DMF (e.g. can be about 1 ml) was treated with EDC (63 mg, 0.33 mmol), HOBT (45 mg, 0.33 mmol) and DIPEA (0.13 ml, 0.75 mmol). 10 minutes later, 3,4-dimethyl-benzylamine (47 microliters, 0.33 mmol) (e.g. available from Trans World Chemicals Inc.) was added and the resulting solution was left to stand at room temperature overnight. The DMF was removed by evaporation and the residue was partitioned between DCM and saturated aqueous NaHCO$_3$ solution. The organic layer was collected through a hydrophobic frit and was concentrated in vacuo to dryness. The residue was purified by passing through a 20 g silica SPE cartridge, using firstly a gradient of EtOAc and cyclohexane (increasing concentration of EtOAc) and then a step gradient of EtOAc and methanol as the eluent. The product was eluted in the fraction containing 4:1 EtOAc:MeOH. The solvents were removed in vacuo to give a white solid (101 mg). NMR showed the presence of EtOAc and DCM, so the solid was dried in vacuo at 40° C. to give Example 1 (80 mg). LCMS showed MH$^+$=450; T$_{RET}$=2.80 min.

$^1$H NMR (400 MHz in d$_6$-DMSO, 27° C., δ ppm) 9.9 (d, 1H), 8.93 (t, 1H), 8.61 (s, 1H), 8.19 (s, 1H), about 7.08 (s, 1H), 7.07 (d, 1H), 7.02 (d, 1H), 5.98 (s, 2H), 4.33-4.39 (m, 4H), 4.08-4.18 (br m, 1H), 3.75 (dt, 2H), 3.13 (td, 3H), 2.19 (s, 3H), 2.18 (s, 3H), 1.92-2.00 (m, 2H), 1.33-1.42 (m, 5H). Plus some other peaks: possibly solvent.

A similar alternative method is: A solution of Intermediate 5 (0.066 mmol) in DMF (1 ml) is treated with EDC (0.066 mmol), HOBT (0.066 mmol) and DIPEA (0.151 mmol) followed by 3,4-dimethylbenzylamine (0.066 mmol). The reaction mixture is left to stand at 22° C. for 16 h. The DMF is evaporated and the residue is partitioned between DCM (5 ml) and saturated aqueous NaHCO$_3$ solution (2 ml). The organic layer is collected through a hydrophobic frit and evaporated. The residue is purified by mass directed autoprep. HPLC to give the title compound.

Example 1A

4-{[1-(aminocarbonyl)-4-piperidinyl]amino}-N-[(3,4-dimethylphenyl)methyl]-1-ethyl-1H-pyrazolo[3,4-b]pyridine-5-carboxamide

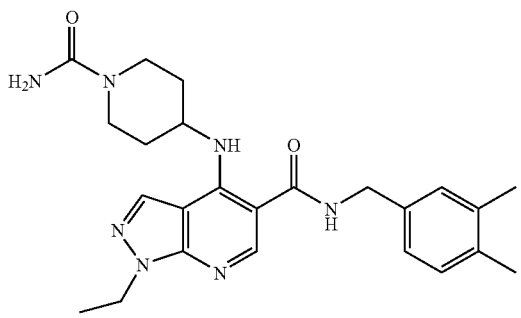

A mixture of Intermediate 8 (27 mg, 0.08 mmol), Intermediate 10 (16 mg, 0.088 mmol) and DIPEA (35 microliters, 0.2 mmol) in MeCN (2 ml) was heated at reflux for 18 h. More of Intermediate 10 (0.5 mole equivalents, ca. 0.04 mmol, ca. 7 mg) was added. The reaction mixture was heated at reflux for a further 24 h, cooled to room temperature and the solvent removed in vacuo. The residue was partitioned between DCM and water. The organic phase was collected through a hydrophobic frit and evaporated to dryness. LCMS indicated that there were two products of the same molecular weight.

Therefore, the residue was purified by mass directed autopreparative HPLC to give the title compound as Example 1A (4.4 mg); LCMS showed MH$^+$=450 and T$_{RET}$=2.79 min.

The other undesired product having the same molecular weight as Example 1A was also isolated from the mass directed autopreparative HPLC (0.6 mg); and for this compound LCMS showed MH$^+$=450 and T$_{RET}$=2.69 min.

Example 1B

4-{[1-(aminocarbonyl)-4-piperidinyl]amino}-5-{[(3,4-dimethylphenyl)methyl]aminocarbonyl}-1-ethyl-1H-pyrazolo[3,4-b]pyridine

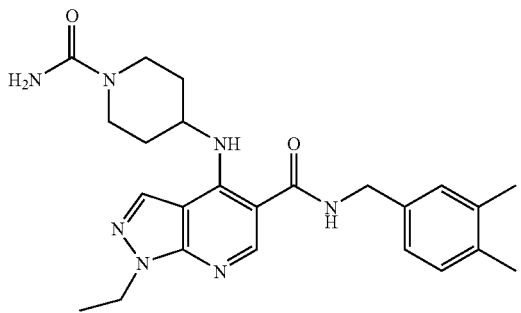

A solution of Intermediate 5A (21.6 g) in DMF (300 ml) was treated with 3,4-dimethyl benzylamine (9.71 ml, 9.23 g), HOBT (9.66 g) and DIPEA (25 ml, 18.5 g) followed by EDC (14.1 g). The reaction mixture was stirred at room temperature overnight. The DMF was evaporated under reduced pressure at 40° C. and the residue was partitioned between EtOAc (300 ml) and water (200 ml). The organic layer was separated and the aqueous phase was extracted with EtOAc (2×100 ml). The combined organic extracts were washed with brine (200 ml), were dried (MgSO$_4$), were filtered and were evaporated under reduced pressure.

The residue was purified by flash column chromatography on silica gel (1500 ml) using 95:5 DCM/MeOH as the eluting solvent. The purest fractions were collected and evaporated under reduced pressure. The residue was dissolved in EtOAc (500 ml), was washed with 1N NaOH solution (100 ml), was dried (MgSO$_4$), was filtered, was evaporated, and the residue was dried at 60° C. in a vacuum oven overnight to provide the title compound as a pale yellow solid (12.5 g).

The remaining fractions from the flash column chromatography were collected and purified by autoprep. HPLC (Gilson reverse-phase HPLC, Solvent A water, Solvent B acetonitrile, see above for details). The water-acetonitrile fractions containing the product (UV detection) were combined, and the acetonitrile solvent was removed under reduced pressure. The remaining water was decanted off from the residue, and the residue was evaporated to dryness. The solid was collected and washed with ether to give the title compound as a pale yellow solid (6 g).

The two batches of product were combined, were dissolved in MeOH and were evaporated under reduced pressure to provide the title compound Example 1B as a pale yellow solid.

LCMS showed MH$^+$=450; T$_{RET}$=2.45 min. m.p.=152-154° C.

1H NMR (400 MHz, DMSO-d$_6$) δ ppm 10.01 (d, J=7.83 Hz, 1H), 8.97 (t, J=5.81 Hz, 1H), 8.63 (s, 1H), 8.21 (s, 1H), 7.02-7.10 (m, 3H), 6.01 (br s, 2H), 4.34-4.42 (m, 4H), 4.10-4.20 (m, 1H), 3.71-3.81 (m, 2H), 3.14 (t, J=10.74 Hz, 2H), 2.20 (s, 3H), 2.18 (s, 3H), 1.92-2.02 (m, 2H), 1.35-1.45 (m, 5H). Plus peaks due to ether.

Example 2

4-{[1-(aminocarbonyl)-4-piperidinyl]amino}-5-{[(3,4-dimethylphenyl)methyl]aminocarbonyl}-1-ethyl-1H-pyrazolo[3,4-b]pyridine hydrochloride

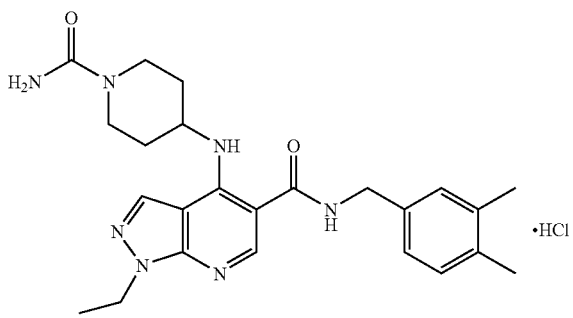

A solution of Example 1B (15 mg) in MeOH (0.5 ml) was treated with a solution of 1N hydrogen chloride in ether (10 ml). The mixture was evaporated to provide the title compound as a white solid (16 mg). m.p.=217-218° C. (decomposition).

1H NMR (400 MHz, DMSO-d$_6$) δ ppm 10.84 (s, 1H), 9.48 (s, 1H), 8.77 (s, 1H), 8.46 (s, 1H), 7.05-7.14 (m, 3H), about 6.0-6.6 (br s, 2H), 4.53 (q, J=7.12 Hz, 2H), 4.40 (d, J=5.56 Hz, 2H), 4.27 (br s, 1H), 3.76 (d, J=13.64 Hz, 2H), 3.13-3.23 (t, J=10.95 Hz, 2H), 2.21 (s, 3H), 2.19 (s, 3H), 1.94-2.03 (m, 2H), 1.44-1.53 (m, 2H), 1.40 (t, J=7.17 Hz, 3H).

Pharmaceutical Composition Examples and Micronisation Examples

Examples of Pharmaceutical Compositions Suitable for External Topical Administration Composition Examples C1, C1A and C1B (Ointments)

Exemplary pharmaceutical compositions being ointments suitable for external topical administration are as follows:

| Ingredients (+preferable specifications *) | Function | Example C1: Ingredient Concentration (% w/w) | Alternative Example C1A: Ingredient Concentration (% w/w) | Alternative Example C1B: Concentration range (% w/w) |
|---|---|---|---|---|
| Compound of formula (I) ("drug") (as free base) | Active agent PDE4 inhibitor | 0.5 | 0.5 | 0.1 to 3% (e.g. 0.2 to 1.5%) |
| White Petrolatum (white soft paraffin) (e.g. USP) | Wax/ ointment base | 69.65 | 69.16 | 25 to 75% (e.g. 45 to 75%) |
| Mineral Oil (e.g. USP or BP) | Solubilizer/ emollient | 4.975 | 5 | 2.5 to 15% (e.g. 4 to 12%) |
| Polyoxyl Stearyl Ether (e.g. Volpo S-2 ™) | Surfactant | 4.975 | 5 | 0.5 to 10% (e.g. 3 to 10%) |

-continued

| Ingredients (+preferable specifications *) | Function | Example C1: Ingredient Concentration (% w/w) | Alternative Example C1A: Ingredient Concentration (% w/w) | Alternative Example C1B: Concentration range (% w/w) |
|---|---|---|---|---|
| Propylene Glycol (e.g. USP) | Solubilizer/ Penetration Enhancer | 19.90 | 20 | 0.5 to 50% (e.g. 5 to 50% or 7 to 30%) |
| Butylated Hydroxyanisole (e.g. NF or BP) | Antioxidant | 0 | 0.20 | 0%, or 0.001 to 2% (e.g. 0.02 to 2%) |
| Methylparaben (e.g. NF) | Preservative | 0 | 0.11 | 0%, or 0.05 to 2% |
| Propylparaben (e.g. NF) | Preservative | 0 | 0.03 | 0%, or 0.01 to 2% |
| Total | | 100 | 100 | |

* NF = National Formulary; USP = US Pharmacopeia; BP = British Pharmacopeia

Composition Example C1 can be prepared by the following method:

The white petrolatum (white soft paraffin) (140 g), the mineral oil (10 g), and the polyoxyl stearyl ether (e.g. Volpo S-2™) (10 g) are mixed together and melted using a hot water bath until all the ingredients are dissolved, to form an oil phase. The oil phase is heated to ca. 65-70° C. The propylene glycol (40 g) is heated using a hot water bath to a temperature of ca. 65-70° C., and is then added slowly to the oil phase under low homogenization stirring conditions (Polytron large shaft). The homogenization is then increased and the mixture is homogenized for 10 mins. The resulting formulation is then cooled to room temperature, using a cold water bath to facilitate cooling, to give an ointment formulation (ca. 200 g).

Approx. 5 g of the ointment formulation in a vial is heated slowly in a hot water bath until the ointment reaches a temperature of approximately 40-45° C. The compound of formula (I) ("drug", in free base form, 25.3 mg) is added slowly into the vial and then the resulting mixture is homogenized using a microhomogenizer for approx. 10 minutes, to give an ointment containing the drug (Composition Example C1). The drug is typically at least partly in suspension in the ointment.

Composition Example C1A (and/or alternative Composition Example C1B) can be prepared by the following method:

The ointment formulation is manufactured by first preparing the propylene glycol phase. The propylene glycol and the appropriate amount of the drug are mixed to provide an initial solution while stirring with a low shear propeller mixer. The antioxidant and preservatives are also included in the propylene glycol solution. The temperature of the propylene glycol solution is maintained at about 55-65° C. Concurrently, all of the components of the oil phase (white petrolatum, polyoxyl stearyl ether and mineral oil) are added into a separate container and heated to about 75-85° C. to melt and mix the components.

The propylene glycol phase is then added into the oil phase while maintaining the temperature at above 70° C. (e.g. from above 70° C. to 90° C., e.g. about 75-85° C.) and mixing with a high shear homogenizer for a minimum of 15 minutes (e.g. 15-60 minutes or 15-30 minutes). The emulsification process can be carried out in conventional topical manufacturing equipment, such as a Lee Kettle or Malt-Mat, which allows for scraping of the materials from the sides of the vessel while the phases are being emulsified.

Following the emulsification time of at least 15 minutes, the product is cooled to about 30° C., to form (semi-solidify) the ointment emulsion. During this cooling time, the homogenizer speed is reduced and low agitation is used. After the product has cooled, and the ointment is produced (Composition Example C1A or C1B), it is dispensed from the manufacturing vessel into holding containers. It can then be packed into tubes, sachets or other suitable packaging components, as necessary.

Composition Examples C2 and C2A (Water-in-Oil Cream Emulsion)

An exemplary external-topical pharmaceutical composition being a water-in-oil cream emulsion is as follows:

| Ingredients (+preferable specifications: NF = National Formulary; USP = US Pharmacopeia, etc) | Function | Example C2: Ingredient Concentration (% w/w) | Alternative Example C2A: Concentration range (% w/w) |
|---|---|---|---|
| Compound of formula (I) (as free base) ("drug") | Active | 0.5 | 0.1 to 3% (e.g. 0.2 to 1.5%) |
| White Petrolatum (e.g. USP) | Wax/ointment base | 41.34 | 25 to 75% (e.g. 30 to 65%) |
| Mineral Oil (e.g. USP or BP) | Solubilizer/ emollient | 10 | 2.5 to 15% (e.g. 4 to 12%) |
| Polyoxyl Stearyl Ether | Surfactant | 8 | 0.5 to 12% (e.g. 3 to 10%) |

-continued

| Ingredients (+preferable specifications: NF = National Formulary; USP = US Pharmacopeia, etc) | Function | Example C2: Ingredient Concentration (% w/w) | Alternative Example C2A: Concentration range (% w/w) |
|---|---|---|---|
| Propylene Glycol USP | Solubilizer/ Enhancer | 20 | 0.5 to 50% (e.g. 5 to 50%) |
| Butylated Hydroxyanisole (e.g. NF or BP) | Antioxidant | 0.02 | 0.001 to 2% (e.g. 0.02 to 2%) |
| Methylparaben (e.g. NF) | Preservative | 0.11 | 0.05 to 2% |
| Propylparaben (e.g. NF) | Preservative | 0.03 | 0.01 to 2% |
| Purified water (e.g. USP) | Vehicle | Qs (20%) | 2 to 30% (e.g. 5 to 25%) |
| Total | | 100 | |

Composition Example C2 (and/or alternative embodiment Example C2A) can for example be prepared using a process similar to that described for Composition Example C1.

For example, in one embodiment of the process, the water and propylene glycol can be mixed together (optionally with the surfactant, antioxidant and preservatives, and optionally with the drug) to form an aqueous phase. The oil phase containing the white petrolatum and mineral oil are prepared in a separate vessel. Temperatures of both the aqueous and oil phases are maintained at elevated temperatures, such as about 55-90° C. or preferably about [from above 70 to 90]° C., the oil phase temperature being sufficiently high to melt the oil phase, and while hot, one phase is added to another while mixing using a high shear mixer to effect emulsification, preferably keeping the temperature above 70° C. such as from above 70 to 90° C. The final emulsion is allowed to cool e.g. to about 18-35° C. such as about 30° C., while the agitation continues at lower speeds. The ointment can then be dispensed from the manufacturing vessel and filled into the primary packaging, for example tubes or sachets.

Composition Examples C3 and C3A (Oil-in-Water Cream Emulsion)

An exemplary external-topical pharmaceutical composition being a oil-in-water cream emulsion, and intended to be a high occlusion composition, is as follows:

| Ingredients (+optional specifications) | Function | Example C3: Ingredient Concentration (% w/w) | Alternative Example C3A: Concentration range (% w/w) |
|---|---|---|---|
| Compound of formula (I) (as free base) ("drug") | Active | 0.5 | 0.1 to 3% (e.g. 0.2 to 1.5%) |
| Mineral Oil (e.g. USP) | Solubilizer/ emollient | 32.5 | 15 to 50% (e.g. 20 to 45%) |
| Dimethicone (Silicone Fluid 360) (e.g. NF) | Emollient | 2.5 | 0.5 to 20% (e.g. 1 to 5%) |
| Isopropyl Myristate (e.g. NF) | Solubilizer | 7.5 | 0.5 to 20% (e.g. 3 to 12%) |
| Glycerol Monostearate (e.g. Arlacel 165 ™) | Surfactant | 2 | 0.5 to 10% |
| Sorbitan Monostearate (e.g. Span 60 ™) | Surfactant | 1 | 0.05 to 10% |
| Cetostearyl Alcohol (e.g. NF) | Surfactant | 2 | 0.1 to 15% (e.g. 1 to 10%) |
| Microcrystalline Wax (Ross) (e.g. NF) | Emollient/ base | 10 | 5 to 25% (e.g. 8 to 15%) |
| Propylene Glycol (e.g. USP) | Solubilizer/ Enhancer | 10 | 0.5% to 50% (e.g. 7% to 25%) |
| Citric Acid, Hydrous Granular (e.g. USP) | Buffer | 0.05 | 0.05 to 5% |
| Sodium Phosphate, Dibasic (e.g. USP) | Buffer | 0.06 | 0.05 to 5% |
| Imidurea (Germall 115 ™) (e.g. NF) | Preservative | 0.20 | 0.05 to 2% |
| Purified Water (e.g. USP) | vehicle | 32 | 15 to 60% (e.g. 20 to 50%) |

Composition Example C3 (and/or alternative embodiment Example C3A) can for example be prepared using a process generally analogous to that described in Composition Example C2 above.

Composition Example C4 (Cream Emulsion)

| Ingredients | Concentration of ingredient (% w/w) | Optional weight of ingredients (g) |
|---|---|---|
| Oil Phase | | |
| Mineral oil | 29.86 | 29.90 |
| Steareth 2 | 2 | 2.05 |
| Cetostearyl Alcohol | 2 | 2.01 |
| Arlacel 165 ™ (glycerol monostearate) | 2 | 2.10 |
| Microcrystalline wax | 10 | 10.12 |
| isopropyl myristate (IPM) | 7.5 | 7.87 |
| Dimethicone | 2.5 | 2.65 |
| Aqueous Phase | | |
| Propylene glycol | 22 | 22.09 |
| Purified water | 22 | 22.34 |
| Methylparaben | 0.11 | 0.1142 |
| Propylparaben | 0.03 | 0.0354 |

(Optional Batch size: ca. 100 g).

Procedure

Cream base without drug: The combined ingredients of the oil phase are melted in a hot water bath to a temperature of approx 60-70° C. The combined ingredients of the aqueous phase are also heated in a hot water bath to a temperature of approx. 60-70° C. The aqueous phase is then added slowly to the oil phase under low homogenization conditions and then is homogenized at a higher speed for approx. 10 mins under low heat in the water bath. With heating removed, the formulation is then stirred manually with a spatula while being allowed to cool, until room temperature is reached, giving a cream emulsion.

Cream containing drug: As a modification of the above procedure, after the aqueous phase is heated to a temperature of approx. 60-70° C. and before addition to the oil phase, the compound of formula (I) is added at 0.1% to 3% w/w or 0.2% to 1.5% w/w (e.g. 0.5% w/w) to the pre-formed hot aqueous phase. Then, the aqueous phase is added slowly to the oil phase under low homogenization conditions and then is homogenized at a higher speed for approx. 10 mins under low heat in the water bath. With heating removed, the formulation is then stirred (e.g. manually with a spatula) while being allowed to cool, until ca. 18-35° C. or ca. 18-30° C. (e.g. 30° C. or room temperature) is reached, giving a cream emulsion (Composition Example C4).

Composition Examples C5, C6, C7, C8, C9, C10, and C11 (Ointment Compositions)

Exemplary ointments can be as follows:

| Example C5 Ingredients | Ingedient % w/w | Optional ingredients weight (g) | Example C6 Ingredients | Ingedient % w/w | Optional ingredients weight (g) |
|---|---|---|---|---|---|
| Oil Phase | | | Oil Phase | | |
| White petrolatum | 60 | 60.82 | White petrolatum | 65 | 67.87 |
| Mineral oil | 5 | 5.04 | Mineral oil | 5 | 5.12 |
| Steareth-2 | 5 | 5.09 | Steareth-2 | 5 | 5.04 |
| Beeswax substitute | 10 | 10.02 | Beeswax substitute | 5 | 5.05 |
| Hydrophilic phase | | | Hydrophilic phase | | |
| Propylene glycol | 20 | 20.32 | Propylene glycol | 20 | 20.35 |
| Optional Batch size ca. 100 g | | | Optional Batch size ca. 100 g | | |

| Example C7 Ingredients | Ingredients % w/w | Optional ingredients weight (g) | Example C8 Ingredients | Ingredients % w/w | Optional ingredients weight (g) |
|---|---|---|---|---|---|
| Oil Phase | | | Oil Phase | | |
| White petrolatum | 60 | 60.45 | White petrolatum | 60 | 60.22 |
| Mineral oil | 10 | 10.04 | Mineral oil | 10 | 10.11 |
| Steareth-2 | 5 | 5.03 | Cetostearyl alcohol | 5 | 5.08 |
| Beeswax substitute | 5 | 5.07 | Beeswax substitute | 5 | 5.09 |
| Hydrophilic phase | | | Hydrophilic phase | | |
| Propylene glycol | 20 | 20.28 | Propylene glycol | 20 | 20.29 |
| Optional Batch size ca. 100 g | | | Optional Batch size ca. 100 g | | |

| Example C9 Ingredients | Ingredients % w/w | Optional ingredients weight (g) | Example C10 Ingredients | Ingredients % w/w | Optional ingredients weight (g) |
|---|---|---|---|---|---|
| Oil Phase | | | Oil Phase | | |
| White petrolatum | 55 | 55.70 | White petrolatum | 63 | 63.23 |
| Mineral oil | 15 | 15.11 | Mineral oil | 10 | 10.09 |
| Cetostearyl alcohol | 5 | 5.02 | Steareth-2 | 5 | 5.03 |
| Beeswax substitute | 5 | 5.07 | Beeswax substitute | 2 | 2.03 |
| Hydrophilic phase | | | Hydrophilic phase | | |
| Propylene glycol | 20 | 20.08 | Propylene glycol | 20 | 20.18 |
| Optional Batch size ca. 100 g | | | Optional Batch size ca. 100 g | | |

| Example C11 Ingredients | Ingredients % w/w | Optional ingredients weight (g) |
|---|---|---|
| Oil phase | | |
| White petrolatum | 58 | 58.50 |
| Mineral oil | 15 | 15.12 |
| Cetostearyl alcohol | 5 | 5.01 |
| Beeswax substitute | 2 | 2.00 |
| Hydrophilic phase | | |
| Propylene glycol | 20 | 20.29 |

Optional Batch size ca. 100 g

Procedure for Composition Examples C5, C6, C7, C8, C9, C10, and C11 (ointment base): The oil phase is melted in a hot water bath to a temperature of approx. 60-70° C. The hydrophilic (propylene glycol) phase is also heated in a hot water bath to a temperature of approx. 60-70° C. The hydrophilic phase is added slowly to the oil phase under low homogenization conditions and is then homogenized at a higher speed for approx. 10 mins under low heat in the water bath. With heating removed, the formulation is then stirred manually with a spatula while being allowed to cool, until room temperature is reached, giving an ointment.

Procedure for Composition Examples C5, C6, C7, C8, C9, C10, and C11 (ointment containing drug): As a modification of the above procedure, after the hydrophilic (propylene glycol) phase is heated to a temperature of approx. 60-70° C. and before addition to the oil phase, the compound of formula (I) is added at 0.1% to 3% w/w or 0.2% to 1.5% w/w (e.g. 0.5% w/w) to the pre-formed hot hydrophilic phase. Then, the hydrophilic phase is added slowly to the oil phase under low homogenization conditions and then is homogenized at a higher speed for approx. 10 mins under low heat in the water bath. With heating removed, the formulation is then stirred (e.g. manually with a spatula) while being allowed to cool to ca. 15-35° C. or ca. 18-30° C. (e.g. to ca. 30° C. or room temperature), giving an ointment (Composition Examples C5, C6, C7, C8, C9, C10, and C11).

Micronisation Example

Purpose: To micronize a compound of formula (I), e.g. in an amount of approximately 600-1000 mg thereof, using a Jetpharma MC1 micronizer.

The parent (unmicronised) and micronised materials are analyzed for particle size by laser diffraction and crystallinity by PXRD.

Equipment and Material

| Equipment/material | Description and specification |
|---|---|
| Jetpharma MC1 Micronizer | Nitrogen supply: Air tank with 275 psi rate tubing |
| Analytical balance | Sartorius Analytical |
| Top loader balance | Mettler PM400 |
| Digital Caliper | VWR Electronic caliper |
| Material to be micronised | A compound of formula (I) |

The Jetpharma MC1 Micronizer comprises a horizontal disc-shaped milling housing having: a tubular compound inlet (e.g. angled at ca. 30 degrees to the horizontal) for entry of a suspension of unmicronised compound of formula (I) or salt in a gasflow, a separate gas inlet for entry of gases, a gas outlet for exit of gases, and a collection vessel (micronizer container) for collecting micronised material. The milling housing has two chambers: (a) an outer annular chamber in gaseous connection with the gas inlet, the chamber being for receiving pressurised gas (e.g. air or nitrogen), and (b) a disc-shaped inner milling chamber within and coaxial with the outer chamber for micronising the input compound/salt, the two chambers being separated by an annular wall. The annular wall (ring R) has a plurality of narrow-bored holes connecting the inner and outer chambers and circumferentially-spaced-apart around the annular wall. The holes opening into the inner chamber are directed at an angle (directed part-way between radially and tangentially), and in use act as nozzles directing pressurised gas at high velocity from the outer chamber into the inner chamber and in an inwardly-spiral path (vortex) around the inner chamber (cyclone). The compound inlet is in gaseous communication with the inner chamber via a nozzle directed tangentially to the inner chamber, within and near to the annular wall/ring R. Upper and lower broad-diameter exit vents in the central axis of the inner milling chamber connect to (a) (lower exit) the collection vessel which has no air outlet, and (b) (upper exit) the gas outlet. Inside and coaxial with the tubular compound inlet and longitudinally-movable within it is positioned a venturi inlet (V) for entry of gases. The compound inlet also has a bifurcation connecting to an upwardly-directed material inlet port for inputting material.

In use, the narrow head of the venturi inlet (V) is preferably positioned below and slightly forward of the material inlet port, so that when the venturi delivers pressurised gas (e.g. air or nitrogen) the feed material is sucked from the material inlet port into the gas stream through the compound inlet and is accelerated into the inner milling chamber tangentially at a subsonic speed. Inside the milling chamber the material is further accelerated to a supersonic speed by the hole/nozzle system around the ring (R) (annular wall) of the milling chamber. The nozzles are slightly angled so that the acceleration pattern of the material is in the form of an inwardly-directed vortex or cyclone. The material inside the milling chamber circulates rapidly and particle collisions occur during the process, causing larger particles to fracture into smaller ones. "Centrifugal" acceleration in the vortex causes the larger particles to remain at the periphery of the inner chamber while progressively smaller particles move closer to the centre until they exit the milling chamber, generally through the lower exit, at low pressure and low velocity. The particles that exit the milling chamber are heavier than air and settle downward through the lower exit into the collection vessel (micronizer container), while the exhaust gas rises (together with a minority of small particles of micronised material) and escapes into the atmosphere at low pressure and low velocity.

Procedure:

The micronizer is assembled. The narrow head of the venturi inlet is positioned below and slightly forward of the material inlet port and is measured with a micro-caliper to make sure that it is inserted correctly. The ring (R) and venturi (V) pressures are adjusted according to the values specified in the experimental design (e.g. refer to experimental section below) by adjusting the valves on the pressure gauges on the micronizer. The setup is checked for leakage by observing if there is any fluctuation in the reading of the pressure gauges.

Note that the venturi (V) pressure is kept at least 2 bars greater than the ring (R) pressure to prevent regurgitation of material, e.g. outwardly from the material inlet port.

Balance performance is checked with calibration weights. Specified amount of the parent material is fed into the input container of the micronizer using a spatula. The input container plus material is weighed. The equipment pressure is monitored during the micronization process.

Upon completion of the micronising run, the nitrogen supply is shut off and the micronised material is allowed to settle into the micronizer container. The micronised powder in the micronizer container (collection vessel) and the cyclone (above the recovery vessel) are collected together into a pre-weighed and labelled collection vial. The weight of the micronised material is recorded. The input container is re-weighed in order to calculate the amount of input material by difference. The micronizer is disassembled and residual PDE4 compound on the micronizer inner surface is rinsed with 70/30 isopropyl alcohol/water and collected into a flask. The micronizer is then thoroughly cleaned in a Lancer washing machine and dried before subsequent runs are performed.

Optional Experimental Parameters

Parent (unmicronised) material (Procedure 1): compound of formula (I)

Balance(s): Sartorius analytical

| Procedure no. | Material input amount (g) | Venturi Pressure (V)/ ring (R) Pressure (bar) | Intended feed-rate | Time needed to feed material (min + sec) | Actual feed-rate (g/min) |
|---|---|---|---|---|---|
| 1 | ca. 0.9 g | V = 8 to 10 bar R = 5.5 to 6 bar | 180 to 200 mg/min | | procedure not carried out |

The above optional parameters can be varied using the skilled person's knowledge.

% yield=[(Material from vessel+Material from cyclone)/Material input amount]×100

Procedure 1 includes possible parameters and conditions and has not been carried out.

Inhalable Composition Example

Dry Powder Formulation Example

Dry Powder Lactose Blend Preparation

Using a size-reduced e.g. micronised form of the compound of formula (I) or salt thereof (e.g. optionally as prepared in the Micronisation Example above), the dry powder blend is prepared by mixing the required amount of the compound/salt (e.g. 10 mg, 1% w/w) with inhalation-grade lactose containing 10% fines (e.g. 990 mg, 99% w/w) in a Teflon™ (polytetrafluoroethene) pot in a Mikro-dismembrator ball-mill (but without a ball bearing) at ¾ speed (ca. 2000-2500 rpm) for about 4 hours at each blend concentration. The Mikro-dismembrator (available from B. Braun Biotech International, Schwarzenberger Weg 73-79, D-34212 Melsungen, Germany; www.bbraunbiotech.com) comprises a base with an upwardly-projecting and sidewardly-vibratable arm to which is attached the Teflon™ pot. The vibration of the arm achieves blending.

Other blends: 10% w/w compound/salt (50 mg)+90% w/w lactose (450 mg, inhalation-grade lactose containing 10% fines).

Serial dilution of the 1% w/w blend can achieve e.g. 0.1% and 0.3% w/w blends.

The invention claimed is:

1. 4-{[1-(Aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof.

2. 4-{[1-(Aminocarbonyl)-4-piperidinyl]amino}-N-[(3,4-dimethylphenyl)methyl]-1-ethyl-1H-pyrazolo[3,4-b]pyridine-5-carboxamide.

3. 4-{[1-(Aminocarbonyl)-4-piperidinyl]amino}-N-[(3,4-dimethylphenyl)methyl]-1-ethyl-1H-pyrazolo[3,4-b]pyridine-5-carboxamide hydrochloride.

4. A pharmaceutical composition comprising 4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof, and one or more pharmaceutically acceptable excipients.

5. A pharmaceutical composition as claimed in claim 4, which is suitable for external topical administration to a human.

6. A pharmaceutical composition as claimed in claim 5, which is an ointment comprising:
   4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof present at 0.1% to 3% w/w;
   an oil phase present at 25% to 99% w/w;
   one or more surfactants present in total at 0.5% to 10% w/w; and
   one or more agents acting as a skin-penetration enhancer present in total at 0.5% to 50% w/w.

7. A pharmaceutical composition as claimed in claim 6, which is an ointment comprising:
   4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof present at 0.2% to 1.5% w/w;
   an oil phase present at 50% to 80% w/w, comprising white petrolatum present at 45 to 75% w/w, and also comprising mineral oil present at 2.5% to 15% w/w;
   one or more surfactants present in total at 3% to 10% w/w; and
   one or more hydrophilic agents acting as both a solubiliser and skin-penetration enhancer, present in total at 5% to 50% w/w;
wherein, in the ointment composition, the oil phase and the hydrophilic solubiliser/penetration-enhancer phase have been emulsified to form an ointment emulsion.

8. A pharmaceutical composition as claimed in claim 5, which is a water-in-oil cream comprising:
   4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof present at 0.1% to 3% w/w;
   an oil phase present at 25% to 85% w/w;
   water present in 2% to 30% w/w;
   one or more surfactants present in total at 0.5% to 12% w/w; and
   one or more agents acting as a skin-penetration enhancer present in total at 0.5% to 50% w/w.

9. A pharmaceutical composition as claimed in claim 8, which is a water-in-oil cream emulsion comprising:
   4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof present at 0.2% to 1.5% w/w;
   an oil phase present at 35% to 70% w/w, comprising white petrolatum present at 30% to 65% w/w and mineral oil present at 2.5% to 15% w/w;
   water present in 5% to 25% w/w;
   one or more surfactants present in total at 3% to 10% w/w; and
   one or more hydrophilic agents acting as both a solubiliser and skin-penetration enhancer, present in total at 5% to 50% w/w.

10. A pharmaceutical composition as claimed in claim 5, which is an oil-in-water cream comprising:
    4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof present at 0.1% to 3% w/w;
    an oil phase containing one or more ingredients capable of acting as emollients, the oil phase being present at 20% to 60% w/w;
    water present in 15% to 75% w/w;
    one or more surfactants present in total at 0.5% to 12% w/w; and
    one or more agents acting as a skin-penetration enhancer, present in total at 0.5% to 50% w/w.

11. A pharmaceutical composition as claimed in claim 10, which is an oil-in-water cream emulsion comprising:
    4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof present at 0.2% to 3% w/w;
    an oil phase containing one or more ingredients capable of acting as emollients, the oil phase being present at 30% to 55% w/w;
    water present in 15% to 50% w/w;
    one or more surfactants present in total at 3% to 10% w/w; and
    one or more hydrophilic agents acting as both a solubiliser and skin-penetration enhancer, present in total at 5% to 50% w/w;
wherein the oil phase comprises mineral oil present at 20% to 45% w/w, and/or microcrystalline wax present at 5% to 25% w/w, and/or a silicone present at 0.5% to 10% w/w.

12. A method for the treatment of atopic dermatitis in a patient comprising administering a therapeutically effective amount of 4-{[1-(aminocarbonyl)-4-piperidinyl]amino}-N-[(3,4-dimethylphenyl)methyl]-1-ethyl-1H-pyrazolo[3,4-b]pyridine-5-carboxamide or a pharmaceutically acceptable salt thereof alone, or in admixture with a pharmaceutically acceptable excipient.

13. A composition of matter according to claim 1 which is
    4-{[1-(aminocarbonyl)-4-piperidinyl]amino}-N-[(3,4-dimethylphenyl)methyl]-1-ethyl-1H-pyrazolo [3,4-b] pyridine-5-carboxamide hydrobromide,
    4-{[1-(aminocarbonyl)-4-piperidinyl]amino}-N-[(3,4-dimethylphenyl)methyl]-1-ethyl-1H-pyrazolo [3,4-b] pyridine-5-carboxamide sulfate,
    4-{[1-(aminocarbonyl)-4-piperidinyl]amino}-N-[(3,4-dimethylphenyl)methyl]-1-ethyl-1H-pyrazolo [3,4-b] pyridine-5-carboxamide nitrate,
    4-{[1-(aminocarbonyl)-4-piperidinyl]amino}-N-[(3,4-dimethylphenyl)methyl]-1-ethyl-1H-pyrazolo [3,4-b] pyridine-5-carboxamide phosphate,
    4-{[1-(aminocarbonyl)-4-piperidinyl]amino}-N-[(3,4-dimethylphenyl)methyl]-1-ethyl-1H-pyrazolo [3,4-b] pyridine-5-carboxamide p-toluenesulfonate,
    4-{[1-(aminocarbonyl)-4-piperidinyl]amino}-N-[(3,4-dimethylphenyl)methyl]-1-ethyl-1H-pyrazolo [3,4-b] pyridine-5-carboxamide benzenesulfonate,
    4-{[1-(aminocarbonyl)-4-piperidinyl]amino}-N-[(3,4-dimethylphenyl)methyl]-1-ethyl-1H-pyrazolo [3,4-b] pyridine-5-carboxamide methanesulfonate,
    4-{[1-(aminocarbonyl)-4-piperidinyl]amino}-N-[(3,4-dimethylphenyl)methyl]-1-ethyl-1H-pyrazolo [3,4-b] pyridine-5-carboxamide ethanesulfonate, or
    4-{[1-(aminocarbonyl)-4-piperidinyl]amino}-N-[(3,4-dimethylphenyl)methyl]-1-ethyl-1H-pyrazolo [3,4-b] pyridine-5-carboxamide naphthalenesulfonate.

* * * * *